US 12,370,252 B2

(12) United States Patent
Ha et al.

(10) Patent No.: US 12,370,252 B2
(45) Date of Patent: Jul. 29, 2025

(54) RSV VIRUS-LIKE PARTICLES AND METHODS OF USE THEREOF

(71) Applicants: EMORY UNIVERSITY, Atlanta, GA (US); CHILDREN'S HEALTHCARE OF ATLANTA, Atlanta, GA (US); WISCONSIN ALUMNI RESEARCH FOUNDATION, Madison, WI (US)

(72) Inventors: Binh Ha, Atlanta, GA (US); Larry J. Anderson, Atlanta, GA (US); Elizabeth R. Wright, Atlanta, GA (US)

(73) Assignees: Emory University, Atlanta, GA (US); Children's Healthcare of Atlanta, Atlanta, GA (US); Wisconsin Alumni Research Foundation, Madison, WI (US)

( * ) Notice: Subject to any disclaimer, the term of this patent is extended or adjusted under 35 U.S.C. 154(b) by 1070 days.

(21) Appl. No.: 17/289,827

(22) PCT Filed: Oct. 29, 2019

(86) PCT No.: PCT/US2019/058559
§ 371 (c)(1),
(2) Date: Apr. 29, 2021

(87) PCT Pub. No.: WO2020/092365
PCT Pub. Date: May 7, 2020

(65) Prior Publication Data
US 2021/0401969 A1    Dec. 30, 2021

Related U.S. Application Data

(60) Provisional application No. 62/751,975, filed on Oct. 29, 2018.

(51) Int. Cl.
*A61K 39/155* (2006.01)
*A61K 39/39* (2006.01)
*C12N 7/00* (2006.01)

(52) U.S. Cl.
CPC ......... *A61K 39/155* (2013.01); *A61K 39/39* (2013.01); *C12N 7/00* (2013.01); *C12N 2760/18023* (2013.01); *C12N 2760/18034* (2013.01)

(58) Field of Classification Search
None
See application file for complete search history.

(56) References Cited

U.S. PATENT DOCUMENTS

| 8,741,311 | B2 * | 6/2014 | Wong | A61P 31/16 424/210.1 |
| 8,920,812 | B2 | 12/2014 | Haynes | |
| 10,899,800 | B2 * | 1/2021 | Langedijk | A61K 39/12 |
| 2008/0233150 | A1 | 9/2008 | Smith et al. | |
| 2011/0097358 | A1 | 4/2011 | Galarza et al. | |
| 2016/0102123 | A1 * | 4/2016 | Langedijk | C07K 14/005 536/23.4 |
| 2017/0290906 | A1 | 10/2017 | Compans et al. | |
| 2017/0319682 | A1 | 11/2017 | Smith et al. | |
| 2019/0002537 | A1 | 1/2019 | Perret et al. | |

FOREIGN PATENT DOCUMENTS

| JP | 2018007655 A | 1/2018 |
| WO | 2017055775 A1 | 4/2017 |

OTHER PUBLICATIONS

Walpita et al., PLOS One;10(7):e0130755 (Year: 2015).*
Meshram et al., Journal of Virology vol. 90 No. 23, pp. 10612-10628 (Year: 2016).*
Comparison to SEQ ID No. 3 (Year: 2024).*
Comparison to SEQ ID No. 23 (Year: 2024).*
International Search Report and Written Opinion for International Application No. PCT/US2019/058559 dated Feb. 27, 2020.
Cimica et al., Novel Respiratory Syncytial Virus-Like Particle Vaccine Composed of the Postfusion and Prefusion Conformations of the F Glycoprotein. Clin Vaccine Immunol. 2016, vol. 23(6), p. 451-9.
Mitra et al., The Human Respiratory Syncytial Virus Matrix Protein Is Required for Maturation of Viral Filaments. J Virol. 2012, vol. 86(8), p. 4432-43.
Meshram et al., The Respiratory Syncytial Virus Phosphoprotein, Matrix Protein, and Fusion Protein Carboxy-Terminal Domain Drive Efficient Filamentous Virus-Like Particle Formation. J Virol. 2016, vol. 90(23), p. 10612-10628.
Supplementary Partial European Search report, mailed May 25, 2022, received in connection with corresponding EP Patent Application No. 19873849.4.
International Preliminary Report on Patentability issued for Application No. PCT/US2019/058559, dated May 14, 2021.

(Continued)

*Primary Examiner* — Shanon A. Foley
*Assistant Examiner* — Myron G H
(74) *Attorney, Agent, or Firm* — Meunier Carlin & Curfman LLC

(57) ABSTRACT

The present disclosure relates to virus-like particles and vaccine compositions for inducing immunity and preventing respiratory syncytial virus (RSV) infection. Specifically, the disclosure provides virus like-particles (VLPs) for use in inducing immunity to respiratory syncytial virus (RSV) infections or symptoms thereof, wherein the VLP comprising a respiratory RSV matrix protein (M) and an RSV M2-1 protein, a glycoprotein (G), a fusion protein (F), and/or a phosphoprotein (P).

8 Claims, 8 Drawing Sheets

Specification includes a Sequence Listing.

(56) References Cited

OTHER PUBLICATIONS

Altschul, Stephen F., et al. "Basic local alignment search tool." Journal of molecular biology 215.3 (1990): 403-410.
Altschul, Stephen F., et al. "Gapped BLAST and PSI-BLAST: a new generation of protein database search programs." Nucleic acids research 25.17 (1997): 3389-3402.
Anderson LJ. Respiratory syncytial virus vaccine development. Seminars in immunology. 2013;25(2):160-171.
Bakker SE, Duquerroy S, Galloux M, et al. The respiratory syncytial virus nucleoprotein-RNA complex forms a left-handed helical nucleocapsid. J Gen Virol. 2013;94(Pt 8):1734-1738.
Beaucage, S. L., and M. H. Caruthers. "Deoxynucleoside phosphoramidites—a new class of key intermediates for deoxypolynucleotide synthesis." Tetrahedron letters 22.20 (1981): 1859-1862.
Boyoglu-Barnum S, Gaston KA, Todd SO, et al. A respiratory syncytial virus (RSV) anti-G protein F(ab')2 monoclonal antibody suppresses mucous production and breathing effort in RSV rA2-line19F-infected BALB/c mice. J Virol. 2013;87(20):10955-10967.
Boyoglu-Barnum S, Todd SO, Chirkova T, et al. An anti-G protein monoclonal antibody treats RSV disease more effectively than an anti-F monoclonal antibody in BALB/c mice. Virology. 2015;483:117-125.
Boyoglu-Barnum S, Todd SO, Meng J, et al. Mutating the CX3C Motif in the G Protein Should Make a Live Respiratory Syncytial Virus Vaccine Safer and More Effective. J Virol. 2017;91(10).
Chirkova T, Boyoglu-Barnum S, Gaston KA, et al. Respiratory syncytial virus G protein CX3C motif impairs human airway epithelial and immune cell responses. J Virol. 2013;87(24):13466-13479.
Chirkova T, Lin S, Oomens AG, et al. CX3CR1 is an important surface molecule for respiratory syncytial virus infection in human airway epithelial cells. J Gen Virol. 2015;96(9):2543-2556.
Collins PL CJ. Respiratory syncytial virus and metapneumovirus. In: Fields virology, 5th ed. Philadelphia, PA: Lippincott Williams & Wilkins; 2007:1601-1646. Abstract.
Collins PL, Fearns R, Graham BS. Respiratory Syncytial Virus: Virology, Reverse Genetics, and Pathogenesis of Disease. In: Anderson LJ, Graham BS, eds. Challenges and Opportunities for Respiratory Syncytial Virus Vaccines. Current Topics in Microbiology and Immunology, vol. 372. vol. 372. Berlin, Heidelberg Springer; 2013:3-38.
Connors M, Collins PL, Firestone C-Y, Murphy BR. Respiratory syncytial virus (RSV) F, G, M2 (22K), and N proteins each induce resistance to RSV Challenge, but resistance induced by M2 and N proteins is relatively short-lived. J Virol. 1991;65:1634-1637.
Cowton VM, McGivern DR, Fearns R. Unravelling the complexities of respiratory syncytial virus RNA synthesis. J Gen Virol. 2006;87(Pt 7):1805-1821.
Cullen, Lori M., Madelyn R. Schmidt, and Trudy G. Morrison. "The importance of RSV F protein conformation in VLPs in stimulation of neutralizing antibody titers in mice previously infected with RSV." Human vaccines & immunotherapeutics 13.12 (2017): 2814-2823.
Esperante SA, Paris G, de Prat-Gay G. Modular unfolding and dissociation of the human respiratory syncytial virus phosphoprotein p and its interaction with the m(2-1) antiterminator: a singular tetramer-tetramer interface arrangement. Biochemistry. 2012;51(41):8100-8110.
Fearns R, Collins PL. Role of the M2-1 transcription antitermination protein of respiratory syncytial virus in sequential transcription. J Virol. 1999;73(7):5852-5864.
Graham BS. Immunological goals for respiratory syncytial virus vaccine development. Curr Opin Immunol. 2019;59:57-64.
Green CA, Scarselli E, Sande CJ, et al. Chimpanzee adenovirus- and MVA-vectored respiratory syncytial virus vaccine is safe and immunogenic in adults. Science translational medicine. 2015;7(300):300ra126.
Hall CB, Simoes EA, Anderson LJ. Clinical and epidemiologic features of respiratory syncytial virus. Curr Top Microbiol Immunol. 2013;372:39-57.
Hall CB, Weinberg GA, Iwane MK, et al. The burden of respiratory syncytial virus infection in young children. N Engl J Med. 2009;360(6):588-598.
Henikoff, Steven, and Jorja G. Henikoff. "Amino acid substitution matrices from protein blocks." Proceedings of the National Academy of Sciences 89.22 (1992): 10915-10919.
Jartti T, Gern JE. Role of viral infections in the development and exacerbation of asthma in children. J Allergy Clin Immunol. 2017;140(4):895-906.
Jeong KI, Piepenhagen PA, Kishko M, et al. CX3CR1 Is Expressed in Differentiated Human Ciliated Airway Cells and Co-Localizes with Respiratory Syncytial Virus on Cilia in a G Protein-Dependent Manner. PLoS One. 2015;10(6):e0130517.
Johnson SM, McNally BA, Ioannidis I, et al. Respiratory Syncytial Virus Uses CX3CR1 as a Receptor on Primary Human Airway Epithelial Cultures. PLoS Pathog. 2015;11(12):e1005318.
Jorquera PA, Choi Y, Oakley KE, et al. Nanoparticle vaccines encompassing the respiratory syncytial virus (RSV) G protein CX3C chemokine motif induce robust immunity protecting from challenge and disease. PLoS One. 2013;8(9):e74905.
Karlin, Samuel, and Stephen F. Altschul. "Applications and statistics for multiple high-scoring segments in molecular sequences." Proceedings of the National Academy of Sciences 90.12 (1993): 5873-5877.
Ke Z, Dillard RS, Chirkova T, et al. The Morphology and Assembly of Respiratory Syncytial Virus Revealed by Cryo-Electron Tomography. Viruses. 2018;10(8).
Kiss G, Holl JM, Williams GM, et al. Structural analysis of respiratory syncytial virus reveals the position of M2-1 between the matrix protein and the ribonucleoprotein complex. J Virol. 2014;88(13):7602-7617.
Krarup A, Truan D, Furmanova-Hollenstein P, et al. A highly stable prefusion RSV F vaccine derived from structural analysis of the fusion mechanism. Nat Commun. 2015;6:8143.
Li D, Jans DA, Bardin PG, Meanger J, Mills J, Ghildyal R. Association of respiratory syncytial virus M protein with viral nucleocapsids is mediated by the M2-1 protein. J Virol. 2008;82(17):8863-8870.
Liu J, Haddad EK, Marceau J, et al. A Numerically Subdominant CD8 T Cell Response to Matrix Protein of Respiratory Syncytial Virus Controls Infection with Limited Immunopathology. PLoS Pathog. 2016;12(3):e1005486.
Lowy, Douglas R. "HPV vaccination to prevent cervical cancer and other HPV-associated disease: from basic science to effective interventions." The Journal of clinical investigation 126.1 (2016): 5-11.
Matteucci, Mark Douglas, and M. Ho Caruthers. "Synthesis of deoxyoligonucleotides on a polymer support." Journal of the American Chemical Society 103.11 (1981): 3185-3191.
Mazur NI, Higgins D, Nunes MC, et al. The respiratory syncytial virus vaccine landscape: lessons from the graveyard and promising candidates. Lancet Infect Dis. 2018;18(10):e295-e311.
McLellan JS, Chen M, Joyce MG, et al. Structure-based design of a fusion glycoprotein vaccine for respiratory syncytial virus. Science. 2013;342(6158):592-598.
McLellan JS, Ray WC, Peeples ME. Structure and function of respiratory syncytial virus surface glycoproteins. Curr Top Microbiol Immunol. 2013;372:83-104.
Meshram CD, Baviskar PS, Ognibene CM, Oomens AG. The Respiratory Syncytial Virus Phosphoprotein, Matrix Protein, and Fusion Protein Carboxy-Terminal Domain Drive Efficient Filamentous Virus-Like Particle Formation. J Virol. 2016;90(23):10612-10628.
Moore ML, Chi MH, Luongo C, et al. A chimeric A2 strain of respiratory syncytial virus (RSV) with the fusion protein of RSV strain line 19 exhibits enhanced viral load, mucus, and airway dysfunction. J Virol. 2009;83(9):4185-4194.
Murawski MR, McGinnes LW, Finberg RW, et al. Newcastle disease virus-like particles containing respiratory syncytial virus G protein induced protection in BALB/c mice, with no evidence of immunopathology. J Virol. 2010;84(2):1110-1123.

(56) References Cited

OTHER PUBLICATIONS

Ngwuta JO, Chen M, Modjarrad K, et al. Prefusion F-specific antibodies determine the magnitude of RSV neutralizing activity in human sera. Science translational medicine. 2015;7(309):309ra162.
Quan FS, Kim Y, Lee S, et al. Viruslike particle vaccine induces protection against respiratory syncytial virus infection in mice. J Infect Dis. 2011;204(7):987-995.
Radu GU, Caidi H, Miao C, Tripp RA, Anderson LJ, Haynes LM. Prophylactic treatment with a G glycoprotein monoclonal antibody reduces pulmonary inflammation in respiratory syncytial virus (RSV)-challenged naive and formalin-inactivated RSV-immunized BALB/c mice. J Virol. 2010;84(18):9632-9636.
Rey GU, Miao C, Caidi H, et al. Decrease in formalin-inactivated respiratory syncytial virus (FI-RSV) enhanced disease with RSV G glycoprotein peptide immunization in BALB/c mice. PLoS One. 2013;8(12):e83075.
Schepens B, Sedeyn K, Vande Ginste L, et al. Protection and mechanism of action of a novel human respiratory syncytial virus vaccine candidate based on the extracellular domain of small hydrophobic protein. EMBO Mol Med. 2014;6(11):1436-1454.
Schmidt, Madelyn R., et al. "Long-term and memory immune responses in mice against Newcastle disease virus-like particles containing respiratory syncytial virus glycoprotein ectodomains." Journal of virology 86.21 (2012): 11654-11662.
Schwarz B, Morabito KM, Ruckwardt TJ, et al. Viruslike Particles Encapsidating Respiratory Syncytial Virus M and M2 Proteins Induce Robust T Cell Responses. ACS Biomater Sci Eng. 2016;2(12):2324-2332.
Shaikh FY, Cox RG, Lifland AW, et al. A critical phenylalanine residue in the respiratory syncytial virus fusion protein cytoplasmic tail mediates assembly of internal viral proteins into viral filaments and particles. mBio. 2012;3(1).
Shi T, McAllister DA, O'Brien KL, et al. Global, regional, and national disease burden estimates of acute lower respiratory infections due to respiratory syncytial virus in young children in 2015: a systematic review and modelling study. Lancet. 2017;390(10098):946-958.
Stockman LJ, Curns AT, Anderson LJ, Fischer-Langley G. Respiratory Syncytial Virus-associated Hospitalizations Among Infants and Young Children in the United States, 1997-2006. Pediatr Infect Dis J. 2012;31(1):5-9.
Stone AB. A simplified method for preparing sucrose gradients. Biochem J. 1974;137(1):117-118.
Tanner SJ, Ariza A, Richard CA, et al. Crystal structure of the essential transcription antiterminator M2-1 protein of human respiratory syncytial virus and implications of its phosphorylation. Proc Natl Acad Sci U S A. 2014;111(4):1580-1585.
Tawar RG, Duquerroy S, Vonrhein C, et al. Crystal structure of a nucleocapsid-like nucleoprotein-RNA complex of respiratory syncytial virus. Science. 2009;326(5957):1279-1283.
Tripp RA, Power UF, Openshaw PJM, Kauvar LM. Respiratory Syncytial Virus: Targeting the G Protein Provides a New Approach for an Old Problem. J Virol. 2018;92(3).
Tripp RA. CX3C chemokine mimicry by respiratory syncytial virus G glycoprotein. In: Mahalingam S, ed. Chemokines in Viral Infection. Landes Bioscience; 2003.
Walpita P, Johns LM, Tandon R, Moore ML. Mammalian Cell-Derived Respiratory Syncytial Virus-Like Particles Protect the Lower as well as the Upper Respiratory Tract. PLoS One. 2015;10(7):e0130755.
Wu P, Hartert TV. Evidence for a causal relationship between respiratory syncytial virus infection and asthma. Expert Rev Anti Infect Ther. 2011;9(9):731-745.
Zhang W, Choi Y, Haynes LM, et al. Vaccination to induce antibodies blocking the CX3C-CX3CR1 interaction of respiratory syncytial virus G protein reduces pulmonary inflammation and virus replication in mice. J Virol. 2010;84(2):1148-1157.

* cited by examiner

A

MFGP                    MFGM2-1

B

Motavizumab             3D3

A

B

```
         1          86   155   206       298
Ga  NH₂ [====TM====|====CCD-G====]COOH
         1          77  146   197       299
Gb  NH₂ [====TM====|====CCD-G====]COOH 1                          524  574
F_post or F_pre NH₂ [ F1 |       F2       |TM] COOH
```

Ga: G protein from A2 strain
Gb: G protein from B1 strain
$F_{post}$: post fusion form of F protein
$F_{pre}$: pre fusion form of F protein

Combinations of F and G expression of RSV VLPs:

1. Platform M + P:
a) $F_{post}$ + Ga
b) $F_{post}$ + Ga (aa 1-206)
c) $F_{post}$ + Ga (aa 1-86, 155-206)
d) $F_{post}$ + Ga (aa 1-86, 155-206) + Ga (aa 1-86, 155-206) (Ga tandem)
e) $F_{post}$ + Gb (aa 1-77, 146-197) + Gb (aa 1-77, 146-197) (Gb tandem)
f) $F_{post}$ + Ga (aa 1-86, 155-206) + Gb (aa 1-77, 146-197) (Hybrid tandem)
g) $F_{pre}$ + Ga
h) $F_{pre}$ + Ga (aa 1-206)
i) $F_{pre}$ + Ga (aa 1-86, 155-206)
j) $F_{pre}$ + Ga (aa 1-86, 155-206) + Ga (aa 1-86, 155-206) (Ga tandem)
k) $F_{pre}$ + Gb (aa 1-77, 146-197) + Gb (aa 1-77, 146-197) (Gb tandem)
l) $F_{pre}$ + Ga (aa 1-86, 155-206) + Gb (aa 1-77, 146-197) (Hybrid tandem)

2. Platform M + M2-1: same combinations as above.

FIG. 6

\* indicates mutation site

SEQUENCE LISTING

<160> NUMBER OF SEQ ID NOS: 50

<210> SEQ ID NO 1
<211> LENGTH: 138
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 1

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Ile
        35                  40                  45

Val Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Pro Pro Ser Lys Pro Asn Asn Asp Phe His
                85                  90                  95

Phe Glu Val Phe Asn Phe Val Pro Cys Ser Ile Cys Ser Asn Asn Pro
            100                 105                 110

Thr Cys Trp Ala Ile Cys Lys Arg Ile Pro Asn Lys Pro Gly Lys
        115                 120                 125

Lys Thr Thr Thr Lys Pro Thr Lys Lys Pro
        130                 135

<210> SEQ ID NO 2
<211> LENGTH: 417
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 2
atgagcaaga caaggacca gcggaccgcc aagacactgg aaagaacctg ggacaccctg      60
aaccatctgc tgttcatcag cagctgcctg tacaagctga acctgaagtc tgtggcccag     120
atcaccctga gcatcctggc catcgtgatc agcaccagcc tgatcattgc cgccatcatc     180
tttatcgcca gcgccaacca caaagtgacc cctaccacag ccatcatcca ggacgccaca     240
agccagatca gaacaccccc tccaagcaag cccaacaacg acttccactt cgaggtgttc     300
aacttcgtgc cctgcagcat ctgcagcaac aatcctacct gctgggccat ctgcaagaga     360
atccccaaca agaagcccgg caaaaagacc accacaaagc ccacaaagaa gccctag        417

<210> SEQ ID NO 3
<211> LENGTH: 206
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 3

Met Ser Lys Asn Lys Asp Gln Arg Thr Thr Lys Thr Leu Glu Lys Thr
1               5                   10                  15

Trp Asp Thr Leu Asn His Leu Leu Phe Ile Ser Ser Cys Leu Tyr Lys
            20                  25                  30

```
Leu Asn Leu Lys Ser Ile Ala Gln Ile Thr Leu Ser Ile Leu Ala Met
         35                  40                  45

Ile Ile Ser Thr Ser Leu Ile Ile Ala Ala Ile Phe Ile Ala Ser
 50                  55                  60

Ala Asn His Lys Val Thr Leu Thr Thr Ala Ile Ile Gln Asp Ala Thr
 65                  70                  75                  80

Ser Gln Ile Lys Asn Thr Thr Pro Thr Tyr Leu Thr Gln Asn Pro Gln
                 85                  90                  95

Leu Gly Ile Ser Phe Ser Asn Leu Ser Glu Thr Thr Ser Gln Thr Thr
             100                 105                 110

Thr Ile Leu Ala Ser Thr Thr Pro Ser Val Lys Ser Thr Leu Gln Ser
         115                 120                 125

Thr Thr Val Lys Thr Lys Asn Thr Thr Thr Thr Lys Ile Gln Pro Ser
 130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                 165                 170                 175

Ser Asn Asn Pro Thr Cys Trp Ala Ile Cys Lys Arg Ile Pro Asn Lys
             180                 185                 190

Lys Pro Gly Lys Lys Thr Thr Thr Lys Pro Thr Lys Lys Pro
         195                 200                 205

<210> SEQ ID NO 4
<211> LENGTH: 618
<212> TYPE: DNA
<213> ORGANISM: ARTIFICIAL SEQUENCE
<220> FEATURE:
<223> OTHER INFORMATION: SYNTHETIC CONTRUCT

<400> SEQUENCE: 4
atgtccaaaa acaaggacca acgcaccacc aagacactag aaaagacctg ggacactctc      60
aatcatctat tattcatatc atcgtgctta tacaagttaa atcttaaatc tatagcacaa     120
atcacattat ccattctggc aatgataatc tcaacttcac ttataattgc agccatcata     180
ttcatagcct cggcaaacca caaagtcaca ctaacaactg caatcataca agatgcaaca     240
agccagatca gaacacaaac cccaacatac ctcacccaga atccccagct tggaatcagc     300
ttctccaatc tgtctgaaac tacatcacaa accaccacca tactagcttc aacaacacca     360
agtgtcaagt caaccctgca atccacaaca gtcaagacca aaacacaaac aacaaccaaa     420
atacaaccca gcaagcccac cacaaaaaca cgccaaaaca aaccaccaaa caaacccaat     480
aatgattttc actttgaagt gttcaacttt gtaccttgca gcatatgcag caacaatcca     540
acctgctggg ctatctgtaa aagaatacca aacaaaaaac tggaaagaa accaccacc      600 aagcccacaa aaaaacca                                                   618

<210> SEQ ID NO 5
<211> LENGTH: 206
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 5

Met Ser Lys Asn Lys Asp Gln Arg Thr Ala Lys Thr Leu Glu Arg Thr
 1               5                  10                  15

Trp Asp Thr Leu Asn His Leu Leu Phe Ile Ser Ser Cys Leu Tyr Lys
```

```
                20                  25                  30
Leu Asn Leu Lys Ser Val Ala Gln Ile Thr Leu Ser Ile Leu Ala Ile
            35                  40                  45

Val Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Gln Thr Gln Pro Ser
        130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro
        195                 200                 205
```

<210> SEQ ID NO 6
<211> LENGTH: 621
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 6

```
atgagcaaga acaaggacca gcggaccgcc aagacactgg aaagaacctg ggacaccctg      60
aaccatctgc tgttcatcag cagctgcctg tacaagctga acctgaagtc tgtggcccag    120
atcaccctga gcatcctggc catcgtgatc agcaccagcc tgatcattgc cgccatcatc    180
tttatcgcca gcgccaacca caaagtgacc cctaccacag ccatcatcca ggacgccaca    240
agccagatca agaacaccac acctacctac ctgacacaga accctcagct gggcatcagc    300
cctagcaatc ctagcgagat cacctctcag atcaccacaa tcctggccag cacaaacccct    360
ggcgtgaagt ctacactgca gagcaccacc gtgaaaacga agaataccac caccacacag    420
acccagccta gcaagcctac caccaagcag agacagaaca agcctccaag caagcccaac    480
aacgacttcc acttcgaggt gttcaacttc gtgccctgca gcatctgcag caacaatcct    540
acctgctggg ccatctgcaa gagaatcccc aacaagaagc ccggcaaaaa gaccaccaca    600
aagcccacaa agaagcccta g                                              621
```

<210> SEQ ID NO 7
<211> LENGTH: 298
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

```
Met Ser Lys Asn Lys Asp Gln Arg Thr Thr Lys Thr Leu Glu Lys Thr
1               5                   10                  15
```

Trp Asp Thr Leu Asn His Leu Leu Phe Ile Ser Ser Cys Leu Tyr Lys
                 20                  25                  30

Leu Asn Leu Lys Ser Ile Ala Gln Ile Thr Leu Ser Ile Leu Ala Met
             35                  40                  45

Ile Ile Ser Thr Ser Leu Ile Ala Ala Ile Phe Ile Ala Ser
 50                  55                  60

Ala Asn His Lys Val Thr Leu Thr Thr Ala Ile Ile Gln Asp Ala Thr
 65                  70                  75                  80

Ser Gln Ile Lys Asn Thr Thr Pro Tyr Leu Thr Gln Asn Pro Gln
                 85                  90                  95

Leu Gly Ile Ser Phe Ser Asn Leu Ser Glu Thr Thr Ser Gln Thr Thr
                100                 105                 110

Thr Ile Leu Ala Ser Thr Thr Pro Ser Val Lys Ser Thr Leu Gln Ser
                115                 120                 125

Thr Thr Val Lys Thr Lys Asn Thr Thr Thr Lys Ile Gln Pro Ser
130                 135                 140

Lys Pro Thr Thr Lys Gln Arg Gln Asn Lys Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Ile
            195                 200                 205

Lys Thr Thr Lys Lys Asp Leu Lys Pro Gln Thr Thr Lys Pro Lys Glu
            210                 215                 220

Val Pro Thr Thr Lys Pro Thr Glu Lys Pro Thr Ile Asn Thr Thr Lys
225                 230                 235                 240

Thr Asn Ile Arg Thr Thr Leu Leu Thr Asn Asn Thr Thr Gly Asn Pro
                245                 250                 255

Glu His Thr Ser Gln Lys Gly Thr Leu His Ser Thr Ser Ser Asp Gly
            260                 265                 270

Asn Pro Ser Pro Ser Gln Val Tyr Thr Thr Ser Glu Tyr Leu Ser Gln
            275                 280                 285

Pro Pro Ser Pro Ser Asn Thr Thr Asn Gln
            290                 295

<210> SEQ ID NO 8
<211> LENGTH: 837
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 8
atgtccaaaa acaaggacca acgcaccacc aagacactag aaaagaaatc tatagcacaa      60
atcacattat ccattctggc aatgataatc tcaacttcac ttataattgc agccatcata     120
ttcatagcct cggcaaaacca caaagtcaca ctaacaactg caatcataca agatgcaaca     180
agccagatca agaacacaac cccaacatac ctcacccaga tccccagct tggaatcagc      240 ttctccaatc tgtctgaaac tacatcacaa accaccacca tactagcttc aacaacacca     300
agtgtcaagt caaccctgca atccacaaca gtcaagacca aaaacacaac aaccaccaaa     360
atacaaccca gcaagcccac cacaaaaaca cgccaaaaca accaccaaa caaacccaat     420

```
aatgattttc actttgaagt gttcaacttt gtaccttgca gcatatgcag caacaatcca    480
acctgctggg ctatctgtaa aagaatacca aacaaaaaac ctggaaagaa accaccacc    540 aagcccacaa aaaaccaac catcaagaca accaaaaaag atctcaaacc tcaaaccaca    600
aaaccaaagg aagtacctac caccaagccc acagaaaagc caaccatcaa caccaccaaa    660
acaaacatca gaactacact gctcaccaac aataccacag gaaatccaga acacacaagt    720
caaaagggaa ccctccactc aacctcctcc gatggcaatc caagcccttc acaagtctat    780
acaacatccg agtacctatc acaacctcca tctccatcca cacaacaaa ccagtag       837
```

<210> SEQ ID NO 9
<211> LENGTH: 298
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 9

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Ile
        35                  40                  45

Val Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295
```

```
                   290                 295

<210> SEQ ID NO 10
<211> LENGTH: 897
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 10
atgagcaaga caaggacca gcggaccgcc aagacactgg aaagaacctg ggacaccctg      60
aaccatctgc tgttcatcag cagctgcctg tacaagctga acctgaagtc tgtggcccag    120
atcaccctga gcatcctggc catcgtgatc agcaccagcc tgatcattgc cgccatcatc    180
tttatcgcca cgccaacca caaagtgacc cctaccacag ccatcatcca ggacgccaca     240
agccagatca agaacaccac acctacctac ctgacacaga accctcagct gggcatcagc    300
cctagcaatc ctagcgagat cacctctcag atcaccacaa tcctggccag cacaacccct    360
ggcgtgaagt ctacactgca gagcaccacc gtgaaaacga gaataccac caccacacag     420 acccagccta gcaagcctac caccaagcag agacagaaca gcctccaag caagcccaac     480 aacgacttcc acttcgaggt gttcaacttc gtgccctgca gcatctgcag caacaatcct    540
acctgctggg ccatctgcaa gagaatcccc aacaagaagc ccggcaaaaa gaccaccaca    600
aagcccacaa agaagcccac actgaaaacc accaagaagg accccaagcc tcagaccacc    660
aagtccaaag aggtgcccac caccaaacct accgaggaac ccaccatcaa caccactaag    720
accaacatca tcaccacact gctgacctcc aacaccaccg gcaatcctga actgaccagc    780
cagatggaaa ccttccacag cacctccagc gagggcaacc catctcctag tcaggtgtcc    840
accacaagcg agtaccctag ccagccaagc agccctccta acacacctag acagtag       897

<210> SEQ ID NO 11
<211> LENGTH: 138
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 11

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Ile
        35                  40                  45

Val Ile Ser Thr Ser Leu Ile Ile Ala Ala Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Pro Pro Ser Lys Pro Asn Asn Asp Phe His
                85                  90                  95

Phe Glu Val Phe Asn Phe Val Pro Cys Ser Ile Cys Ser Asn Asn Pro
            100                 105                 110

Thr Cys Trp Ala Ile Ala Cys Lys Arg Ile Pro Asn Lys Pro Gly Lys
        115                 120                 125

Lys Thr Thr Thr Lys Pro Thr Lys Lys Pro
    130                 135
```

<210> SEQ ID NO 12
<211> LENGTH: 420
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 12

| | | | | | |
|---|---|---|---|---|---|
| atgagcaaga | acaaggacca | gcggaccgcc | aagacactgg | aaagaacctg | ggacaccctg | 60 |
| aaccatctgc | tgttcatcag | cagctgcctg | tacaagctga | acctgaagtc | tgtggcccag | 120 |
| atcaccctga | gcatcctggc | catcgtgatc | agcaccagcc | tgatcattgc | cgccatcatc | 180 |
| tttatcgcca | gcgccaacca | caaagtgacc | cctaccacag | ccatcatcca | ggacgccaca | 240 |
| agccagatca | agaacacccc | tccaagcaag | cccaacaacg | acttccactt | cgaggtgttc | 300 |
| aacttcgtgc | cctgcagcat | ctgcagcaac | aatcctacct | gctgggccat | cgcctgcaag | 360 |
| agaatcccca | caagaagcc | cggcaaaaag | accaccacaa | agcccacaaa | gaagccctag | 420 |

<210> SEQ ID NO 13
<211> LENGTH: 299
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 13

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Ile
        35                  40                  45

Val Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Ala Cys Lys Arg Ile Pro Asn
            180                 185                 190

Lys Lys Pro Gly Lys Lys Thr Thr Thr Lys Pro Thr Lys Lys Pro Thr
        195                 200                 205

Leu Lys Thr Thr Lys Lys Asp Pro Lys Pro Gln Thr Thr Lys Ser Lys
    210                 215                 220

Glu Val Pro Thr Thr Lys Pro Thr Glu Glu Pro Thr Ile Asn Thr Thr
225                 230                 235                 240

```
Lys Thr Asn Ile Ile Thr Thr Leu Leu Thr Ser Asn Thr Gly Asn
                245                 250                 255

Pro Glu Leu Thr Ser Gln Met Glu Thr Phe His Ser Thr Ser Ser Glu
            260                 265                 270

Gly Asn Pro Ser Pro Ser Gln Val Ser Thr Thr Ser Glu Tyr Pro Ser
            275                 280                 285

Gln Pro Ser Ser Pro Pro Asn Thr Pro Arg Gln
            290                 295
```

<210> SEQ ID NO 14
<211> LENGTH: 900
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 14

```
atgagcaaga caaggacca gcggaccgcc aagacactgg aaagaacctg ggacaccctg    60
aaccatctgc tgttcatcag cagctgcctg tacaagctga acctgaagtc tgtggcccag   120
atcaccctga gcatcctggc catcgtgatc agcaccagcc tgatcattgc cgccatcatc   180
tttatcgcca cgccaaccca aaagtgacc cctaccacag ccatcatcca ggacgccaca    240
agccagatca agaacaccac acctacctac ctgacacaga accctcagct gggcatcagc   300
cctagcaatc ctagcgagat cacctctcag atcaccacaa tcctggccag cacaaccect   360 ggcgtgaagt ctacactgca gagcaccacc gtgaaaacga agaataccac caccacacag   420
acccagccta gcaagcccta caccaagcag agacagaaca gcctccaag caagcccaac    480 aacgacttcc acttcgaggt gttcaacttc gtgccctgca gcatctgcag caacaatcct   540
acctgctggg ccatcgcctg caagagaatc cccaacaaga gcccggcaa aaagaccacc    600 acaaagccca aagaagcc cacactgaaa accaccaaga aggaccccaa gcctcagacc    660
accaagtcca agaggtgcc caccaccaaa cctaccgagg aaacccaccat caacaccact   720 aagaccaaca tcatcaccac actgctgacc tccaacacca ccggcaatcc tgaactgacc   780
agccagatgg aaaccttcca cagcacctcc agcgaggca accatctcc tagtcaggtg    840 tccaccacaa gcgagtaccc tagccagcca agcagccctc taacacacc tagacagtag   900
```

<210> SEQ ID NO 15
<211> LENGTH: 138
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 15

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Phe Ile Ile Ser
    50                  55                  60

Ala Asn His Lys Val Thr Leu Thr Val Thr Val Gln Thr Ile Lys
65                  70                  75                  80

Asn His Thr Glu Lys Asn Pro Pro Lys Lys Pro Lys Asp Asp Tyr His
                85                  90                  95
```

```
Phe Glu Val Phe Asn Phe Val Pro Cys Ser Ile Cys Gly Asn Asn Gln
                100                 105                 110

Leu Cys Lys Ser Ile Cys Lys Thr Ile Pro Ser Asn Lys Pro Lys Lys
        115                 120                 125

Lys Pro Thr Ile Lys Pro Thr Asn Lys Pro
    130                 135
```

<210> SEQ ID NO 16
<211> LENGTH: 417
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 16

```
atgtccaaac acaagaatca acgcactgcc aggactctag aaaagacctg ggatactctc    60
aatcatctaa ttgtaatatc ctcttgttta tacagattaa atttaaaatc tatagcacaa   120
atagcactat cagttctggc aatgataatc tcaacctctc tcataattgc agccataata   180
ttcatcatct ctgccaatca caaagttaca ctaacaacgg tcacagttca acaataaaa    240
aaccacactg aaaaaaaccc accaaaaaaa ccaaaagatg attaccattt tgaagtgttc   300
aacttcgttc cctgtagtat atgtggcaac aatcaacttt gcaaatccat ctgtaaaaca   360
ataccaagca caaaccaaa gaagaaacca accatcaaac ccacaaacaa accatag     417
```

<210> SEQ ID NO 17
<211> LENGTH: 138
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 17

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Ile
        35                  40                  45

Val Ile Ser Thr Ser Leu Ile Ile Ala Ala Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Pro Pro Lys Lys Pro Lys Asp Asp Tyr His
                85                  90                  95

Phe Glu Val Phe Asn Phe Val Pro Cys Ser Ile Cys Gly Asn Asn Gln
                100                 105                 110

Leu Cys Lys Ser Ile Cys Lys Thr Ile Pro Ser Asn Lys Pro Lys Lys
        115                 120                 125

Lys Pro Thr Ile Lys Pro Thr Asn Lys Pro
    130                 135
```

<210> SEQ ID NO 18
<211> LENGTH: 417
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 18

```
atgtccaaac acaagaatca acgcactgcc aggactctag aaaagacctg ggatactctc    60
aatcatctaa ttgtaatatc ctcttgttta tacagattaa atttaaaatc tatagcacaa   120
atagcactat cagttctggc aatcgtgatc tcaacctctc tcataattgc agccataata   180
ttcatcatct ctgccaatca caaagttaca ctaacaacgg tcacagttca acaataaaa   240
aaccacactg aaaaaaaccc accaaaaaaa ccaaagatg attaccattt tgaagtgttc    300
aacttcgttc cctgtagtat atgtggcaac aatcaacttt gcaaatccat ctgtaaaaca   360
ataccaagca caaaccaaa gaagaaacca accatcaaac ccacaaacaa accatag      417
```

<210> SEQ ID NO 19
<211> LENGTH: 299
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 19

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
        115                 120                 125

Thr Thr Ala Gln Thr Lys Gly Arg Thr Thr Thr Ser Thr Gln Thr Asn
    130                 135                 140

Lys Pro Ser Thr Lys Pro Arg Leu Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Pro Ala Lys Thr Thr Lys
    210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
            260                 265                 270

Asn Thr Pro Asn Ser Thr Gln Thr Pro Thr Ala Ser Glu Pro Ser Thr
        275                 280                 285
```

Ser Asn Ser Thr Gln Asn Thr Gln Ser His Ala
    290                 295

<210> SEQ ID NO 20
<211> LENGTH: 900
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 20

```
atgtccaaac acaagaatca acgcactgcc aggactctag aaaagacctg ggatactctc    60
aatcatctaa ttgtaatatc ctcttgttta tacagattaa atttaaaatc tatagcacaa   120
atagcactat cagttctggc aatgataatc tcaacctctc tcataattgc agccataata   180
ttcatcatct ctgccaatca caaagttaca ctaacaacgg tcacagttca acaataaaa    240
aaccacactg aaaaaaacat caccacctac cttactcaag tcccaccaga aagggttagc   300
tcatccaaac aacctacaac cacatcacca atccacacaa ttcagccac aacatcaccc    360
aacacaaagt cagaaacaca ccacacaaca gcacaaacca aaggcagaaac caccacctca   420
acacagacca caagccgag cacaaaacca cgcctaaaaa atccaccaaa aaaccaaaa    480
gatgattacc attttgaagt gttcaacttc gttccctgta gtatatgtgg caacaatcaa   540
ctttgcaaat ccatctgtaa aacaatacca agcaacaaac caagaagaa accaaccatc    600
aaacccacaa acaaaccaac caccaaaacc acaaacaaaa gagacccaaa acaccagcc    660
aaaacgacga aaaagaaac taccaccaac ccaacaaaaa aaccaaccct cacgaccaca   720
gaaagagaca ccagcaccts acaatccact gtgctcgaca caaccacatt agaacacaca   780
atccaacagc aatccctcca ctcaaccacc ccgaaaaca cccaactc cacacaaaca   840
cccacagcat ccgagccctc tacatcaaat tccacccaaa atacccaatc acatgcttag   900
```

<210> SEQ ID NO 21
<211> LENGTH: 299
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 21

Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Ile
        35                  40                  45

Val Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Ser Pro Ile His
            100                 105                 110

Thr Asn Ser Ala Thr Thr Ser Pro Asn Thr Lys Ser Glu Thr His His
        115                 120                 125

Thr Thr Ala Gln Thr Lys Gly Arg Thr Thr Thr Ser Thr Gln Thr Asn

```
                    130                 135                 140
Lys Pro Ser Thr Lys Pro Arg Leu Lys Asn Pro Pro Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
                180                 185                 190

Lys Pro Lys Lys Pro Thr Ile Lys Pro Thr Asn Lys Pro Thr Thr
            195                 200                 205

Lys Thr Thr Asn Lys Arg Asp Pro Lys Thr Pro Ala Lys Thr Thr Lys
            210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
                260                 265                 270

Asn Thr Pro Asn Ser Thr Gln Thr Pro Thr Ala Ser Glu Pro Ser Thr
            275                 280                 285

Ser Asn Ser Thr Gln Asn Thr Gln Ser His Ala
        290                 295

<210> SEQ ID NO 22
<211> LENGTH: 900
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 22
atgtccaaac acaagaatca acgcactgcc aggactctag aaaagacctg ggatactctc      60
aatcatctaa ttgtaatatc ctcttgttta tacagattaa atttaaaatc tatagcacaa     120
atagcactat cagttctggc aatcgtgatc tcaacctctc tcataattgc agccataata     180
ttcatcatct ctgccaatca caaagttaca ctaacaacgg tcacagttca acaataaaa      240 aaccacactg aaaaaaacat caccacctac cttactcaag tcccaccaga aagggttagc     300
tcatccaaac aacctacaac cacatcacca atccacacaa attcagccac aacatcaccc     360
aacacaaagt cagaaacaca ccacacaaca gcacaaacca aaggcagaac caccacctca     420
acacagacca caagccgag cacaaaacca cgcctaaaaa atccaccaaa aaaaccaaaa      480
gatgattacc attttgaagt gttcaacttc gttccctgta gtatatgtgg caacaatcaa     540
ctttgcaaat ccatctgtaa aacaatacca agcaacaaac caagaagaa accaaccatc      600 aaacccacaa acaaaccaac caccaaaacc acaaacaaaa gagacccaaa acaccagcc     660 aaaacgacga aaaagaaac taccaccaac ccaacaaaaa aaccacccct cacgaccaca     720
gaaagagaca ccagcacctc acaatccact gtgctcgaca caaccacatt agaacacaca     780
atccaacagc aatccctcca ctcaaccacc ccgaaaaaca cccaactc cacaaacaca      840 cccacagcat ccgagccctc tacatcaaat tccacccaaa atacccaatc acatgcttag     900

<210> SEQ ID NO 23
<211> LENGTH: 574
<212> TYPE: PRT
<213> ORGANISM: ARTIFICIAL SEQUENCE
<220> FEATURE:
<223> OTHER INFORMATION: SYNTHETIC CONSTRUCT
```

<400> SEQUENCE: 23

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys

|     | 405 |     |     |     | 410 |     |     |     | 415 |     |     |
| --- | --- | --- | --- | --- | --- | --- | --- | --- | --- | --- | --- |

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 24
<211> LENGTH: 1812
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 24

```
cggaaggccc atgaggccag ttaattaaga ggtaccggat ccgccaccat ggaactgctg      60
atcctgaagg ccaacgccat caccaccatc ctgaccgctg tgaccttctg cttcgccagc     120
ggccagaaca tcaccgagga attctaccag agcacctgta gcgccgtgtc aagggctac     180
ctgagcgccc tgcggaccgg ctggtacacc agcgtgatca ccatcgagct gagcaacatc     240
aagaaaaaca gtgcaacgg caccgacgcc aagatcaagc tgatcaagca ggaactggac     300
aagtacaaga cgccgtgac cgagctgcag ctgctgatgc agagcacccc cgccaccaac     360
aaccgggcta cgcgagct gcctcggttc atgaactaca ccctgaacaa cgccaaaaag     420
accaacgtga ccctgagcaa gaagcggaag cggcggttcc tgggcttcct gctgggcgtg     480
ggcagcgcca ttgctagcgg agtggccgtg tgcaaggtgc tgcacctgga aggcgaagtg     540
aacaagatca gtccgccct gctgagcacc aacaaggccg tggtgtccct gagcaacggc     600
gtgtccgtgc tgaccttcaa ggtgctggat ctgaagaact acatcgacaa gcagctgctg     660
cccatcctga caagcagag ctgcagcatc agcaacatcg agacagtgat cgagttccag     720
cagaagaaca ccggctgct ggaaatcacc cgcgagttca gcgtgaacgc cggcgtgacc     780
acccccgtgt ccacctacat gctgaccaac agcgagctgc tgagcctgat caacgacatg     840
cccatcacca cgaccagaa aaagctgatg agcaacaacg tgcagatcgt gcggcagcag     900
agctactcca tcatgtgcat catcaaagaa gaggtgctgg cctacgtggt gcagctgccc     960
ctgtacggcg tgatcgacac ccccctgctgg aagctgcaca ccagccccct gtgcaccacc    1020
aacaccaaag agggcagcaa catctgcctg accggaccg accggggctg gtactgcgat    1080
aatgccggca gcgtgtcatt ctttccacaa gccgagacat gcaaggtgca gagcaaccgg    1140
```

| | |
|---|---|
| gtgttctgcg acaccatgaa cagcctgacc ctgccctccg aagtgaacct gtgcaacgtg | 1200 |
| gacatcttca accctaagta cgactgcaag atcatgacct ccaagaccga cgtgtccagc | 1260 |
| tccgtgatca cctccctggg cgccatcgtg tcctgctacg gcaagaccaa gtgcaccgcc | 1320 |
| agcaacaaga accggggcat catcaagacc ttcagcaacg gctgcgacta cgtgtccaac | 1380 |
| aaggggqtgg acaccgtgtc cgtgggcaac accctgtact acgtgaacaa acaggaaggc | 1440 |
| aagagcctgt acgtgaaggg cgagcccatc atcaacttct acgaccccct ggtgttcccc | 1500 |
| agcgacgagt tcgacgccag catcagccag gtcaacgaga agatcaacca gagcctggcc | 1560 |
| ttcatcagaa agagcgacga gctgctgcac aatgtgaatg ccgtgaagtc caccaccaat | 1620 |
| atcatgatca ccacaatcat catcgtgatc atcgtcatcc tgctgtccct gatcgccgtg | 1680 |
| ggcctgctgc tgtactgcaa ggcccggtcc acccctgtga ccctgtccaa ggaccagctg | 1740 |
| agcggcatca acaatatcgc cttctccaac tgactcgagc tcatggcgcg cctaggcctt | 1800 |
| gacggccttc cg | 1812 |

```
<210> SEQ ID NO 25
<211> LENGTH: 1725
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 25
```

| | |
|---|---|
| atggaactgc tgatcctgaa ggccaacgcc atcaccacca tcctgaccgc tgtgaccttc | 60 |
| tgcttcgcca gcgccagaa catcaccgag gaattctacc agagcacctg tagcgccgtg | 120 |
| tccaagggct acctgagcgc cctgcggacc ggctggtaca ccagcgtgat caccatcgag | 180 |
| ctgagcaaca tcaagaaaaa caagtgcaac ggcaccgacg ccaagatcaa gctgatcaag | 240 |
| caggaactgg acaagtacaa gaacgccgtg accgagctgc agctgctgat gcagagcacc | 300 |
| cccgccacca acaaccgggc tagacgcgag ctgcctcggt tcatgaacta cacccctgaac | 360 |
| aacgccaaaa agaccaacgt gaccctgagc aagaagcgga agcggcggtt cctgggcttc | 420 |
| ctgctgggcg tgggcagcgc cattgctagc ggagtggccc tgtgcaaggt gctgcacctg | 480 |
| gaaggcgaag tgaacaagat caagtccgcc ctgctgagca ccaacaaggc cgtggtgtcc | 540 |
| ctgagcaacg gcgtgtccgt gctgaccttc aaggtgctgg atctgaagaa ctacatcgac | 600 |
| aagcagctgc tgcccatcct gaacaagcag agctgcagca tcagcaacat cgagacagtg | 660 |
| atcgagttcc agcagaagaa caccggctg ctggaaatca cccgcgagtt cagcgtgaac | 720 |
| gccggcgtga ccaccccgt gtccacctac atgctgacca acagcgagct gctgagcctg | 780 |
| atcaacgaca tgcccatcac caacgaccag aaaaagctga tgagcaacaa cgtgcagatc | 840 |
| gtgcggcagc agagctactc catcatgtgc atcatcaaag aagaggtgct ggcctacgtg | 900 |
| gtgcagctgc ccctgtacgg cgtgatcgac acccctgct ggaagctgca caccagcccc | 960 |
| ctgtgcacca ccaacaccaa agagggcagc aacatctgcc tgacccggac cgaccggggc | 1020 |
| tggtactgcg ataatgccgg cagcgtgtca ttctttccac aagccgagac atgcaaggtg | 1080 |
| cagagcaacc gggtgttctg cgacaccatg aacagcctga ccctgcccte gaagtgaac | 1140 |
| ctgtgcaacg tggacatctt caaccctaag tacgactgca agatcatgac ctccaagacc | 1200 |
| gacgtgtcca gctccgtgat cacctccctg ggcgccatcg tgtcctgcta cggcaagacc | 1260 |
| aagtgcaccg ccagcaacaa gaaccggggc atcatcaaga ccttcagcaa cggctgcgac | 1320 |

```
tacgtgtcca caaggggt ggacaccgtg tccgtgggca acaccctgta ctacgtgaac    1380
aaacaggaag gcaagagcct gtacgtgaag ggcgagccca tcatcaactt ctacgacccc    1440
ctggtgttcc ccagcgacga gttcgacgcc agcatcagcc aggtcaacga aagatcaac    1500 cagagcctgg ccttcatcag aaagagcgac gagctgctgc acaatgtgaa tgccgtgaag    1560
tccaccacca atatcatgat caccacaatc atcatcgtga tcatcgtcat cctgctgtcc    1620
ctgatcgccg tgggcctgct gctgtactgc aaggcccggt ccaccctgt gaccctgtcc     1680 aaggaccagc tgagcggcat caacaatatc gccttctcca actga                    1725
```

<210> SEQ ID NO 26
<211> LENGTH: 552
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 26

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
```

```
                        290                 295                 300
Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Val Lys Ser Thr Thr Asn Ile Met Ile Thr Thr Ile Ile Ile Val Ile
            500                 505                 510

Ile Val Ile Leu Leu Ser Leu Ile Ala Val Gly Leu Leu Leu Tyr Cys
        515                 520                 525

Lys Ala Arg Ser Thr Pro Val Thr Leu Ser Lys Asp Gln Leu Ser Gly
    530                 535                 540

Ile Asn Asn Ile Ala Phe Ser Asn
545                 550

<210> SEQ ID NO 27
<211> LENGTH: 1746
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 27
cggaaggccc atgaggccag ttaattaaga ggtaccggat ccgccaccat ggaactgctg      60
atcctgaagg ccaacgccat caccaccatc ctgaccgctg tgaccttctg cttcgccagc     120
ggccagaaca tcaccgagga attctaccag agcacctgta gcgccgtgtc aagggctac     180 ctgagcgccc tgcggaccgg ctggtacacc agcgtgatca ccatcgagct gagcaacatc     240
aagaaaatca gtgcaacgg caccgacgcc aagatcaagc tgatcaagca ggaactggac     300
aagtacaaga cgccgtgac cgagctgcag ctgctgatgc agagcacccc cgccaccaac     360
aaccaggcta gaggcagcgg aagcggacgg tccctgggct tcctgctggg cgtgggcagc     420
gccattgcta gcggagtggc cgtgtcaaag gtgctgcacc tggaaggcga agtgaacaag     480
atcaagtccg ccctgctgag caccaacaag gccgtggtgt ccctgagcaa cggcgtgtcc     540
gtgctgacca gcaaggtgct ggatctgaag aactacatcg acaagcagct gctgcccatc     600
```

```
gtgaacaagc agagctgcag catccccaac atcgagacag tgatcgagtt ccagcagaag      660
aacaaccggc tgctggaaat cacccgcgag ttcagcgtga acgccggcgt gaccacccc       720 gtgtccacct acatgctgac caacagcgag ctgctgagcc tgatcaacga catgcccatc     780
accaacgacc agaaaaagct gatgagcaac aacgtgcaga tcgtgcggca gcagagctac     840
tccatcatga gcatcatcaa gaagaggtg ctggcctacg tggtgcagct gcccctgtac      900
ggcgtgatcg acacccctg ctggaagctg cacaccagcc cctgtgcac caccaacacc       960 aaagagggca gcaacatctg cctgacccgg accgaccggg gctggtactg cgataatgcc    1020
ggcagcgtgt cattctttcc acaagccgag acatgcaagg tgcagagcaa ccgggtgttc    1080
tgcgacacca tgaacagcct gaccctgccc tccgaagtga acctgtgcaa cgtggacatc    1140
ttcaacccta gtacgactg caagatcatg acctccaaga ccgacgtgtc cagctccgtg     1200
atcacctccc tgggcgccat cgtgtcctgc tacggcaaga ccaagtgcac cgccagcaac    1260
aagaaccggg gcatcatcaa gaccttcagc aacggctgcg actacgtgtc caacaagggg    1320
gtggacaccg tgtccgtggg caacacccctg tactacgtga caaacagga aggcaagagc   1380 ctgtacgtga agggcgagcc catcatcaac ttctacgacc ccctggtgtt ccccagcgac    1440
gagttcgacg ccagcatcag ccaggtcaac gagaagatca ccagagcct ggccttcatc     1500 agaaagagcg acgagctgct gcacaatgtg aatgccgtga agtccaccac caatatcatg    1560
atcaccacaa tcatcatcgt gatcatcgtc atcctgctgt ccctgatcgc cgtgggcctg    1620
ctgctgtact gcaaggcccg gtccaccccct gtgaccctgt ccaaggacca gctgagcggc    1680
atcaacaata tcgccttctc caactgactc gagctcatgg cgcgcctagg ccttgacggc    1740
cttccg                                                               1746

<210> SEQ ID NO 28
<211> LENGTH: 1659
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 28
atggaactgc tgatcctgaa ggccaacgcc atcaccacca tcctgaccgc tgtgaccttc      60
tgcttcgcca gcggccagaa catcaccgag gaattctacc agagcacctg tagcgccgtg    120
tccaagggct acctgagcgc cctgcggacc ggctggtaca ccagcgtgat caccatcgag    180
ctgagcaaca tcaagaaaat caagtgcaac ggcaccgacg ccaagatcaa gctgatcaag    240
caggaactgg acaagtacaa gaacgccgtg accgagctgc agctgctgat gcagagcacc    300
cccgccacca caaccaggc tagaggcagc ggaagcggac ggtccctggg cttcctgctg     360
ggcgtgggca gcgccattgc tagcggagtg gccgtgtcaa aggtgctgca cctggaaggc    420
gaagtgaaca agatcaagtc cgccctgctg agcaccaaca aggccgtggt gtccctgagc    480
aacggcgtgt ccgtgctgac cagcaaggtg ctggatctga gaactacat cgacaagcag     540 ctgctgccca tcgtgaacaa gcagagctgc agcatcccca catcgagac agtgatcgag    600 ttccagcaga agaacaaccg gctgctggaa atcccccgcg agttcagcgt gaacgccggc    660
gtgaccaccc ccgtgtccac ctacatgctg accaacagcg agctgctgag cctgatcaac    720
gacatgccca tcaccaacga ccagaaaaag ctgatgagca caacgtgca gatcgtgcgg     780 cagcagagct actccatcat gagcatcatc aaagaagagg tgctggccta cgtggtgcag    840
```

```
ctgcccctgt acggcgtgat cgacaccccc tgctggaagc tgcacaccag cccctgtgc    900 accaccaaca ccaaagaggg cagcaacatc tgcctgaccc ggaccgaccg gggctggtac    960
tgcgataatg ccggcagcgt gtcattcttt ccacaagccg agacatgcaa ggtgcagagc    1020
aaccgggtgt ctgcgacac catgaacagc ctgaccctgc cctccgaagt gaacctgtgc    1080
aacgtggaca tcttcaaccc taagtacgac tgcaagatca tgacctccaa gaccgacgtg    1140
tccagctccg tgatcacctc cctgggcgcc atcgtgtcct gctacggcaa gaccaagtgc    1200
accgccagca acaagaaccg gggcatcatc aagaccttca gcaacggctg cgactacgtg    1260
tccaacaagg gggtggacac cgtgtccgtg ggcaacaccc tgtactacgt gaacaaacag    1320
gaaggcaaga gcctgtacgt gaagggcgag cccatcatca acttctacga ccccctggtg    1380
ttccccagcg acgagttcga cgccagcatc agccaggtca cgagaagat caaccagagc    1440 ctggccttca tcagaaagag cgacgagctg ctgcacaatg tgaatgccgt gaagtccacc    1500
accaatatca tgatcaccac aatcatcatc gtgatcatcg tcatcctgct gtccctgatc    1560
gccgtgggcc tgctgctgta ctgcaaggcc cggtccaccc tgtgaccct gtccaaggac    1620 cagctgagcg gcatcaacaa tatcgccttc tccaactga    1659
```

<210> SEQ ID NO 29
<211> LENGTH: 552
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 29

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220
```

-continued

```
Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
        260                 265                 270

Glu Val Leu Ala Tyr Val Val Gln Leu Pro Leu Tyr Gly Val Ile Asp
    275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
            325                 330                 335

Lys Val Gln Ser Asn Arg Val Phe Cys Asp Thr Met Asn Ser Leu Thr
        340                 345                 350

Leu Pro Ser Glu Val Asn Leu Cys Asn Val Asp Ile Phe Asn Pro Lys
    355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
        420                 425                 430

Thr Leu Tyr Tyr Val Asn Lys Gln Glu Gly Lys Ser Leu Tyr Val Lys
    435                 440                 445

Gly Glu Pro Ile Ile Asn Phe Tyr Asp Pro Leu Val Phe Pro Ser Asp
450                 455                 460

Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
            485                 490                 495

Val Lys Ser Thr Thr Asn Ile Met Ile Thr Thr Ile Ile Ile Val Ile
        500                 505                 510

Ile Val Ile Leu Leu Ser Leu Ile Ala Val Gly Leu Leu Leu Tyr Cys
    515                 520                 525

Lys Ala Arg Ser Thr Pro Val Thr Leu Ser Lys Asp Gln Leu Ser Gly
530                 535                 540

Ile Asn Asn Ile Ala Phe Ser Asn
545                 550

<210> SEQ ID NO 30
<211> LENGTH: 1746
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 30
cggaaggccc atgaggccag ttaattaaga ggtaccggat ccgccaccat ggaactgctg      60
atcctgaagg ccaacgccat caccaccatc ctgaccgctg tgaccttctg cttcgccagc     120
ggccagaaca tcaccgagga attctaccag agcacctgta gcgccgtgtc caagggctac    180
```

```
ctgagcgccc tgcggaccgg ctggtacacc agcgtgatca ccatcgagct gagcaacatc      240
aagaaaatca agtgcaacgg caccgacgcc aagatcaagc tgatcaagca ggaactggac      300
aagtacaaga acgccgtgac cgagctgcag ctgctgatgc agagcacccc cgccaccaac      360
aaccaggcta gaggcagcgg aagcggacgg tccctgggct tcctgctggg cgtgggcagc      420
gccattgcta gcggagtggc cgtgtcaaag gtgctgcacc tggaaggcga agtgaacaag      480
atcaagtccg ccctgctgag caccaacaag gccgtggtgt ccctgagcaa cggcgtgtcc      540
gtgctgacca gcaaggtgct ggatctgaag aactacatcg acaagcagct gctgcccatc      600
gtgaacaagc agagctgcag catccccaac atcgagacag tgatcgagtt ccagcagaag      660
aacaaccggc tgctggaaat cacccgcgag ttcagcgtga acgccggcgt gaccaccccc      720
gtgtccacct acatgctgac caacagcgag ctgctgagcc tgatcaacga catgcccatc      780
accaacgacc agaaaaagct gatgagcaac aacgtgcaga tcgtgcggca gcagagctac      840
tccatcatga gcatcatcaa gaagaggtg ctggcctacg tggtgcagct gccectgtac       900 ggcgtgatcg acaccccctg ctggaagctg cacaccagcc cctgtgcac caccaacacc       960 aaagagggca gcaacatctg cctgacccgg accgaccggg ctggtactg cgataatgcc      1020 ggcagcgtgt cattctttcc acaagccgag acatgcaagg tgcagagcaa ccgggtgttc      1080
tgcgacacca tgaacagcct gacccctgccc tccgaagtga acctgtgcaa cgtggacatc      1140
ttcaaccctc agtacgactg caagatcatg acctccaaga ccgacgtgtc cagctccgtg      1200
atcacctccc tgggcgccat cgtgtcctgc tacggcaaga ccaagtgcac cgccagcaac      1260
aagaaccggg gcatcatcaa gaccttcagc aacggctgcg actacgtgtc caacaagggg      1320
gtggacaccg tgtccgtggg caacacccctg tactacgtga acaaacagga aggcaagagc      1380
ctgtacgtga agggcgagcc catcatcaac ttctacgacc cctggtgtt ccccagcgac      1440 cagttcgacg ccagcatcag ccaggtcaac gagaagatca ccagagcct ggccttcatc      1500 agaaagagcg acgagctgct gcacaatgtg aatgccgtga agtccaccac caatatcatg      1560
atcaccacaa tcatcatcgt gatcatcgtc atcctgctgt ccctgatcgc cgtgggcctg      1620
ctgctgtact gcaaggcccg gtccacccct gtgaccctgt ccaaggacca gctgagcggc      1680
atcaacaata tcgccttctc caactgactc gagctcatgg cgcgcctagg ccttgacggc      1740
cttccg                                                                1746
```

<210> SEQ ID NO 31
<211> LENGTH: 1659
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 31

```
atggaactgc tgatcctgaa ggccaacgcc atcaccacca tcctgaccgc tgtgaccttc       60
tgcttcgcca gcggccagaa catcaccgag gaattctacc agagcacctg tagcgccgtg      120
tccaagggct acctgagcgc cctgcggacc ggctggtaca ccagcgtgat caccatcgag      180
ctgagcaaca tcaagaaaat caagtgcaac ggcaccgacg ccaagatcaa gctgatcaag      240
caggaactgg acaagtacaa gaacgccgtg accgagctgc agctgctgat gcagagcacc      300
cccgccacca caaccaggc tagaggcagc ggaagcggac ggtccctggg cttcctgctg       360
ggcgtgggca gcgccattgc tagcggagtg gccgtgtcaa aggtgctgca cctggaaggc      420
```

```
gaagtgaaca agatcaagtc cgccctgctg agcaccaaca aggccgtggt gtccctgagc      480
aacggcgtgt ccgtgctgac cagcaaggtg ctggatctga agaactacat cgacaagcag      540
ctgctgccca tcgtgaacaa gcagagctgc agcatcccca catcgagac agtgatcgag       600 ttccagcaga gaacaaccg gctgctggaa atcacccgcg agttcagcgt gaacgccggc       660
gtgaccaccc ccgtgtccac ctacatgctg accaacagcg agctgctgag cctgatcaac      720
gacatgccca tcaccaacga ccagaaaaag ctgatgagca caacgtgca gatcgtgcgg       780 cagcagagct actccatcat gagcatcatc aaagaagagg tgctggccta cgtggtgcag      840
ctgcccctgt acggcgtgat cgacaccccc tgctggaagc tgcacaccag ccccctgtgc      900
accaccaaca ccaaagaggg cagcaacatc tgcctgaccc ggaccgaccg gggctggtac      960
tgcgataatg ccggcagcgt gtcattcttt ccacaagccg agacatgcaa ggtgcagagc     1020
aaccgggtgt ctgcgacac catgaacagc ctgaccctgc cctccgaagt gaacctgtgc      1080
aacgtggaca tcttcaaccc taagtacgac tgcaagatca tgacctccaa gaccgacgtg    1140
tccagctccg tgatcacctc cctgggcgcc atcgtgtcct gctacggcaa gaccaagtgc    1200
accgccagca acaagaaccg gggcatcatc aagaccttca gcaacggctg cgactacgtg   1260
tccaacaagg gggtggacac cgtgtccgtg gcaacaccc tgtactacgt gaacaaacag    1320
gaaggcaaga gcctgtacgt gaagggcgag cccatcatca acttctacga ccccctggtg    1380
ttccccagcg accagttcga cgccagcatc agccaggtca cgagaagat caaccagagc    1440 ctggccttca tcagaaagag cgacgagctg ctgcacaatg tgaatgccgt gaagtccacc    1500
accaatatca tgatcaccac aatcatcatc gtgatcatcg tcatcctgct gtccctgatc    1560
gccgtgggcc tgctgctgta ctgcaaggcc cggtccaccc ctgtgaccct gtccaaggac   1620
cagctgagcg gcatcaacaa tatcgccttc tccaactga                          1659
```

<210> SEQ ID NO 32
<211> LENGTH: 114
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 32

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Asn Glu Lys Ile Asn Gln Ser Leu Ala Phe Ile Arg Lys
            35                  40                  45

Ser Asp Glu Leu Leu His Asn Val Asn Ala Val Lys Ser Thr Thr Asn
        50                  55                  60

Ile Met Ile Thr Thr Ile Ile Ile Val Ile Ile Val Ile Leu Leu Ser
65                  70                  75                  80

Leu Ile Ala Val Gly Leu Leu Leu Tyr Cys Lys Ala Arg Ser Thr Pro
                85                  90                  95

Val Thr Leu Ser Lys Asp Gln Leu Ser Gly Ile Asn Asn Ile Ala Phe
                100                 105                 110

Ser Asn
```

<210> SEQ ID NO 33
<211> LENGTH: 345
<212> TYPE: DNA

<213> ORGANISM: ARTIFICIAL SEQUENCE
<220> FEATURE:
<223> OTHER INFORMATION: SYNTHETIC CONSTRUCT

<400> SEQUENCE: 33

```
atggaactgc tgatcctgaa ggccaacgcc atcaccacca tcctgaccgc tgtgaccttc        60
tgcttcgcca gcggccagaa catcaccgag gaattctacc agagcaacga gaagatcaac       120
cagagcctgg ccttcatcag aaagagcgac gagctgctgc acaatgtgaa tgccgtgaag       180
tccaccacca atatcatgat caccacaatc atcatcgtga tcatcgtcat cctgctgtcc       240
ctgatcgccg tgggcctgct gctgtactgc aaggcccggt ccaccccgt gaccctgtcc        300 aaggaccagc tgagcggcat caacaatatc gccttctcca actga                       345
```

<210> SEQ ID NO 34
<211> LENGTH: 574
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 34

```
Met Glu Leu Pro Ile Leu Lys Thr Asn Ala Ile Thr Ala Ile Leu Ala
1               5                  10                  15

Ala Val Thr Leu Cys Phe Ala Ser Ser Gln Asn Ile Thr Glu Glu Phe
            20                  25                  30

Tyr Gln Thr Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Asn Asn Val Gln Ile Val Arg Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Leu Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Ile
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 35
<211> LENGTH: 2142
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 35

```
atggagttgc caatcctcaa aacaaatgca attaccgcaa tccttgctgc agtcacactc      60
tgttttgctt ccagtcaaaa catcactgaa gaattttatc aaacaacatg cagtgcagtc     120
agcaaaggct atcttagtgc tctaagaact ggttggtata ctagtgttat aactatagaa     180
ttaagtaata tcaaggaaaa taagtgtaat ggaacagacg ctaaggtaaa attgataaaa     240
caagaattag ataaatataa aagtgctgta acagaattgc agttgctcat gcaaagcaca     300
ccggcaacca caatcgagc cagaagagaa ctaccaaggt ttatgaatta tacactcaac     360
```

-continued

```
aataccaaaa ataccaatgt aacattaagc aagaaaagga aaagaagatt tcttggcttt    420
ttgttaggtg ttggatctgc aatcgccagt ggcattgctg tatctaaggt cctgcaccta    480 gaagggaag tgaacaaaat caaaagtgct ctactatcca caaacaaggc tgtagtcagc    540
ttatcaaatg gagttagtgt cttaaccagc aaagtgttag acctcaaaaa ctatatagat    600
aaacagttgt tacctattgt gaacaagcaa agctgtagca tatcaaacat tgaaactgtg    660
atagagttcc aacaaaagaa caacagacta ctagagatta ccaggaatt tagtgttaat     720 gcaggtgtaa ctacacctgt aagcacttat atgttaacaa atagtgaatt attatcatta    780
atcaatgata tgcctataac aaatgatcag aaaaagttaa tgtccaacaa tgttcaaata    840
gttagacagc aaagttactc tatcatgtcc ataataaagg aggaagtctt agcatatgta    900
gtacaattac cactatatgg tgtaatagat acaccttgtt ggaaactgca cacatcccct    960
ctatgtacaa ccaacacaaa ggaagggtcc aacatctgtt aacaagaac cgacagagga    1020 tggtactgtg acaatgcagg atcagtatct ttcttcccac tagctgaaac atgtaaagtt   1080
caatcgaatc gagtattttg tgacacaatg aacagtttaa cattaccaag tgaagtaaat   1140
ctctgcaaca ttgacatatt caaccccaaa tatgattgca aaattatgac ttcaaaaaca   1200
gatgtaagca gctccgttat cacatctcta ggagccattg tgtcatgcta tggcaaaact   1260
aaatgtacag catccaataa aaatcgtgga atcataaaga catttttctaa cgggtgcgat  1320 tatgtatcaa ataaggggt tgacactgtg tctgtaggta atacattata ttatgtaaat    1380
aagcaagaag gcaaaagtct ctatgtaaaa ggtgaaccaa taataaattt ctatgaccca   1440
ttagtgttcc cctctgatga atttgatgca tcaatatctc aagtcaatga gaagattaac   1500
cagagcctag catttattcg taaatccgat gaattattac ataatgtaaa tgctggtaaa   1560
tccaccataa atatcatgat aactactata attatagtga ttatagtaat attgttatca   1620
ttaattgccg ttggactgct ccctatactgc aaggccagaa gcacaccagt cacactaagc  1680
aaggatcaac tgagtggtat aaataatatt gcatttagta actaaaacgg gtgcgattat   1740
gtatcaaata aggggttga cactgtgtct gtaggtaata cattatatta tgtaaataag    1800
caagaaggca aaagtctcta tgtaaaaggt gaaccaataa taaatttcta tgacccatta   1860
gtgttcccct ctgatgaatt tgatgcatca atatctcaag tcaatgagaa gattaaccag   1920
agcctagcat ttattcgtaa atccgatgaa ttattacata atgtaaatgc tggtaaatcc   1980
accataaata tcatgataac tactataatt atagtgatta gtaatatatt gttatcatta   2040
attgccgttg gactgctcct atactgcaag gccagaagca caccagtcac actaagcaag   2100
gatcaactga gtggtataaa taatattgca tttagtaact aa                      2142
```

<210> SEQ ID NO 36
<211> LENGTH: 574
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 36

```
Met Glu Leu Pro Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
                20                  25                  30

Tyr Gln Thr Thr Cys Ser Ala Val Ser Lys Gly Tyr Leu Ser Ala Leu
            35                  40                  45
```

-continued

```
Arg Thr Gly Trp Tyr Thr Ser Val Ile Thr Ile Glu Leu Ser Asn Ile
     50                      55                      60

Lys Glu Asn Lys Cys Asn Gly Thr Asp Ala Lys Val Lys Leu Ile Lys
 65                      70                      75                  80

Gln Glu Leu Asp Lys Tyr Lys Ser Ala Val Thr Glu Leu Gln Leu Leu
                     85                      90                      95

Met Gln Ser Thr Pro Ala Thr Asn Asn Arg Ala Arg Arg Glu Leu Pro
                100                     105                     110

Arg Phe Met Asn Tyr Thr Leu Asn Asn Thr Lys Asn Thr Asn Val Thr
             115                     120                     125

Leu Ser Lys Lys Arg Lys Arg Arg Phe Leu Gly Phe Leu Leu Gly Val
 130                     135                     140

Gly Ser Ala Ile Ala Ser Gly Ile Ala Val Ser Lys Val Leu His Leu
 145                     150                     155                 160

Glu Gly Glu Val Asn Lys Ile Lys Ser Ala Leu Leu Ser Thr Asn Lys
                 165                     170                     175

Ala Val Val Ser Leu Ser Asn Gly Val Ser Val Leu Thr Ser Lys Val
                 180                     185                     190

Leu Asp Leu Lys Asn Tyr Ile Asp Lys Gln Leu Leu Pro Ile Val Asn
                 195                     200                     205

Lys Gln Ser Cys Ser Ile Ser Asn Ile Glu Thr Val Ile Glu Phe Gln
 210                     215                     220

Gln Lys Asn Asn Arg Leu Leu Glu Ile Thr Arg Glu Phe Ser Val Asn
 225                     230                     235                 240

Ala Gly Val Thr Thr Pro Val Ser Thr Tyr Met Leu Thr Asn Ser Glu
                 245                     250                     255

Leu Leu Ser Leu Ile Asn Asp Met Pro Ile Thr Asn Asp Gln Lys Lys
                 260                     265                     270

Leu Met Ser Asn Asn Val Gln Ile Val Arg Gln Gln Ser Tyr Ser Ile
                 275                     280                     285

Met Ser Ile Ile Lys Glu Val Leu Ala Tyr Val Val Gln Leu Pro
                 290                     295                     300

Leu Tyr Gly Val Ile Asp Thr Pro Cys Trp Lys Leu His Thr Ser Pro
 305                     310                     315                 320

Leu Cys Thr Thr Asn Thr Lys Glu Gly Ser Asn Ile Cys Leu Thr Arg
                 325                     330                     335

Thr Asp Arg Gly Trp Tyr Cys Asp Asn Ala Gly Ser Val Ser Phe Phe
                 340                     345                     350

Pro Leu Ala Glu Thr Cys Lys Val Gln Ser Asn Arg Val Phe Cys Asp
                 355                     360                     365

Thr Met Asn Ser Leu Thr Leu Pro Ser Glu Val Asn Leu Cys Asn Ile
                 370                     375                     380

Asp Ile Phe Asn Pro Lys Tyr Asp Cys Lys Ile Met Thr Ser Lys Thr
 385                     390                     395                 400

Asp Val Ser Ser Ser Val Ile Thr Ser Leu Gly Ala Ile Val Ser Cys
                 405                     410                     415

Tyr Gly Lys Thr Lys Cys Thr Ala Ser Asn Lys Asn Arg Gly Ile Ile
                 420                     425                     430

Lys Thr Phe Ser Asn Gly Cys Asp Tyr Val Ser Asn Lys Gly Val Asp
                 435                     440                     445

Thr Val Ser Val Gly Asn Thr Leu Tyr Val Asn Lys Gln Glu Gly
 450                     455                     460

Lys Ser Leu Tyr Val Lys Gly Glu Pro Ile Ile Asn Phe Tyr Asp Pro
```

```
              465                 470                 475                 480
Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Ile Asn Ile Met Ile Thr
                515                 520                 525

Thr Ile Ile Ile Val Ile Ile Val Ile Leu Ser Leu Ile Ala Val
                530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 37
<211> LENGTH: 574
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 37

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
                50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
                130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
```

```
                     260                 265                 270
Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
            515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 38
<211> LENGTH: 1725
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 38

```
atggaactgc tgatcctgaa ggccaacgcc atcaccacca tcctgaccgc tgtgaccttc      60
tgcttcgcca cggcagaa catcaccgag gaattctacc agagcacctg tagcgccgtg       120
tccaagggct acctgagcgc cctgcggacc ggctggtaca ccagcgtgat caccatcgag     180
ctgagcaaca tcaagaaaaa caagtgcaac ggcaccgacg ccaagatcaa gctgatcaag     240
caggaactgg acaagtacaa gaacgccgtg accgagctgc agctgctgat gcagagcacc     300
```

```
cccgccacca caaccgggc tagacgcgag ctgcctcggt tcatgaacta caccctgaac      360
aacgccaaaa agaccaacgt gaccctgagc aagaagcgga agcggcggtt cctgggcttc      420
ctgctgggcg tgggcagcgc cattgctagc ggagtggccg tgtcaaaggt gctgcacctg      480
gaaggcgaag tgaacaagat caagtccgcc ctgctgagca ccaacaaggc cgtggtgtcc      540
ctgagcaacg gcgtgtccgt gctgaccagc aaggtgctgg atctgaagaa ctacatcgac      600
aagcagctgc tgcccatcgt gaacaagcag agctgcagca tcagcaacat cgagacagtg      660
atcgagttcc agcagaagaa caaccggctg ctggaaatca cccgcgagtt cagcgtgaac      720
gccggcgtga ccaccccgt gtccacctac atgctgacca cagcgagct gctgagcctg      780 atcaacgaca tgcccatcac caacgaccag aaaaagctga tgagcaacaa cgtgcagatc      840
gtgcggcagc agagctactc catcatgagc atcatcaaag aagaggtgct ggcctacgtg      900
gtgcagctgc ccctgtacgg cgtgatcgac acccctgct ggaagctgca caccagcccc      960
ctgtgcacca ccaacaccaa agagggcagc aacatctgcc tgacccggac cgaccggggc     1020
tggtactgcg ataatgccgg cagcgtgtca ttctttccac aagccgagac atgcaaggtg     1080
cagagcaacc gggtgttctg cgacaccatg aacagcctga ccctgccctc cgaagtgaac     1140
ctgtgcaacg tggacatctt caaccctaag tacgactgca agatcatgac ctccaagacc     1200
gacgtgtcca gctccgtgat cacctccctg ggcgccatcg tgtcctgcta cggcaagacc     1260
aagtgcaccg ccagcaacaa gaaccggggc atcatcaaga ccttcagcaa cggctgcgac     1320
tacgtgtcca acaagggggt ggacaccgtg tccgtgggca cacccgtta ctacgtgaac     1380 aaacaggaag caagagcct gtacgtgaag ggcgagccca tcatcaactt ctacgacccc     1440
ctggtgttcc ccagcgacga gttcgacgcc agcatcagcc aggtcaacga gaagatcaac     1500
cagagcctgg ccttcatcag aaagagcgac gagctgctgc acaatgtgaa tgccgtgaag     1560
tccaccacca atatcatgat caccacaatc atcatcgtga tcatcgtcat cctgctgtcc     1620
ctgatcgccg tgggcctgct gctgtactgc aaggcccggt ccaccctgt gaccctgtcc     1680 aaggaccagc tgagcggcat caacaatatc gccttctcca actga                       1725
```

<210> SEQ ID NO 39  
<211> LENGTH: 256  
<212> TYPE: PRT  
<213> ORGANISM: ARTIFICIAL SEQUENCE  
<220> FEATURE:  
<223> OTHER INFORMATION: SYNTHETIC CONSTRUCT

<400> SEQUENCE: 39

```
Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Pro Ala Ser Leu
            20                  25                  30

Thr Ile Trp Val Pro Met Phe Gln Ser Ser Met Pro Ala Asp Leu Leu
        35                  40                  45

Ile Lys Glu Leu Ala Asn Val Asn Ile Leu Val Lys Gln Ile Ser Thr
    50                  55                  60

Pro Asn Gly Pro Ser Leu Arg Val Met Ile Asn Ser Arg Ser Ala Val
65                  70                  75                  80

Leu Ala Gln Met Pro Ser Lys Phe Thr Ile Cys Ala Asn Val Ser Leu
                85                  90                  95

Asp Glu Arg Ser Lys Leu Ala Tyr Asp Val Thr Thr Pro Cys Glu Ile
            100                 105                 110
```

```
Lys Ala Cys Ser Leu Thr Cys Leu Lys Ser Lys Asn Met Leu Thr Thr
            115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Val Ile Thr Val Thr Asp
    195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255

<210> SEQ ID NO 40
<211> LENGTH: 771
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 40
atggaaacat acgtgaacaa acttcacgaa ggctccacat acacagctgc tgttcaatac    60
aatgtcttag aaaagacga tgaccctgca tcacttacaa tatgggtgcc catgttccaa   120
tcatccatgc cagcagattt acttataaaa gaactagcta atgtcaacat actagtgaaa   180
caaatatcca cacccaatgg accttcatta gagtcatga taaactcaag aagtgcagtg   240
ctagcacaaa tgcccagcaa atttaccata tgtgccaatg tgtccttgga tgaaagaagc   300
aagctggcat atgatgtaac cacaccctgt gaaatcaagg catgtagtct aacatgccta   360
aaatcaaaaa atatgttaac tacagttaaa gatctcacta tgaaaacact caacccaaca   420
catgacatca ttgctttatg tgaatttgaa aatatagtaa catcaaaaaa agtcataata   480
ccaacatacc taagatccat cagtgtcaga aataaagatc tgaacacact gaaaatata   540 acaaccactg aattcaaaaa tgccatcaca aatgcaaaaa tcatccctta ctcaggatta   600
ctgttagtca tcacagtgac tgacaacaaa ggagcattca atacataaa gccacaaagt   660 caatttatag tagatcttgg agcttaccta gaaaagaaa gtatatatta tgttacaaca   720
aattggaagc acacagctac acgatttgca atcaaaccca tggaagatta a           771

<210> SEQ ID NO 41
<211> LENGTH: 259
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 41

Met Phe Gln Ser Ser Met Pro Ala Asp Leu Leu Ile Lys Asp Ser Thr
1               5                   10                  15

Tyr Thr Ala Ala Val Gln Tyr Asn Val Leu Glu Lys Asp Asp Pro
            20                  25                  30
```

Ala Ser Leu Thr Ile Trp Val Pro Met Phe Gln Ser Ser Met Pro Ala
         35                  40                  45

Asp Leu Leu Ile Lys Glu Leu Ala Asn Val Asn Ile Leu Val Lys Gln
 50                  55                  60

Ile Ser Thr Pro Lys Gly Pro Ser Leu Arg Val Met Ile Asn Ser Arg
 65                  70                  75                  80

Ser Ala Val Leu Ala Gln Met Pro Ser Lys Phe Thr Ile Cys Ala Asn
                 85                  90                  95

Val Ser Leu Asp Glu Arg Ser Lys Leu Ala Tyr Asp Val Thr Thr Pro
                100                 105                 110

Cys Glu Ile Lys Ala Cys Ser Leu Thr Cys Leu Lys Ser Lys Asn Met
                115                 120                 125

Leu Thr Thr Val Lys Asp Leu Thr Met Lys Thr Leu Asn Pro Thr His
        130                 135                 140

Asp Ile Ile Ala Leu Cys Glu Phe Glu Asn Ile Val Thr Ser Lys Lys
145                 150                 155                 160

Val Ile Ile Pro Thr Tyr Leu Arg Ser Ile Ser Val Arg Asn Lys Asp
                165                 170                 175

Leu Asn Thr Leu Glu Asn Ile Thr Thr Thr Glu Phe Lys Asn Ala Ile
                180                 185                 190

Thr Asn Ala Lys Ile Ile Pro Tyr Ser Gly Leu Leu Leu Val Ile Thr
        195                 200                 205

Val Thr Asp Asn Lys Gly Ala Phe Lys Tyr Ile Lys Pro Gln Ser Gln
        210                 215                 220

Phe Ile Val Asp Leu Gly Ala Tyr Leu Glu Lys Glu Ser Ile Tyr Tyr
225                 230                 235                 240

Val Thr Thr Asn Trp Lys His Thr Ala Thr Arg Phe Ala Ile Lys Pro
                245                 250                 255

Met Glu Asp

<210> SEQ ID NO 42
<211> LENGTH: 780
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 42
atgttccaga gcagcatgcc cgccgacctg ctgatcaaag acagcaccta cacagccgcc    60
gtgcagtaca acgtgctgga aaaggacgac gaccccgcca gcctgaccat ctgggtgccc   120
atgttccaga gcagcatgcc cgccgacctg ctgatcaaag aactggccaa cgtgaacatc   180
ctggtcaagc agatcagcac ccccaagggc cccagcctga gagtgatgat caacagccgc   240
agcgccgtgc tggcccagat gcccagcaag ttcaccatct gcgccaacgt gtccctggac   300
gagcggagca gctggcctta cgacgtgacc accccctgcg agatcaaggc ctgcagcctg   360
acctgcctga gtccaagaa catgctgacc accgtgaagg acctgaccat gaagaccctg   420
aaccccaccc acgacatcat tgccctgtgc gagttcgaga acatcgtgac cagcaagaaa   480
gtgatcatcc ccacctacct gcggagcatc agcgtgcgga caaggacct gaacaccctg   540 gaaaacatca ccaccaccga gttcaagaac gccattacca cgccaagat catccctac    600 agcggcctgc tgctggtcat caccgtgacc gacaacaagg gcgccttcaa gtacatcaag   660
ccccagagcc agttcatcgt ggacctgggc gcctacctgg aaaagaatc catctactac    720 gtcaccacca actggaagca caccgccacc agattcgcca tcaagcccat ggaagattga   780

<210> SEQ ID NO 43
<211> LENGTH: 194
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 43

```
Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60

Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Pro Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Thr Thr Leu Asp Ile His Lys Ser Ile Thr Ile Asn Asn Pro
                165                 170                 175

Lys Glu Ser Thr Val Ser Asp Ile Asn Asp His Ala Lys Asn Asn Asp
            180                 185                 190

Thr Thr
```

<210> SEQ ID NO 44
<211> LENGTH: 585
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 44

```
atgtcacgaa ggaatccttg caaatttgaa attcgaggtc attgcttgaa tggtaagagg      60
tgtcattta gtcataatta ttttgaatgg ccaccccatg cactgcttgt aagacaaaac     120
tttatgttaa acagaatact taagtctatg gataaaagca tcgatacttt atcagaaata     180
agtggagctg cagagttgga cagaacagaa gagtatgccc tcggtgtagt tggagtgcta     240
gagagttata taggatctat aaataatata actaaacaat cagcatgtgt tgccatgagc     300
aaactcctca ctgaactcaa cagtgatgac atcaaaaaac tgagggacaa tgaagagcca     360
aattcaccca gataagagt gtacaatact gtcatatcat atattgaaag caacaggaaa     420
aacaataaac aaactatcca tctgttaaaa agattgccag cagacgtatt gaagaaaacc     480
ataaaaacca cattggatat ccacaagagc ataccatca ataacccaaa agaatcaact     540
gttagtgata taacgacca tgccaaaaat aatgatacta cctga                     585
```

<210> SEQ ID NO 45
<211> LENGTH: 194
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 45

```
Met Ser Arg Arg Asn Pro Cys Lys Phe Glu Ile Arg Gly His Cys Leu
1               5                   10                  15
Asn Gly Lys Arg Cys His Phe Ser His Asn Tyr Phe Glu Trp Pro Pro
                20                  25                  30
His Ala Leu Leu Val Arg Gln Asn Phe Met Leu Asn Arg Ile Leu Lys
            35                  40                  45
Ser Met Asp Lys Ser Ile Asp Thr Leu Ser Glu Ile Ser Gly Ala Ala
        50                  55                  60
Glu Leu Asp Arg Thr Glu Glu Tyr Ala Leu Gly Val Val Gly Val Leu
65                  70                  75                  80
Glu Ser Tyr Ile Gly Ser Ile Asn Asn Ile Thr Lys Gln Ser Ala Cys
                85                  90                  95
Val Ala Met Ser Lys Leu Leu Thr Glu Leu Asn Ser Asp Asp Ile Lys
            100                 105                 110
Lys Leu Arg Asp Asn Glu Glu Leu Asn Ser Pro Lys Ile Arg Val Tyr
        115                 120                 125
Asn Thr Val Ile Ser Tyr Ile Glu Ser Asn Arg Lys Asn Asn Lys Gln
    130                 135                 140
Thr Ile His Leu Leu Lys Arg Leu Pro Ala Asp Val Leu Lys Lys Thr
145                 150                 155                 160
Ile Lys Asn Thr Leu Asp Ile His Lys Ser Ile Thr Ile Asn Asn Pro
                165                 170                 175
Lys Glu Ser Thr Val Ser Asp Thr Asn Asp His Ala Lys Asn Asn Asp
            180                 185                 190
Thr Thr
```

<210> SEQ ID NO 46
<211> LENGTH: 585
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 46

| | | |
|---|---|---|
| atgagccggc ggaacccctg caagttcgag atccggggcc actgcctgaa cggcaagcgg | 60 |
| tgccacttca gccacaacta cttcgagtgg ccccctcacg ccctgctggt gcgccagaac | 120 |
| ttcatgctga accggatcct gaagtccatg gacaagagca tcgacaccct gagcgagatc | 180 |
| agcggagctg ccgagctgga ccggaccgag gaatatgccc tgggcgtggt gggagtgctg | 240 |
| gaaagctaca tcggcagcat caacaacatc accaagcaga gcgcctgcgt ggccatgagc | 300 |
| aagctgctga ccgagctgaa cagcgacgac atcaagaagc tgcgggacaa cgaggaactg | 360 |
| aacagcccca gatccgggt gtacaacacc gtgatcagct acatcgagag caaccggaag | 420 |
| aacaacaagc agaccatcca tctgctgaag cggctgcccg ccgacgtgct gaagaaaacc | 480 |
| atcaagaaca ccctggacat ccacaagtcc atcaccatca acaacccaa agaaagcacc | 540 |
| gtgtccgaca ccaacgacca cgccaagaac aacgacacca cctga | 585 |

```
<210> SEQ ID NO 47
<211> LENGTH: 241
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 47

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
50                  55                  60

Pro Thr Asn Glu Thr Asp Asp Thr Val Gly Asn Lys Pro Asn Tyr Gln
65                  70                  75                  80

Arg Lys Pro Leu Val Ser Phe Lys Glu Asp Pro Thr Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Asp
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220

Asn Leu Leu Glu Gly Asn Asp Ser Asp Asn Asp Leu Ser Leu Asp Asp
225                 230                 235                 240

Phe

<210> SEQ ID NO 48
<211> LENGTH: 726
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 48
atggaaaagt ttgctcctga attccatgga gaagatgcaa acaacagagc taccaaattc      60
ctagaatcaa taagggcaa attcacatca cctaaagatc caagaaaaa agatagtatc      120 atatctgtca actcaataga tatagaagta accaaagaaa gccctataac atcaaattca      180
accattataa acccaacaaa tgagacagat gatactgtag ggaacaagcc caattatcaa      240
agaaaacctc tagtaagttt caagaagac cctacgccaa gtgataatcc cttttcaaaa      300
ctatacaaag aaaccataga acatttgat aacaatgaag aagaatctag ctattcatat      360
gaagaaataa atgatcagac aaacgataat ataacagcaa gattagatag gattgatgaa      420
```

```
aaattaagtg aaatactagg aatgcttcac acattagtag tagcgagtgc aggacctaca    480
tctgctcggg atggtataag agatgccatg gttggtttaa gagaagacat gatagaaaaa    540
atcagaactg aagcattaat gaccaatgac agactagaag ctatggcaag actcaggaat    600
gaggaaagtg aaaagatggc aaaagacaca tcagatgaag tgtctctcaa tccaacatca    660
gagaaattga caacctgtt ggaagggaat gatagtgaca atgatctatc acttgatgat    720
ttctga                                                                726
```

<210> SEQ ID NO 49
<211> LENGTH: 241
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 49

```
Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Ile Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Thr Ala Gly Asn Lys Pro Asn Tyr Gln
65                  70                  75                  80

Arg Lys Pro Leu Val Ser Phe Lys Glu Asp Pro Thr Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Ile Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220

Asn Leu Leu Glu Gly Asn Asp Ser Asp Asn Asp Leu Ser Leu Glu Asp
225                 230                 235                 240

Phe
```

<210> SEQ ID NO 50
<211> LENGTH: 726
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 50

```
atggaaaagt tcgcccccga gttccacggc gaggacgcca acaaccgggc caccaagttt     60
ctggaatcca tcaagggcaa gttcaccagc cccaaggacc ccaagaagaa ggacagcatc    120
atcagcgtga acagcatcga catcgaagtg accaaagaga gccccatcac cagcaacagc    180
accatcatca accccaccaa cgagacagac gacaccgccg gcaacaagcc caactaccag    240
cggaagcccc tggtgtcctt caaagaggac cccaccccca gcgacaaccc cttcagcaag    300
ctgtacaaag agacaatcga gacattcgac aacaacgagg aagagagcag ctacagctac    360
gaggaaatca acgaccagac caacgacaac atcaccgcca gactggaccg gatcgacgag    420
aagctgagcg agatcctggg catgctgcac accctggtgg tggcctctgc cggccctaca    480
agcgccagag atggcatccg ggacgccatg atcggcctgc gggaagagat gatcgagaag    540
atccggaccg aggccctgat gaccaacgac cggctggaag ccatggcccg gctgcggaac    600
gaggaatccg agaagatggc caaggacacc agcgacgagg tgtccctgaa ccccaccctct   660 gagaagctga caacctgct ggaaggcaac gacagcgaca acgacctgag cctggaagat     720
ttctga                                                               726
```

US 12,370,252 B2

RSV VIRUS-LIKE PARTICLES AND METHODS OF USE THEREOF

CROSS REFERENCE TO RELATED APPLICATIONS

This application is a national stage application filed under 35 U.S.C. § 371 of PCT/US2019/058559 filed Oct. 29, 2019, which claims the benefit of U.S. Provisional Patent Application Ser. No. 62/751,975 filed Oct. 29, 2018, the disclosures of which are expressly incorporated herein by reference.

FIELD

The present disclosure relates to virus-like particles and uses thereof.

BACKGROUND

Respiratory Syncytial Virus (RSV) was quickly recognized as an important pediatric pathogen after its discovery in the 1950s. It causes upper and lower respiratory tract infections including bronchitis, bronchiolitis, and pneumonia. Most children are infected by 2 years of age. However, since its infection provides incomplete protection, RSV infects throughout life with the elderly and persons with chronic cardiac or pulmonary disease, or immune compromising conditions at higher risk for severe complications. It is estimated that globally there are more than 33 million episodes of RSV infections and 95,000-150,000 RSV deaths, mostly in developing countries, in children<5 years of age. RSV-related deaths are rare in the United States; it is, however, responsible for an estimated 60,000-170,000 hospitalizations each year in children<5 years of age. Also, infants hospitalized with RSV infection are prone to later development of obstructive airway diseases and asthma. Its substantial global disease burden has made RSV a high priority for vaccine and anti-viral drug development. There are, however, no effective anti-viral drugs or vaccines yet available. Therefore, what is needed is a vaccine for inducing protective immunity to RSV infection. The compositions and methods disclosed herein address these and other needs.

SUMMARY

Disclosed herein are virus like-particles (VLPs) for use in inducing immunity to respiratory syncytial virus (RSV) infections or symptoms thereof.

In some aspects, disclosed herein is a virus like particle (VLP) comprising a respiratory syncytial virus (RSV) M protein and an RSV M2-1 protein.

In some embodiments, the VLP comprises one or more additional RSV proteins. In some embodiments, the VLP comprises an RSV F protein. In some embodiments, the RSV F protein is selected from a group consisting of a pre-fusion form of the RSV F protein, a post-fusion form of the RSV F protein, and a carbonyl terminal portion of the RSV F protein. In some embodiments, the RSV F protein comprises a sequence selected from the group consisting of SEQ ID NO: 23, SEQ ID NO: 26, SEQ ID NO: 29, SEQ ID NO: 32, SEQ ID NO: 34, SEQ ID NO: 36, and SEQ ID NO: 37. In some embodiments, the carbonyl terminal portion of the RSV F protein comprises a sequence of SEQ ID NO: 32.

In some embodiments, the VLP comprises an RSV G protein. In some embodiments, the RSV G protein is from RSV group A or RSV group B. In some embodiments, the RSV G protein comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21.

In some embodiments, the VLP comprises a recombinant RSV G protein. In some embodiments, the recombinant RSV G protein comprises a transmembrane domain of an RSV G protein and a central conserved domain of an RSV G protein.

In some aspects, disclosed herein is a virus like particle (VLP) comprising a respiratory syncytial virus (RSV) M protein, an RSV P protein, an RSV F protein, and an RSV G protein.

In some embodiments, the RSV F protein is selected from a group consisting of a pre-fusion form of the RSV F protein, a post-fusion form of the RSV F protein, and a carbonyl terminal portion of the RSV F protein. In some embodiments, the RSV F protein comprises a sequence selected from the group consisting of SEQ ID NO: 23, SEQ ID NO: 26, SEQ ID NO: 29, SEQ ID NO: 32, SEQ ID NO: 34, SEQ ID NO: 36, and SEQ ID NO: 37. In some embodiments, the carbonyl terminal portion of the RSV F protein comprises a sequence of SEQ ID NO: 32.

In some embodiments, the RSV G protein is from RSV group A or RSV group B. In some embodiments, the RSV G protein is from RSV group A and RSV group B. In some embodiments, the RSV G protein comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21.

In some embodiments, the RSV G protein is a recombinant RSV G protein. In some embodiments, the VLP comprises a recombinant RSV G protein. In some embodiments, the recombinant RSV G protein comprises a transmembrane domain of the RSV G protein and a central conserved domain of the RSV G protein.

In some aspects, disclosed herein is a vaccine comprising the VLP of any preceding aspect. In some embodiments, the vaccine further comprises an adjuvant.

In some aspects, disclosed herein is a method of inducing an immunological response to RSV infection or at least one symptom thereof in a subject, comprising administering one or more effective doses of the vaccine of any preceding aspect. In some embodiments, the one or more effective doses of the vaccine are administered to the subject via a route that is selected from the group consisting of an intramuscular route, a subcutaneous route, an intradermal route, an oral administration, a nasal administration, and inhalation.

BRIEF DESCRIPTION OF THE DRAWINGS

The accompanying figures, which are incorporated in and constitute a part of this specification, illustrate several aspects described below.

FIG. 1A shows VLPs MFGP and MFGM2-1. FIG. 1B shows VLPs MFG$_P$P and MFG$_P$M2-1. FIG. 1C shows MGP, MFP, and MF$_t$GP VLPs. G$_P$, truncated G: aa 1-86+155-206. F$_t$, truncated F: aa 496-574.

FIG. 2A shows that a 3 µl aliquot containing the diluted sample was applied for 1 min onto a formvar/carbon coated, 300 mesh-copper grid that has been glow discharged for 30 sec, then negatively stained with 0.75% freshly-made uranyl formate on ice for 1 min. Data were collected using a FEI T20 electron microscope operating at 200 kV (pixel size 1.101 A, total electron dose is 54 electrons/A square)". FIG. 2B shows that MFGP VLPs were labeled with 3D3 or motavizumab followed by incubating with gold-labeled anti human secondary antibody.

FIG. 3A shows schematic schedule of animal experiments. FIG. 3B shows that sera from immunized animals (diluted 1:200) were used in binding ELISA to immobilize 293F cell lysate containing Ga, Gb, or F antigen. After blocking, plates were incubated with goat anti mouse IgG-HRP secondary antibody. OPD substrate was used to develop reaction and absorbance at 490 nm was read. FIG. 3C shows that sera from immunized animals were heat inactivated at 56° C. for 30 min followed by 2-fold serial dilution in triplicates. The dilutions were incubated with 100 TCID50 of RSV A2 virus for 1 h at RT. The mixtures were then transferred to monolayer HEp-2 cell and incubated for 1 h at 37° C. in 5% $CO_2$. 5% FBS+MEM media was added to the cells followed by incubation for 72 h at 37° C. in 5% $CO_2$. Cells were fixed and ELISA was performed using goat anti-RSV antibody and HPR-conjugated donkey anti-goat secondary antibody. Reaction was developed by OPD and absorbance read at 490 nm. Neutralizing titers were calculated using Reed-Muench method.

FIG. 5A shows representative images from corresponding groups. FIG. 5B shows quantitative data converted from histopathology scale. * p<0.05, ** p<0.01.

FIG. 6 shows domains of Ga protein, Gb protein, Fpost protein and Fpre protein and combination of F and G expression of RSV VLPs using platforms M+P and M+M2-1.

DETAILED DESCRIPTION

Figures 1A, 1B, 1C:
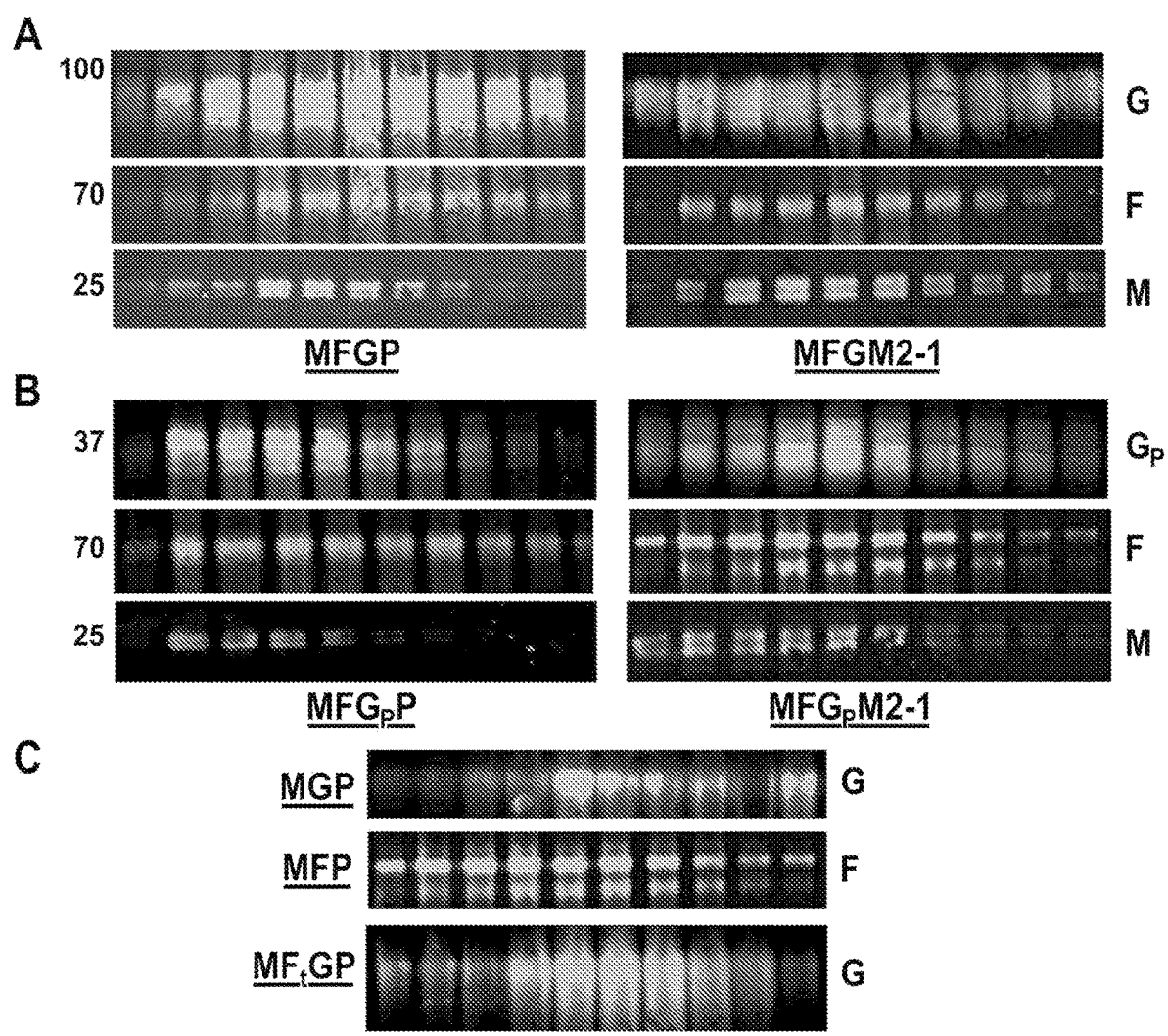
FIGS. 1A-1C show generation and expression of F and G on RSV VLPs. 293F cell line expressing RSV gene M, F (or $F_t$), G (or $G_P$) and P or M2-1 were induced for 72 h in 2 µg/ml doxycycline. Cells were harvested and low centrifugation performed to separate cells and VLPs-containing supernatant. VLPs were filtered through 0.45 µm filter to clear cell debris, layered on top of 20% sucrose and subjected to centrifugation at 12,200×g for 2 h, 4° C. VLP pellets were resuspended in sterile PBS and subjected to centrifugation through a 20-60% sucrose gradient at 11,000×g for 12 h, 4° C. A total of 10 fractions were collected and analyzed by immunoblotting using 3D3 (human anti-G antibody), motavizumab (human anti-F antibody), and rabbit serum anti-M antibody.
Figure 2A:
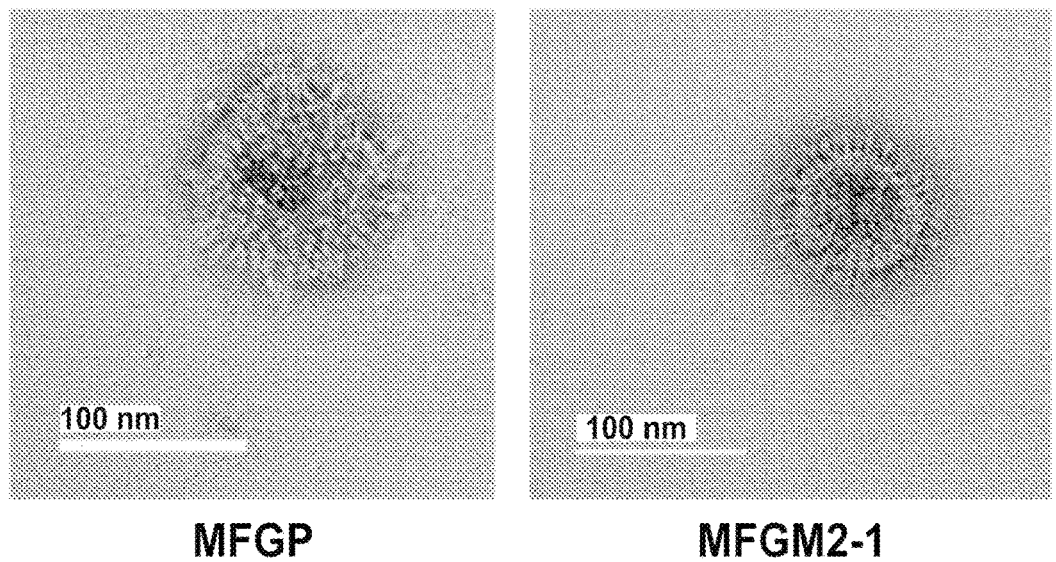
FIGS. 2A and 2B show that glycoproteins are visualized as spikes on VLPs by negative stain electron microscopy.
Figure 2B:
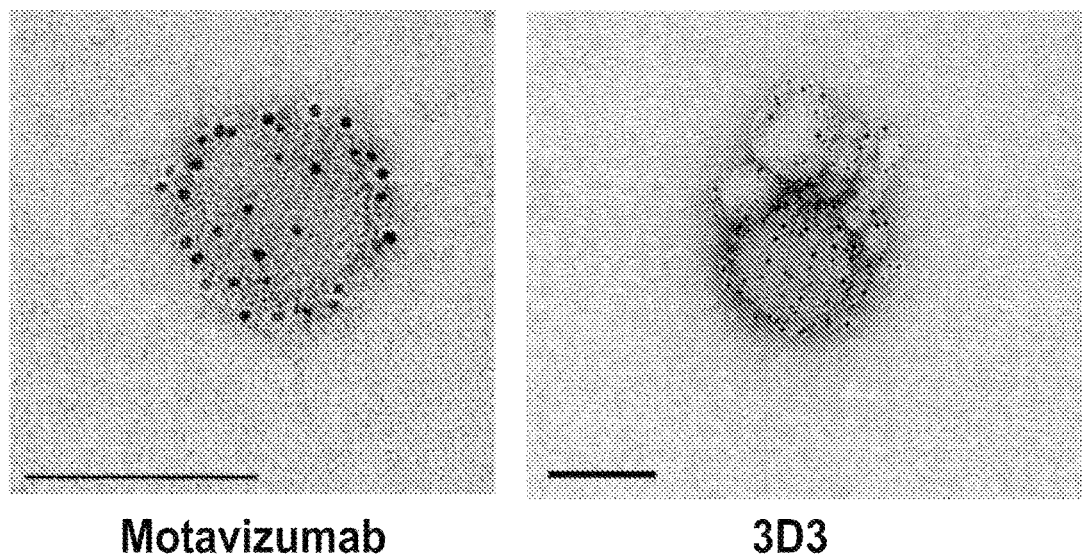

RSV is a single-stranded, negative sense RNA virus belonging to Paramyxoviridae family and Pneumoviridae subfamily with two distinct antigenic groups, A and B. The RSV genome of approximately 15.2 kb includes ten genes that encode for eleven proteins. Three proteins, the fusion (F), attachment (G), and small hydrophobic (SH) are expressed on the virion envelop. The F and G proteins are the only proteins shown to induce effective neutralizing antibodies and longer-term protective immunity. The F protein is more conserved among RSV strains and induces cross-protective immunity and is most effective at inducing neutralizing antibodies. The SH protein does induce some protection likely through Fc receptor-mediated activity such as antibody dependent cellular cytotoxicity or complement activation. Most neutralizing antibodies in human serum specimens are against the pre-fusion form of F and pre-fusion F is currently a prime candidate for RSV vaccines. The G protein, though eliciting less potent neutralizing antibody, has been shown to be an important factor for RSV disease pathogenesis making it also a candidate for inclusion in an RSV vaccine. The G protein structure consists of a conserved region that contains a CX3C chemokine motif that enables binding to the CX3C chemokine receptor, CX3CR1, and has some activities similar to the CX3C chemokine fractalkine. The G protein induces disease causing inflammatory responses that can be inhibited by blocking G binding to CX3CR1 with passive administration of an anti-G monoclonal antibody, G peptide vaccine induced antibodies, or by mutating the CX3C motif. Thus, a vaccine that induces both anti-F and anti-G antibodies can decrease disease by both decreasing viral replication and producing an anti-inflammatory effect.

Despite over 60 years of research, no effective vaccine or antiviral drug is available. Studies, however, show most neutralizing antibodies produced after RSV infection are against the surface fusion F and attachment G glycoproteins, thus making these the prime candidates for vaccines. In fact, antibodies induced by the F protein reduce viral titers. Antibodies induced by the G protein are less effective at reducing viral titers than those induced by F but reduce inflammation and disease more effectively. Among different strategies for RSV vaccines, virus-like particles (VLPs) are safe, immunogenic, and used in licensed human vaccines.

Disclosed herein is a vaccine that includes both the F and G proteins utilizing M based virus-like particles (VLPs). An RSV-based vaccine platform is optimal since all components can contribute to vaccine-induced immunity and the protein structures in the VLP better reflect natural structures. A VLP that better reflects the structure in the virus can induce a more effective immune response and provide a better model for structural studies. RSV VLPs have previously been developed using the Newcastle disease, influenza, or bacterial phage P22 platforms with the RSV F and/or G proteins or M and M2 proteins.

Disclosed herein are novel RSV VLPs with F and/or G proteins using an RSV platform with M plus P or M plus M2-1. Since M2-1 is important for structural stability of RSV, M2-1 can also contribute to VLP formation. The data herein show that an RSV-based vaccine platform can be used to efficiently form RSV VLPs with either M plus P or M plus M2-1 with F and/or G proteins. Unexpectedly, the inventors found that the G protein was only efficiently incorporated into these VLPs in the presence of the intracellular and transmembrane domains of F.

Described herein are virus like-particles (VLPs) and methods for inducing immunity to respiratory syncytial virus (RSV) infections or symptoms thereof. In one aspect, disclosed herein is a virus like particle (VLP) comprising a respiratory syncytial virus (RSV) M protein and an RSV M2-1 protein, wherein the VLP further comprises an RSV F protein and/or an RSV G protein. In one aspect, disclosed herein is a virus like particle (VLP) comprising a respiratory syncytial virus (RSV) M protein, an RSV P protein, an RSV F protein, and an RSV G protein.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs.

Terminology

Terms used throughout this application are to be construed with ordinary and typical meaning to those of ordinary skill in the art. However, Applicant desires that the following terms be given the particular definition as defined below.

As used herein, the article "a," "an," and "the" means "at least one," unless the context in which the article is used clearly indicates otherwise.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10%. In another non-limiting embodiment, the terms are defined to be within 5%. In still another non-limiting embodiment, the terms are defined to be within 1%.

As used herein the term "adjuvant" refers to a compound that, when used in combination with a specific immunogen in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

A "composition" is intended to include a combination of active agent and another compound or composition, inert (for example, a detectable agent or label) or active, such as an adjuvant.

As used herein, the term "virus-like particle" (VLP) refers to a structure that in at least one attribute resembles a virus but which has not been demonstrated to be infectious. In general, virus-like particles lack a viral genome and, therefore, are noninfectious. In addition, virus-like particles can often be produced in large quantities by heterologous expression and can be easily purified.

As used herein, the term "vaccine" refers to a formulation which contains VLPs of the present invention, which is in a form that is capable of being administered to a subject and which induces a protective immune response sufficient to induce immunity to prevent and/or ameliorate an infection and/or to reduce at least one symptom of an infection and/or to enhance the efficacy of another dose of VLPs. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of CD8+ T cells, antigen presenting cells, CD4+ T cells, dendritic cells and/or other cellular responses.

As used herein an "effective dose" generally refers to that amount of VLPs or vaccines of the invention sufficient to induce immunity, to prevent and/or ameliorate an infection or to reduce at least one symptom of an infection and/or to enhance the efficacy of another dose of a VLP or a vaccine. An effective dose may refer to the amount of VLPs or vaccines sufficient to delay or minimize the onset of an infection or a symptom of an infection. An effective dose may also refer to the amount of VLPs or vaccines that provides a therapeutic benefit in the treatment or management of an infection a symptom of an infection. Further, an effective dose is the amount with respect to VLPs or vaccines of the invention alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, (e.g., by plaque neutralization, complement fixation, enzyme-linked immunosorbent, or microneutralization assay) and/or responses of virus-specific CD4+ T cells and CD8+ T cells, and/or responses of other immune cells. In the case of a vaccine, an "effective dose" is one that prevents or reduces disease and/or prevents or reduces the severity of symptoms.

As used herein, the term "effective amount" refers to an amount of VLPs or vaccines comprising VLPs necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to VLPs or vaccines comprising VLPs of the invention. The term is also synonymous with "sufficient amount."

An "immunological response" or "immunity" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein the term "protective immune response", "protective response", or "protective immunity" refers to an immune response mediated by antibodies against an infectious agent, which is exhibited by a vertebrate (e.g., a human), that prevents or ameliorates an infection or reduces at least one symptom thereof. VLPs of the invention can stimulate the production of antibodies that, for example, neutralize infectious agents, block infectious agents from entering cells, block replication of said infectious agents, and/or protect host cells from infection and destruction. The term can also refer to an immune response that is mediated by T cells, B cells, and/or other white blood cells against an infectious agent, exhibited by a vertebrate (e.g., a human), that prevents or ameliorates RSV infection or reduces at least one symptom thereof.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences*, 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

"Therapeutically effective amount" or "therapeutically effective dose" of a composition (e.g. a VLP or a vaccine comprising a VLP) refers to an amount that is effective to achieve a desired therapeutic result. In some embodiments, a desired therapeutic result is the prevention of an RSV infection and/or a symptom thereof. In some embodiments, a desired therapeutic result is the treatment of an RSV infection and/or a symptom thereof. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22: 1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers.

The term "polypeptide" refers to a compound made up of a single chain of D- or L-amino acids or a mixture of D- and L-amino acids joined by peptide bonds.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) nucleotide sequence identity is defined as the percentage of amino acids in a candidate sequence that are identical to the nucleotides in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The term "engineered" or "recombinant" means a polynucleotide or polypeptide of semisynthetic, or synthetic origin that either does not occur in nature or is operably linked to another polynucleotide in an arrangement not found in nature.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In some embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

A "vector" refers to a recombinant DNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector may be able to but does not need to be capable of replication in the ultimate target cell or subject. The term includes vectors for cloning as well as viral vectors.

The term "gene" or "gene sequence" refers to the coding sequence or control sequence, or fragments thereof. A gene may include any combination of coding sequence and control sequence, or fragments thereof. Thus, a "gene" as referred to herein may be all or part of a native gene. A polynucleotide sequence as referred to herein may be used interchangeably with the term "gene", or may include any coding sequence, non-coding sequence or control sequence, fragments thereof, and combinations thereof. The term "gene" or "gene sequence" includes, for example, control sequences upstream of the coding sequence (for example, the ribosome binding site).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Virus-Like Particles and Vaccines

Respiratory Syncytial Virus (RSV) is the leading cause of severe bronchiolitis in infants and young children and a high priority for vaccine development. Disclosed herein are virus-like particles (VLPs) and the use thereof for inducing immune responses to RSV infection or at least one symptom thereof in a subject. VLPs are used herein for vaccines since they are immunogenic and are safe to human. The present disclosure provides RSV VLPs with F and/or G using an RSV platform with M plus P or M plus M2-1, and uses thereof for inducing protective immune responses.

The respiratory syncytial virus (RSV), a member of the species orthopneumovirus of Orthopneumovirus genus, is a syncytial virus that causes respiratory tract infections. RSV has a single stranded negative sense RNA genome which is approximately 15.2 Kb long. RSV has been classified into two groups (group A and group B, or termed as "strain A and strain B" herein) on the basis of genetic and antigenic heterogeneity. The two major glycoprotein on the surface of the RSV virion are the attachment glycoprotein (G) and fusion protein (F). G is involved in attachment of virion to the host cells, and F cause the virion membrane to fuse with cell membrane. In addition, four of the viral genes code for intracellular proteins that are involved in genome transcription, replication, and particle budding, namely N (nucleoprotein), P (phosphoprotein), M (matrix protein), and L ("large" protein, containing the RNA polymerase catalytic motifs).

In some aspects, disclosed herein is a virus like particle (VLP) comprising a respiratory syncytial virus (RSV) M protein and an RSV M2-1 protein.

As used herein, the term "RSV Matrix" or "RSV M" protein refers to an RSV protein that, when expressed in a host cell, induces formation of VLPs. An example of an RSV M protein is represented by SEQ ID NO: 39 or SEQ ID NO: 41. The term also comprises any variants, derivatives and/or fragments of RSV M protein that, when expressed in a host cell, induces formation of VLPs. In some embodiments, the M polypeptide comprises the sequence set forth in SEQ ID NO: 39 or SEQ ID NO: 41, or sequence having at or greater than about 80%, about 85%, about 90%, about 95%, about 98%, or about 99% homology with SEQ ID NO: 39 or SEQ ID NO: 41, or a polypeptide comprising a portion of SEQ ID NO: 39 or SEQ ID NO: 41. In some embodiments, the M polypeptide comprises the sequence set forth in SEQ ID NO: 39. In some embodiments, the M polypeptide comprises the sequence set forth in SEQ ID NO: 41. The term also encompasses nucleotide sequences which encode for RSV M and/or any variants, derivatives and/or fragments thereof that when transfected (or infected) into a host cell will express RSV M protein and induce formation of VLPs. In some embodiments, the nucleotide sequence encoding M polypeptide comprises the sequence set forth in SEQ ID NO: 40 or SEQ ID NO: 42, or sequence having at or greater than about 80%, about 85%, about 90%, about 95%, about 98%, or about 99% homology with SEQ ID NO: 40 or SEQ ID NO: 42, or a polynucleotide comprising a portion of SEQ ID NO: 40 or SEQ ID NO: 42.

As used herein, the term "RSV M2-1 protein" or "M2-1 protein" refers to a cofactor of the RSV viral RNA polymerase complex and functions as a transcriptional processivity and antitermination factor. An example of an RSV M2-1 protein is represented by SEQ ID NO: 43 or SEQ ID NO: 45. The term also comprises any variants, derivatives and/or fragments of RSV M2-1 protein that, when expressed in a host cell, induces formation of VLPs. In some embodiments, the M2-1 polypeptide comprises the sequence set forth in SEQ ID NO: 43 or SEQ ID NO: 45, or sequence having at or greater than about 80%, about 85%, about 90%, about 95%, about 98%, or about 99% homology with SEQ ID NO: 43 or SEQ ID NO: 45, or a polypeptide comprising a portion of SEQ ID NO: 43 or SEQ ID NO: 45. In some embodiments, the M2-1 polypeptide comprises the sequence set forth in SEQ ID NO: 43. In some embodiments, the M2-1 polypeptide comprises the sequence set forth in SEQ ID NO: 45. The term also encompasses nucleotide sequences which encode for RSV M2-1 and/or any variants, derivatives and/or fragments thereof that when transfected (or infected) into a host cell will express RSV M2-1 protein and induce formation of VLPs. In some embodiments, the nucleotide sequence encoding M2-1 polypeptide comprises the sequence set forth in SEQ ID NO: 44 or SEQ ID NO: 46, or sequence having at or greater than about 80%, about 85%, about 90%, about 95%, about 98%, or about 99% homology with SEQ ID NO: 44 or SEQ ID NO: 46, or a polynucleotide comprising a portion of SEQ ID NO: 44 or SEQ ID NO: 46.

In some embodiments, the VLP of any preceding aspect comprises one or more additional RSV proteins. In some embodiments, the VLP comprises an RSV F protein. As used herein, the terms "RSV F protein", "F protein" refers to an RSV fusion protein. The RSV F protein directs penetration of RSV by fusion between the virion's envelope protein and the host cell plasma membrane. Later in infection, the F protein expressed on the cell surface can mediate fusion with neighboring cells to form syncytia. The F protein is a type I transmembrane surface protein that has a N-terminal cleaved signal peptide and a membrane anchor near the C-terminus. RSV F is synthesized as an inactive F0 precursor that assembles into a homotrimer and is activated by cleavage in the trans-Golgi complex by a cellular endoprotease to yield two disulfide-linked subunits. The N-terminus of the F1 subunit that is created by cleavage contains a hydrophobic domain (the fusion peptide) that inserts directly into the target membrane to initiate fusion. The F1 subunit also contains heptad repeats that associate during fusion, driving a conformational shift that brings the viral and cellular membranes into close proximity. Because the F protein is expressed on the surface of infected cells and is responsible for subsequent fusion with other cells leading to syncytia formation, antibodies or cellular immune responses to the F protein can neutralize virus and/or block entry of the virus into the cell or prevent syncytia formation.

Accordingly, in some embodiments, the RSV F protein of any preceding aspect is selected from a group consisting of a pre-fusion form of the RSV F protein, a post-fusion form of the RSV F protein, and a carbonyl terminal portion of the RSV F protein. In some embodiments, the RSV F protein is the pre-fusion form of the RSV F protein. In some embodiments, the RSV F protein is the post-fusion form of the RSV F protein. In some embodiments, the RSV F protein is the carbonyl terminal portion of the RSV F protein. In some embodiments, the RSV F protein comprises a sequence selected from the group consisting of SEQ ID NO: 23, SEQ ID NO: 26, SEQ ID NO: 29, SEQ ID NO: 32, SEQ ID NO: 34, SEQ ID NO: 36, and SEQ ID NO: 37.

In some embodiments, the F polypeptide comprises the sequence set forth in SEQ ID NO: 23. In some embodiments, the F polypeptide comprises the sequence set forth in SEQ ID NO: 26. In some embodiments, the F polypeptide comprises the sequence set forth in SEQ ID NO: 29. In some embodiments, the F polypeptide comprises the sequence set forth in SEQ ID NO: 32. In some embodiments, the F polypeptide comprises the sequence set forth in SEQ ID NO: 34. In some embodiments, the F polypeptide comprises the sequence set forth in SEQ ID NO: 36. In some embodiments, the F polypeptide comprises the sequence set forth in SEQ ID NO: 37.

The term "RSV F protein" or "F" protein also encompasses nucleotide sequences which encode for an RSV F and/or any variants, derivatives and/or fragments thereof that when transfected (or infected) into a host cell will express an RSV F protein and induce formation of VLPs. In some embodiments, the RSV F polypeptide comprises the sequence set forth in SEQ ID NO: 23, SEQ ID NO: 26, SEQ ID NO: 29, SEQ ID NO: 32, SEQ ID NO: 34, SEQ ID NO: 36, or SEQ ID NO: 37, or sequence having at or greater than about 80%, about 85%, about 90%, about 95%, about 98%, or about 99% homology with the sequence set forth in SEQ ID NO: 23, SEQ ID NO: 26, SEQ ID NO: 29, SEQ ID NO: 32, SEQ ID NO: 34, SEQ ID NO: 36, or SEQ ID NO: 37, or a polypeptide comprising a portion of the sequence set forth in SEQ ID NO: 23, SEQ ID NO: 26, SEQ ID NO: 29, SEQ ID NO: 32, SEQ ID NO: 34, SEQ ID NO: 36, or SEQ ID NO: 37. In some embodiments, the nucleotide sequence encoding the RSV F polypeptide comprises the sequence set forth in SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 35, or SEQ ID NO: 38, or sequence having at or greater than about 80%, about 85%, about 90%, about 95%, about 98%, or about 99% homology with SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 35, or SEQ ID NO: 38, or a polynucleotide comprising a portion of SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 35, or SEQ ID NO: 38.

In some embodiments, the carbonyl terminal portion form of the RSV F polypeptide comprises the sequence set forth in SEQ ID NO: 32, or sequence having at or greater than about 80%, about 85%, about 90%, about 95%, about 98%, or about 99% homology with SEQ ID NO: 32, or a polypeptide comprising a portion of SEQ ID NO: 32. The term also encompasses nucleotide sequences which encode for the carbonyl terminal portion form of the RSV F polypeptide and/or any variants, derivatives and/or fragments thereof that when transfected (or infected) into a host cell will express the carbonyl terminal portion form of the RSV F polypeptide and induce formation of VLPs. In some embodiments, the nucleotide sequence encoding the carbonyl terminal portion form of the RSV F polypeptide comprises the sequence set forth in SEQ ID NO: 33, or sequence having at or greater than about 80%, about 85%, about 90%, about 95%, about 98%, or about 99% homology with SEQ ID NO: 33, or a polynucleotide comprising a portion of SEQ ID NO: 33.

In some embodiments, the VLP of any preceding aspect further comprises an RSV G protein. In some embodiments, the RSV G protein is from RSV group A or RSV group B. In some embodiments, the RSV G protein is from RSV group A. In some embodiments, the RSV G protein is from RSV group B. In some embodiments, the RSV G protein is from RSV group A and RSV group B.

As used herein, the terms "RSV G protein" or "G protein" refers to a type II transmembrane glycoprotein with a single hydrophobic region near the N-terminal end that serves as both an uncleaved signal peptide and a membrane anchor, leaving the C-terminal two-thirds of the molecule oriented externally. In some embodiments, the RSV G polypeptide comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or sequence having at or greater than about 80%, about 85%, about 90%, about 95%, about 98%, or about 99% homology with a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or a polypeptide comprising a portion of a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21. The term also encompasses nucleotide sequences which encode for the RSV G polypeptide and/or any variants, derivatives and/or fragments thereof that when transfected (or infected) into a host cell will express various forms of the RSV G protein and induce formation of VLPs (for example, secreted or membrane-bound G proteins). In some embodiments, the nucleotide sequence encoding the RSV G protein comprises a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or sequence having at or greater than about 80%, about 85%, about 90%, about 95%, about 98%, or about 99% homology with a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or a polynucleotide comprising a portion of a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22. In some embodiments, the G protein comprises a sequence of SEQ ID NO: 1. In some embodiments, the G protein comprises a sequence of SEQ ID NO: 11. In some embodiments, the G protein comprises a sequence of SEQ ID NO: 15. In some embodiments, the G protein comprises a sequence of SEQ ID NO: 17.

The G protein structure consists of a central conserved region (CCD-G) that contains a CX3C chemokine motif that enables binding to the CX3C chemokine receptor, CX3CR1 (HGNC: 2558, Entrez Gene: 1524, Ensembl: ENSG00000168329, OMIM: 601470, UniProtKB: P49238), a crucial chemokine receptor involved in migration and adhesion of leukocytes. The CX3C motif is known to those of skill in the art. In some embodiments, the CX3C motif is from amino acid 182 to 186 of an RSV G protein from group A. G protein induced inflammatory responses can be reduce by blocking G protein binding to CX3CR1. The present disclosure shows that the anti-G protein antibodies induced by the vaccine disclosed herein and reduces RSV infection related inflammation. Therefore, in some embodiments, the VLPs of any preceding aspect comprises a recombinant RSV G protein, wherein the recombinant RSV G protein comprises an intracellular and transmembrane domain plus about 20 to about 25 aa of the extracellular domain and/or a CCD-G of an RSV G protein, wherein the RSV G protein is from RSV group A and/or group B. In some embodiments, the transmembrane domain term used herein can indicate intracellular and transmembrane domains plus about 20 to about 25 aa of the extracellular domain (e.g. aa 1-86 or 1-91). In some embodiments, the intracellular plus transmembrane plus initial sequences of the extracellular domain of an RSV G protein comprises amino acids 1-86 of an RSV from group A or amino acids 1-77 of an RSV from group B. In some embodiments, the CCD-G domain of an RSV G protein comprises amino acid 155-206 of an RSV G protein of group A or B or amino acid 146-197 of an RSV G protein of group A or B or 146-206 of group A or B. In some embodiments, the RSV G protein of group A comprises a sequence of SEQ ID NO: 7 or SEQ ID NO: 9. In some embodiments, the RSV G protein of group B comprises a sequence of SEQ ID NO: SEQ ID NO: 19 or SEQ ID NO: 21. The CX3C motif can be mutated for preventing the G protein in the VLP from binding to CX3CR1, such that the VLP can be more immunogenic and safer. Therefore, in some embodiments, the CCD-G comprises a mutated CX3C motif that has one or more amino acids inserted between the two cysteines of the CX3C motif. The one or more amino acids can be any amino acid. In some embodiments, the one or more amino acids are alanines. Accordingly, in some embodiments, the recombinant G protein of any preceding aspect further comprises mutated CX3C motif, wherein the recombinant G protein comprises a sequence selected from the group consisting of SEQ ID NO: 11 and SEQ ID NO: 13.

As noted above, the term "engineered" or "recombinant" means a polynucleotide or polypeptide of semisynthetic, or synthetic origin that either does not occur in nature or is operably linked to another polynucleotide in an arrangement not found in nature. In some embodiments, recombinant RSV G protein is a G protein comprising one or more transmembrane domains of RSV G proteins and one or more CCD-G domains of RSV G proteins, wherein the transmembrane domain and the CCD-G domain can be from a same RSV group or different RSV groups. In some embodiments, the recombinant RSV G protein comprises a transmembrane domain of an RSV G protein and a CCD-G domain of an RSV G protein, wherein the transmembrane domain and the CCD-G domain can be from a same RSV group or different RSV groups. Thus, in some embodiments, the VLP disclosed herein comprises a recombinant RSV G protein comprising a transmembrane domain of an RSV G protein of RSV group A and a CCD-G domain of an RSV G protein of RSV group A. In some embodiments, the VLP disclosed herein comprises a recombinant RSV G protein comprising a transmembrane domain of an RSV G protein of RSV group A and a CCD-G domain of an RSV G protein of RSV group B. In some embodiments, the VLP disclosed herein comprises a recombinant RSV G protein comprising a transmembrane domain of an RSV G protein of RSV group B and a CCD-G domain of an RSV G protein of RSV group B. In some embodiments, the recombinant RSV G protein comprises a transmembrane domain of an RSV G protein and a group A CCD-G domain and a group B CCD-G domain of RSV G protein, wherein the transmembrane domain can be from either a group A or B RSV groups. In some embodiments, the VLP can have two recombinant G proteins, one for group A and one for group B. The recombinant RSV G protein of any preceding aspect, the transmembrane domain is operably linked to the CCD-G domain and the VLP also contains a form of the F protein.

Accordingly, in some embodiments, the recombinant G protein of any preceding aspect comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21. In some embodiments, the recombinant G protein comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or sequence having at or greater than about 80%, about 85%, about 90%, about 95%, about 98%, or about 99% homology with a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO:

21, or a polypeptide comprising a portion of a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21. In some embodiments, the nucleotide sequence encoding the recombinant G protein comprises a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or sequence having at or greater than about 80%, about 85%, about 90%, about 95%, about 98%, or about 99% homology with a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or a polynucleotide comprising a portion of a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22.

In some embodiments, the recombinant G protein comprises a sequence of SEQ ID NO: 1. In some embodiments, the recombinant G protein comprises a sequence of SEQ ID NO: 3. In some embodiments, the recombinant G protein comprises a sequence of SEQ ID NO: 5. In some embodiments, the recombinant G protein comprises a sequence of SEQ ID NO: 7. In some embodiments, the recombinant G protein comprises a sequence of SEQ ID NO: 9. In some embodiments, the recombinant G protein comprises a sequence of SEQ ID NO: 11. In some embodiments, the recombinant G protein comprises a sequence of SEQ ID NO: 13. In some embodiments, the recombinant G protein comprises a sequence of SEQ ID NO: 15. In some embodiments, the recombinant G protein comprises a sequence of SEQ ID NO: 17. In some embodiments, the recombinant G protein comprises a sequence of SEQ ID NO: 19. In some embodiments, the recombinant G protein comprises a sequence of SEQ ID NO: 21.

In some embodiments, the VLP of any preceding aspect further comprises an RSV P protein, an RSV N protein, or an RSV L protein.

In some aspects, disclosed herein is a virus like particle (VLP) comprising a respiratory syncytial virus (RSV) M protein, an RSV P protein, an RSV F protein, and an RSV G protein.

In some embodiments, the RSV F protein is selected from a group consisting of a pre-fusion form of the RSV F protein, a post-fusion form of the RSV F protein, and a carbonyl terminal portion of the RSV F protein. In some embodiments, the RSV F protein comprises a sequence selected from the group consisting of SEQ ID NO: 23, SEQ ID NO: 26, SEQ ID NO: 29, SEQ ID NO: 32, SEQ ID NO: 34, SEQ ID NO: 36, and SEQ ID NO: 37. In some embodiments, the carbonyl terminal portion of the RSV F protein comprises a sequence of SEQ ID NO: 32.

In some embodiments, the VLP comprises an RSV G protein. In some embodiments, the RSV G protein is from RSV group A or RSV group B. In some embodiments, the RSV G protein comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21.

In some embodiments, the VLP comprises a recombinant RSV G protein. In some embodiments, the recombinant RSV G protein comprises a transmembrane domain of the RSV G protein and a central conserved domain of the RSV G protein.

As used herein, the term "RSV P protein" or "P protein" refers to an RSV phosphorylation. The colocalization of M2-1 protein with N protein and P protein as part of the ribonucleoprotein (RNP) complex contributes RSV viral gene transcription and replication. An example of an RSV P protein is represented by SEQ ID NO: 47 or SEQ ID NO: 49. The term also comprises any variants, derivatives and/or fragments of RSV P protein that, when expressed in a host cell, induces formation of VLPs. In some embodiments, the P polypeptide comprises the sequence set forth in SEQ ID NO: 47 or SEQ ID NO: 49, or sequence having at or greater than about 80%, about 85%, about 90%, about 95%, about 98%, or about 99% homology with SEQ ID NO: 47 or SEQ ID NO: 49, or a polypeptide comprising a portion of SEQ ID NO: 47 or SEQ ID NO: 49. The term also encompasses nucleotide sequences which encode for RSV P and/or any variants, derivatives and/or fragments thereof that when transfected (or infected) into a host cell will express RSV P protein and induce formation of VLPs. In some embodiments, the nucleotide sequence encoding RSV P protein comprises the sequence set forth in SEQ ID NO: 48 or SEQ ID NO: 50, or sequence having at or greater than about 80%, about 85%, about 90%, about 95%, about 98%, or about 99% homology with SEQ ID NO: 48 or SEQ ID NO: 50, or a polypeptide comprising a portion of SEQ ID NO: 48 or SEQ ID NO: 50.

In some embodiments, disclosed herein is a virus like particle (VLP) comprising a respiratory syncytial virus (RSV) M protein, an RSV P protein, an RSV F protein, and an RSV G protein, wherein the VLP further comprises an RSV M2-1 protein, an RSV N protein, or an RSV L protein. Additional examples of RSV sequences and proteins are further described in U.S. Patent Application Publication U.S. 2008/0233150, which is incorporated herein by reference for all purposes.

In some aspects, disclosed herein are vaccines comprising VLPs of any preceding aspect. In some embodiments, the vaccine further comprises an adjuvant.

Optionally, the vaccine contemplated herein can be combined with an adjuvant such as Freund's incomplete adjuvant, Freund's Complete adjuvant, alum, monophosphoryl lipid A, alum phosphate or hydroxide, QS-21, salts, i.e., AlK(SO4)2, AlNa(SO4)2, AlNH4(SO4)2, silica, kaolin, carbon polynucleotides, i.e., poly IC and poly AU. Additional adjuvants can include QuilA and Alhydrogel and the like. Optionally, the vaccine contemplated herein can be combined with immunomodulators and immunostimulants such as interleukins, interferons and the like. Many vaccine formulations are known to those of skill in the art.

In some embodiments, the vaccine further comprises a pharmaceutically acceptable carrier.

Methods of Use

In some aspects, disclosed herein is a method of inducing immunity to RSV infection or at least one symptom thereof in a subject, comprising administering one or more effective doses of a vaccine comprising a virus like particle (VLP), wherein the VLP comprises a respiratory syncytial virus (RSV) M protein and an RSV M2-1 protein.

In some embodiments, the VLP further comprises an F protein. In some embodiments, the VLP further comprises a G protein. In some embodiments, the VLP further comprises an F protein and a G protein.

In some aspects, disclosed herein is a method of inducing immunity to RSV infection or at least one symptom thereof in a subject, comprising administering one or more effective doses of a vaccine comprising a virus like particle (VLP), wherein the VLP comprises a respiratory syncytial virus (RSV) M protein, an RSV P protein, an RSV F protein, and an RSV G protein.

In some aspects, disclosed herein is a method of preventing an RSV infection or at least one symptom thereof in a subject, comprising administering one or more effective doses of a vaccine comprising a virus like particle (VLP), wherein the VLP comprises a respiratory syncytial virus (RSV) M protein and an RSV M2-1 protein. In some embodiments, the VLP further comprises an F protein. In some embodiments, the VLP further comprises a G protein. In some embodiments, the VLP further comprises an F protein and a G protein.

In some aspects, disclosed herein is a method of preventing an RSV infection or at least one symptom thereof in a subject, comprising administering one or more effective doses of a vaccine comprising a virus like particle (VLP), wherein the VLP comprises a respiratory syncytial virus (RSV) M protein, an RSV P protein, an RSV F protein, and an RSV G protein.

As used herein, the terms "RSV Matrix" or "RSV M" protein refer to an RSV protein that, when expressed in a host cell, induces formation of VLPs. An example of an RSV M protein is represented by SEQ ID NO: 39 or SEQ ID NO: 41. The term also comprises any variants, derivatives and/or fragments of RSV M protein that, when expressed in a host cell, induces formation of VLPs. In some embodiments, the M polypeptide comprises the sequence set forth in SEQ ID NO: 39 or SEQ ID NO: 41, or sequence having at or greater than about 80%, about 85%, about 90%, about 95%, about 98%, or about 99% homology with SEQ ID NO: 39 or SEQ ID NO: 41, or a polypeptide comprising a portion of SEQ ID NO: 39 or SEQ ID NO: 41. The term also encompasses nucleotide sequences which encode for RSV M and/or any variants, derivatives and/or fragments thereof that when transfected (or infected) into a host cell will express RSV M protein and induce formation of VLPs. In some embodiments, the nucleotide sequence encoding M polypeptide comprises the sequence set forth in SEQ ID NO: 40 or SEQ ID NO: 42, or sequence having at or greater than about 80%, about 85%, about 90%, about 95%, about 98%, or about 99% homology with SEQ ID NO: 40 or SEQ ID NO: 42, or a polynucleotide comprising a portion of SEQ ID NO: 40 or SEQ ID NO: 42.

As used herein, the terms "RSV M2-1 protein", "M2-1 protein" refers to a cofactor of the RSV viral RNA polymerase complex and functions as a transcriptional processivity and antitermination factor. An example of an RSV M2-1 protein is represented by SEQ ID NO: 43 or SEQ ID NO: 45. The term also comprises any variants, derivatives and/or fragments of RSV M2-1 protein that, when expressed in a host cell, induces formation of VLPs. In some embodiments, the M2-1 polypeptide comprises the sequence set forth in SEQ ID NO: 43 or SEQ ID NO: 45, or sequence having at or greater than about 80%, about 85%, about 90%, about 95%, about 98%, or about 99% homology with SEQ ID NO: 43 or SEQ ID NO: 45, or a polypeptide comprising a portion of SEQ ID NO: 43 or SEQ ID NO: 45. The term also encompasses nucleotide sequences which encode for RSV M2-1 and/or any variants, derivatives and/or fragments thereof that when transfected (or infected) into a host cell will express RSV M2-1 protein and induce formation of VLPs. In some embodiments, the nucleotide sequence encoding M2-1 polypeptide comprises the sequence set forth in SEQ ID NO: 44 or SEQ ID NO: 46, or sequence having at or greater than about 80%, about 85%, about 90%, about 95%, about 98%, or about 99% homology with SEQ ID NO: 44 or SEQ ID NO: 46, or a polynucleotide comprising a portion of SEQ ID NO: 44 or SEQ ID NO: 46.

In some embodiments, the VLP of any preceding aspect comprises one or more additional RSV proteins. In some embodiments, the VLP comprises an RSV F protein. As used herein, the terms "RSV F protein", "F protein" refers to an RSV fusion protein.

Accordingly, in some embodiments, the RSV F protein of any preceding aspect is selected from a group consisting of a pre-fusion form of the RSV F protein, a post-fusion form of the RSV F protein, and a carbonyl terminal portion of the RSV F protein. In some embodiments, the RSV F protein is the pre-fusion form of the RSV F protein. In some embodiments, the RSV F protein is the post-fusion form of the RSV F protein. In some embodiments, the RSV F protein is the carbonyl terminal portion of the RSV F protein. Accordingly, in some embodiments, the RSV F protein of any preceding aspect is selected from a group consisting of a pre-fusion form of the RSV F protein, a post-fusion form of the RSV F protein, and a carbonyl terminal portion of the RSV F protein. In some embodiments, the RSV F protein is the pre-fusion form of the RSV F protein. In some embodiments, the RSV F protein is the post-fusion form of the RSV F protein. In some embodiments, the RSV F protein is the carbonyl terminal portion of the RSV F protein. In some embodiments, the RSV F protein comprises a sequence selected from the group consisting of SEQ ID NO: 23, SEQ ID NO: 26, SEQ ID NO: 29, SEQ ID NO: 32, SEQ ID NO: 34, SEQ ID NO: 36, and SEQ ID NO: 37.

The term "RSV F protein" or "F" protein also encompasses nucleotide sequences which encode for an RSV F and/or any variants, derivatives and/or fragments thereof that when transfected (or infected) into a host cell will express an RSV F protein and induce formation of VLPs. In some embodiments, the RSV F polypeptide comprises the sequence set forth in SEQ ID NO: 23, SEQ ID NO: 26, SEQ ID NO: 29, SEQ ID NO: 32, SEQ ID NO: 34, SEQ ID NO: 36, or SEQ ID NO: 37, or sequence having at or greater than about 80%, about 85%, about 90%, about 95%, about 98%, or about 99% homology with the sequence set forth in SEQ ID NO: 23, SEQ ID NO: 26, SEQ ID NO: 29, SEQ ID NO: 32, SEQ ID NO: 34, SEQ ID NO: 36, or SEQ ID NO: 37, or a polypeptide comprising a portion of the sequence set forth in SEQ ID NO: 23, SEQ ID NO: 26, SEQ ID NO: 29, SEQ ID NO: 32, SEQ ID NO: 34, SEQ ID NO: 36, or SEQ ID NO: 37. In some embodiments, the nucleotide sequence encoding the RSV F polypeptide comprises the sequence set forth in SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 35, or SEQ ID NO: 38, or sequence having at or greater than about 80%, about 85%, about 90%, about 95%, about 98%, or about 99% homology with SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 35, or SEQ ID NO: 38, or a polynucleotide comprising a portion of SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 35, or SEQ ID NO: 38.

In some embodiments, the carbonyl terminal portion form of the RSV F polypeptide comprises the sequence set forth in SEQ ID NO: 32, or sequence having at or greater than about 80%, about 85%, about 90%, about 95%, about 98%, or about 99% homology with SEQ ID NO: 32, or a polypeptide comprising a portion of SEQ ID NO: 32. The term also encompasses nucleotide sequences which encode for the carbonyl terminal portion form of the RSV F polypeptide and/or any variants, derivatives and/or fragments thereof that when transfected (or infected) into a host cell will express the carbonyl terminal portion form of the RSV F polypeptide and induce formation of VLPs. In some embodiments, the nucleotide sequence encoding the carbonyl terminal portion form of the RSV F polypeptide comprises the sequence set forth in SEQ ID NO: 33, or sequence having at or greater than about 80%, about 85%, about 90%, about 95%, about 98%, or about 99% homology with SEQ ID NO: 33, or a polynucleotide comprising a portion of SEQ ID NO: 33.

In some embodiments, the VLP of any preceding aspect further comprises an RSV G protein. In some embodiments, the RSV G protein is from RSV group A or RSV group B. In some embodiments, the RSV G protein is from RSV group A. In some embodiments, the RSV G protein is from RSV group B. In some embodiments, the RSV G protein is from RSV group A and RSV group B.

As used herein, the terms "RSV G protein" or "G protein" refers to a type II transmembrane glycoprotein with a single hydrophobic region near the N-terminal end that serves as both an uncleaved signal peptide and a membrane anchor, leaving the C-terminal two-thirds of the molecule oriented externally. In some embodiments, the RSV G polypeptide comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or sequence having at or greater than about 80%, about 85%, about 90%, about 95%, about 98%, or about 99% homology with a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or a polypeptide comprising a portion of a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21. The term also encompasses nucleotide sequences which encode for the RSV G polypeptide and/or any variants, derivatives and/or fragments thereof that when transfected (or infected) into a host cell will express the post-fusion form of the RSV G and induce formation of VLPs. In some embodiments, the nucleotide sequence encoding the RSV G protein comprises a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or sequence having at or greater than about 80%, about 85%, about 90%, about 95%, about 98%, or about 99% homology with a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or a polynucleotide comprising a portion of a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22. In some embodiments, the G protein comprises a sequence of SEQ ID NO: 1. In some embodiments, the G protein comprises a sequence of SEQ ID NO: 11. In some embodiments, the G protein comprises a sequence of SEQ ID NO: 15. In some embodiments, the G protein comprises a sequence of SEQ ID NO: 17.

The G protein structure consists of a central conserved region (CCD-G) that contains a CX3C chemokine motif that enables binding to the CX3C chemokine receptor, CX3CR1 (HGNC: 2558, Entrez Gene: 1524, Ensembl: ENSG00000168329, OMIM: 601470, UniProtKB: P49238), a crucial chemokine receptor involved in migration and adhesion of leukocytes. G protein induced inflammatory responses can be reduce by blocking G protein binding to CX3CR1. The present disclosure shows that the anti-G protein antibodies induced by the vaccine disclosed herein reduce RSV infection related inflammation. Therefore, in some embodiments, the VLPs of any preceding aspect comprises a recombinant RSV G protein, wherein the recombinant RSV G protein comprises a transmembrane domain of an RSV G protein and/or a CCD-G of an RSV G protein, wherein the RSV G protein is from RSV group A and/or group B. In some embodiments, the transmembrane domain of an RSV G protein comprises amino acid 1-86 of an RSV from group A, amino acid 1-86 of an RSV from group B, or amino acid 1-77 of an RSV from group B. In some embodiments, the CCD-G domain of an RSV G protein comprises amino acid 155-206 of an RSV G protein of group A, amino acid 155-206 of an RSV G protein of group B, or amino acid 146-197 of an RSV G protein of group B. In some embodiments, the RSV G protein of group A comprises a sequence of SEQ ID NO: 7 or SEQ ID NO: 9. In some embodiments, the RSV G protein of group B comprises a sequence of SEQ ID NO: SEQ ID NO: 19 or SEQ ID NO: 21.

In some embodiments, recombinant RSV G protein is a G protein comprising one or more transmembrane domains of RSV G proteins and one or more CCD-G domains of RSV G proteins, wherein the transmembrane domain and the CCD-G domain can be from a same RSV group or different RSV groups. In some embodiments, the recombinant RSV G protein comprises a transmembrane domain of an RSV G protein and a CCD-G domain of an RSV G protein, wherein the transmembrane domain and the CCD-G domain can be from a same RSV group or different RSV groups. Thus, in some embodiments, the VLP disclosed herein comprises a recombinant RSV G protein comprising a transmembrane domain of an RSV G protein of RSV group A and a CCD-G domain of an RSV G protein of RSV group A. In some embodiments, the VLP disclosed herein comprises a recombinant RSV G protein comprising a transmembrane domain of an RSV G protein of RSV group A and a CCD-G domain of an RSV G protein of RSV group B. In some embodiments, the VLP disclosed herein comprises a recombinant RSV G protein comprising a transmembrane domain of an RSV G protein of RSV group B and a CCD-G domain of an RSV G protein of RSV group B. In some embodiments, the recombinant RSV G protein comprises more than one transmembrane domain of an RSV G protein and more than one CCD-G domain of an RSV G protein, wherein the transmembrane domain and the CCD-G domain can be from a same RSV group or different RSV groups, wherein the RSV group can be RSV group A and/or group B. The recombinant RSV G protein of any preceding aspect, the transmembrane domain is operably linked to the CCD-G domain.

Accordingly, in some embodiments, the recombinant G protein of any preceding aspect comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21. In some embodiments, the recombinant G protein comprises a sequence selected from the group consisting of SEQ ID NO:

1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or sequence having at or greater than about 80%, about 85%, about 90%, about 95%, about 98%, or about 99% homology with a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, or a polypeptide comprising a portion of a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21. In some embodiments, the nucleotide sequence encoding the recombinant G protein comprises a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or sequence having at or greater than about 80%, about 85%, about 90%, about 95%, about 98%, or about 99% homology with a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22, or a polynucleotide comprising a portion of a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22. In some embodiments, the recombinant G protein comprises a sequence of SEQ ID NO: 1. In some embodiments, the recombinant G protein comprises a sequence of SEQ ID NO: 3. In some embodiments, the recombinant G protein comprises a sequence of SEQ ID NO: 5. In some embodiments, the recombinant G protein comprises a sequence of SEQ ID NO: 7. In some embodiments, the recombinant G protein comprises a sequence of SEQ ID NO: 9. In some embodiments, the recombinant G protein comprises a sequence of SEQ ID NO: 11. In some embodiments, the recombinant G protein comprises a sequence of SEQ ID NO: 13. In some embodiments, the recombinant G protein comprises a sequence of SEQ ID NO: 15. In some embodiments, the recombinant G protein comprises a sequence of SEQ ID NO: 17. In some embodiments, the recombinant G protein comprises a sequence of SEQ ID NO: 19. In some embodiments, the recombinant G protein comprises a sequence of SEQ ID NO: 21.

In some embodiments, the VLP of any preceding aspect further comprises an RSV P protein, an RSV N protein, or an RSV L protein.

In some aspects, disclosed herein is a virus like particle (VLP) comprising a respiratory syncytial virus (RSV) M protein, an RSV P protein, an RSV F protein, and an RSV G protein.

In some embodiments, the RSV F protein is selected from a group consisting of a pre-fusion form of the RSV F protein, a post-fusion form of the RSV F protein, and a carbonyl terminal portion of the RSV F protein. In some embodiments, the RSV F protein comprises a sequence selected from the group consisting of SEQ ID NO: 23, SEQ ID NO: 26, SEQ ID NO: 29, SEQ ID NO: 32, SEQ ID NO: 34, SEQ ID NO: 36, and SEQ ID NO: 37. In some embodiments, the carbonyl terminal portion of the RSV F protein comprises a sequence of SEQ ID NO: 32.

In some embodiments, the VLP comprises an RSV G protein. In some embodiments, the RSV G protein is from RSV group A or RSV group B. In some embodiments, the RSV G protein comprises a sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21.

As used herein, the terms "RSV P protein", "P protein" refers to an RSV phosphorylation. The colocalization of M2-1 protein with N protein and P protein as part of the ribonucleoprotein (RNP) complex contributes RSV viral gene transcription and replication. An example of an RSV P protein is represented by SEQ ID NO: 47 or SEQ ID NO: 49. The term also comprises any variants, derivatives and/or fragments of RSV P protein that, when expressed in a host cell, induces formation of VLPs. In some embodiments, the P polypeptide comprises the sequence set forth in SEQ ID NO: 47 or SEQ ID NO: 49, or sequence having at or greater than about 80%, about 85%, about 90%, about 95%, about 98%, or about 99% homology with SEQ ID NO: 47 or SEQ ID NO: 49, or a polypeptide comprising a portion of SEQ ID NO: 47 or SEQ ID NO: 49. The term also encompasses nucleotide sequences which encode for RSV P and/or any variants, derivatives and/or fragments thereof that when transfected (or infected) into a host cell will express RSV P protein and induce formation of VLPs. In some embodiments, the nucleotide sequence encoding RSV P protein comprises the sequence set forth in SEQ ID NO: 48 or SEQ ID NO: 50, or sequence having at or greater than about 80%, about 85%, about 90%, about 95%, about 98%, or about 99% homology with SEQ ID NO: 48 or SEQ ID NO: 50, or a polypeptide comprising a portion of SEQ ID NO: 48 or SEQ ID NO: 50.

In some embodiments, disclosed herein is a virus like particle (VLP) comprising a respiratory syncytial virus (RSV) M protein, an RSV P protein, an RSV F protein, and an RSV G protein, wherein the VLP further comprises an RSV M2-1 protein, an RSV N protein, or an RSV L protein.

In some aspects, disclosed herein are vaccines comprising VLPs of any preceding aspect. In some embodiments, the vaccine further comprises an adjuvant.

Optionally, the vaccine contemplated herein can be combined with an adjuvant such as Freund's incomplete adjuvant, Freund's Complete adjuvant, alum, monophosphoryl lipid A, alum phosphate or hydroxide, QS-21, salts, i.e., AlK(SO4)2, AlNa(SO4)2, AlNH4(SO4)2, silica, kaolin, carbon polynucleotides, i.e., poly IC and poly AU. Additional adjuvants can include QuilA and Alhydrogel and the like. Optionally, the vaccine contemplated herein can be combined with immunomodulators and immunostimulants such as interleukins, interferons and the like. Many vaccine formulations are known to those of skill in the art.

In some embodiments, the vaccine further comprises a pharmaceutically acceptable carrier.

The vaccines of the present invention can be administered to the appropriate subject in any manner known in the art, e.g., orally intramuscularly, intravenously, sublingual mucosal, intraarterially, intrathecally, intradermally, intraperitoneally, intranasally, intrapulmonarily, intraocularly, intravaginally, intrarectally or subcutaneously. They can be introduced into the gastrointestinal tract or the respiratory tract, e.g., by inhalation of a solution or powder containing the conjugates. In some embodiments, the compositions can be administered via absorption via a skin patch. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. In some embodiments, the one or more effective doses of the vaccine are administered to the subject via a route that is selected from the group consisting of an intramuscular route, a subcutaneous route, an intradermal route, an oral administration, a nasal administration, and inhalation.

A pharmaceutical composition (e.g., a vaccine) is administered in an amount sufficient to elicit production of antibodies and activation of CD4+ T cells and CD8+ T cells as part of an immunogenic response. Dosage for any given patient depends upon many factors, including the patient's size, general health, sex, body surface area, age, the particular compound to be administered, time and route of administration, and other drugs being administered concurrently. Determination of optimal dosage is well within the abilities of a pharmacologist of ordinary skill.

The vaccine compositions are administered to subjects which may become infected by a *Listeria* described herein, including but not limited to dogs, cats, rabbits, rodents, horses, livestock (e.g., cattle, sheep, goats, and pigs), zoo animals, ungulates, primates, and humans. In some embodiments, the preferred subject is a human. In some embodiments, the subject is an infant or a child. In some embodiments, the human has an age less than 15 years old, 12 years old, 11 years old, 10 years old, 9 years old, 8 years old, 7 years old, 6 years old, 5 years old, 4 years old, 3 years old, 2 years old, or 1 year old.

EXAMPLES

The following examples are set forth below to illustrate the compounds, systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Expression of G and F on RSV M Based Virus-Like Particles

VLPs were generated from sequentially transfecting 293F cells with codon-optimized DNA plasmids containing RSV genes. The order of transfection is listed in Table 1. Western blot studies showed the successful development of VLPs with the M plus phosphoprotein P or the M plus M2-1 protein platforms with F or F and G (FIG. 1A), but only to very low levels with G alone, a condition not observed in VLPs expressing only F (FIG. 1C). The Western blot studies show detection of F or F and G in the supernatant and not the cell pellet of the induced 293F cells. Additionally, F or F and G were detected by Western blot in the pellet after centrifugation through a sucrose cushion indicating the proteins were particles and not dissolved in the media. Finally, F and M or F, G, and M were detected by Western blot in the same fractions after sucrose gradient purification indicating successful expression and purified of VLPs containing F or F and G (FIGS. 1A and 1B). The fact that G alone led to very low expression in VLPs and G with F gave high levels of VLPs with both indicated that F facilitated incorporation of G into VLPs. To further test this, a truncated F that consisted of the carbonyl terminus+transmembrane+ 26 amino acids of the amino terminus ($F_t$) was generated and this peptide was co-expressed with full-length G on M+P flatform. The data show that in the presence of $F_t$, G expression was abundant (FIG. 1C).

TABLE 1

| Generation of RSV VLPs | | | | |
|---|---|---|---|---|
| | Order of transfection | | | |
| VLPs | $1^{st}$ | $2^{nd}$ | $3^{rd}$ | $4^{th}$ |
| M | M | | | |
| MFP | M | P | F | |
| MFPG | M | P | F | G |
| MFPG$_P$ | M | P | F | G$_P$ |
| MFM2-1 | M | M2-1 | F | |
| MFM2-1G | M | M2-1 | F | G |
| MFM2-1G$_P$ | M | M2-1 | F | G$_P$ |

Since this platform allows incorporating different F and G constructs into the VLPs, further modification was done to make the F protein constructs most effective at inducing an anti-viral response and G protein constructs most effective at inducing anti-viral, anti-inflammatory responses. For example, RSV VLPs with M, M2-1, F and a truncated G (referred to as "$G_P$"; intracellular, transmembrane, and the $1^{st}$ 20 aa of the extracellular domain plus aa 155-206 of the G protein) were developed. This construct focuses on inducing antibodies against CCD-G, not other parts of G, and improves anti-CCD-G antibody titers. Because G's central conserved domain is crucial for the vaccines developed herein, the current study generated a G peptide that consisted of amino acids 1-86+155-206 ($G_P$) and generated full-length F and this $G_P$ on the same VLPs utilizing either M+P or M+M2-1 flatform. Immunoblotting results from sucrose gradient show F, $G_P$, and M bands from the same fractions, indicating that they were from the same particles (FIG. 1B).

RSV M protein based VLPs with M2-1+F, M2-1+F+G, and P+F+G have not been reported previously. The M2-1 protein has two advantages over the P protein; it is part of the structural proteins that stabilize the RSV virion structure, i.e. better models the natural virus, and it facilitates T-cells immune responses, making RSV M+M2-1 VLPs an ideal RSV vaccine. Importantly, with either the RSV M+P or M+M2-1 VLPs, the structure of G can be modified to focus the response on the part of G important for inducing anti-inflammatory and anti-viral immune responses, i.e. the central conserved domain of G (CCD-G). CCD-G includes amino acids 155-206 on the G protein. The sequences are highly conserved within but not between the two antigenic/ genetic groups of RSV, A and B. In primary human airway epithelial cells and in human infection, CX3CR1 is an important receptor for infection and anti-CCD-G antibodies have an added anti-viral effect in humans.

Example 2. Electron Microscopic Study of VLPs

Electron microscopic studies of both MGFP and MFGM2-1 were performed to confirm the expression of G and F on VLPs. Negative stain showing spikes on VLP surface which were confirmed to include F spikes and/or G spikes by immunogold labeling with human anti-F motavizumab or human anti-G 3D3 monoclonal antibodies. Thus, the above data confirm successful generation of RSV matrix protein M+P or M+M2-1 based VLPs expressing both G and F.

Example 3. Immunogenicity of VLPs

Figures 3A, 3B, 3C:
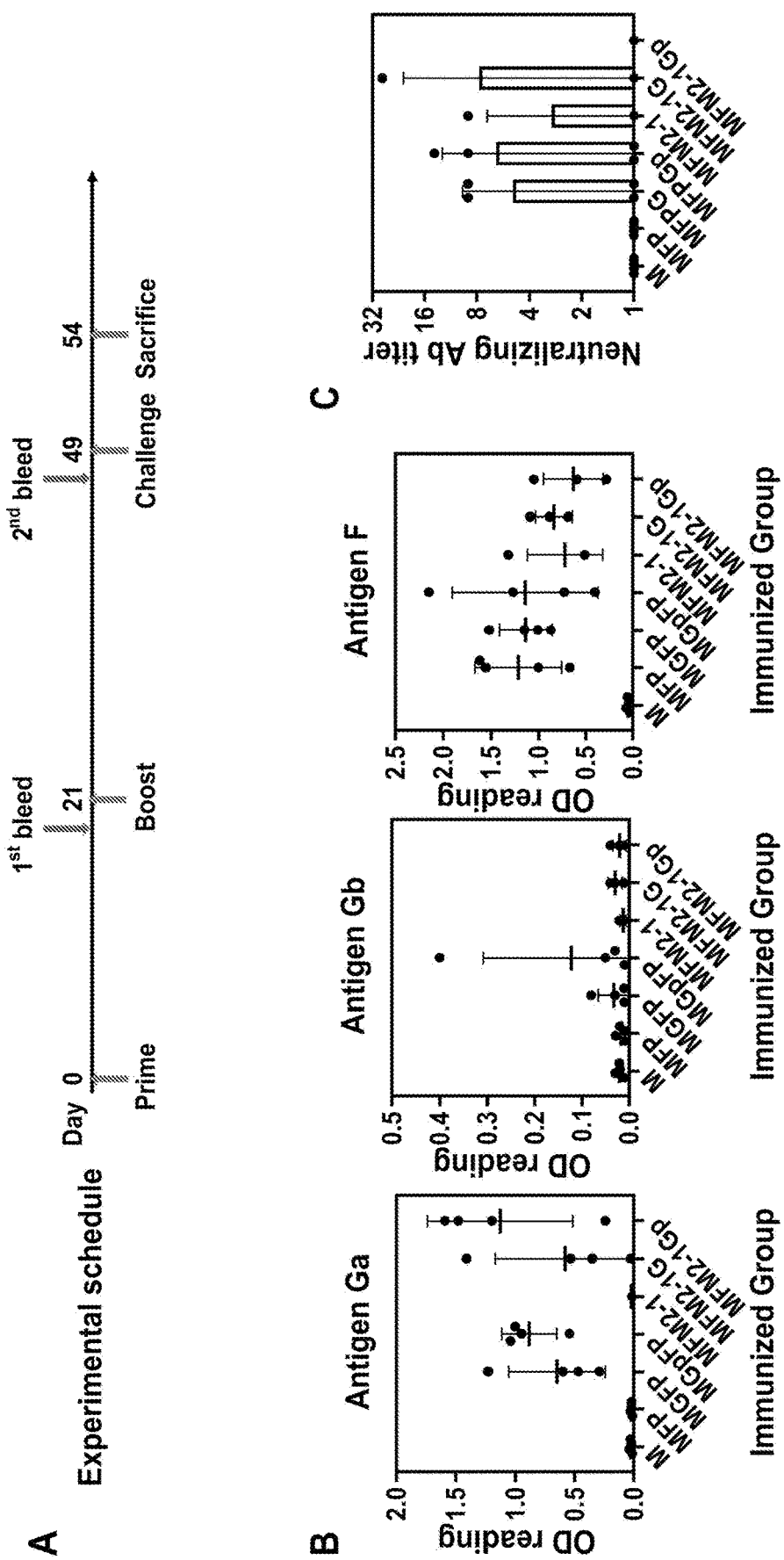
FIGS. 3A-3C show that immunized animals generate serum anti-G and anti-F antibodies.

To determine the immunogenicity of the VLPs, BALB/c mice (n=4) were immunized with various VLPs as detailed in Table 2. All immunized animals were challenged with $10^6$ TCID50 of RSV r19F at 4 weeks after the 2", booster, immunization (FIG. 3A). Blood specimens were collected before challenge and tested for F, Ga, and Gb binding antibodies by EIA and neutralizing antibodies by a microneutralization assay. All F and G VLP immunized animals and none of the control M VLP immunized animals developed F and Ga antibodies. Only one animal produced antibodies against Gb antigen (FIG. 3B). In addition, the short G peptide $G_P$ was more efficient at inducing antibody than its full-length counterpart, indicating that the central conserved domain of G is an effective immunogen. Furthermore, VLP antigens that contained P induced antibodies against F better than those that contained M2-1 (FIG. 3B). In this study, the VLPs induced low levels of neutralizing antibodies. As shown, sera from animals in groups immunized with MFP and MFM2-1$G_P$ did not possess neutralizing activity, but sera from other groups all had some neutralizing activity (FIG. 3C).

TABLE 2

Immunization schedule

| Group | N | Dose (per mouse) | Immunization days | Route | RSV challenge TCID50/ mouse | Days of harvest |
|---|---|---|---|---|---|---|
| M | 4 | 50 µg VLPs | 0, 21 | IM | $10^6$ at day 49 | 54 |
| MFP | " | " | " | " | $10^6$ at day 49 | " |
| MFGP | " | " | " | " | $10^6$ at day 49 | " |
| MFG$_P$P | " | " | " | " | $10^6$ at day 49 | " |
| MFM2-1 | " | " | " | " | $10^6$ at day 49 | " |
| MFGM2-1 | " | " | " | " | $10^6$ at day 49 | " |
| MFG$_P$M2-1 | " | " | " | " | $10^6$ at day 49 | " |

Example 4. Immunized Animals have Reduced Lung Viral Titers

Figure 4:
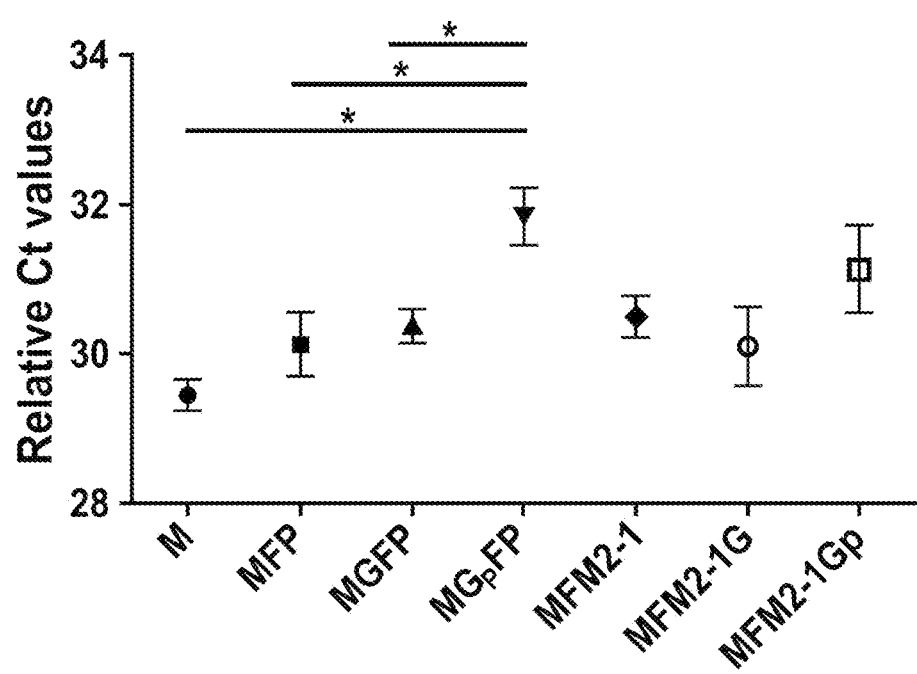
FIG. 4 shows that immunized animals have significant less lung viral titer. Lungs from immunized animals were homogenized as described in materials and methods. Aliquots stored at −80° C. were thawed and total RNA was extracted from lung. RNAs were then reverse transcribed into cDNAs. These were used as templates in RT-PCR using CYBR green and a pair of RSV matrix protein M specific primers as described. In parallel, similar reactions were performed using a pair of β-actin specific primers as controls. Results were expressed as relative amount of RSV M compared to β-actin. * p<0.05.

Next, the ability of the VLPs to prevent virus replication after challenge was investigated. The relative cycle threshold (CT) values were significant higher indicating less virus replication in animal groups that had P protein as part of the antigen VLPs, i.e. MFP, MFGP, and MFG$_P$P compared to the control antigen (M only VLPs). A higher value of CT correlates with low copy of the gene being evaluated. Also, there were significant differences between MFG$_P$P and MFP or MFGP (FIG. 4), indicating that anti-G antibodies participate in viral clearance in the lungs and that $G_P$ was more effective in facilitating virus clearance than full length G. Moreover, VLP antigens that contained M2-1 protein, i.e. MFM2-1, MFGM2-1, and MFG$_P$M2-1 had higher CT values compared to control (FIG. 4).

Example 5. Lung histopathology

Figure 5A:
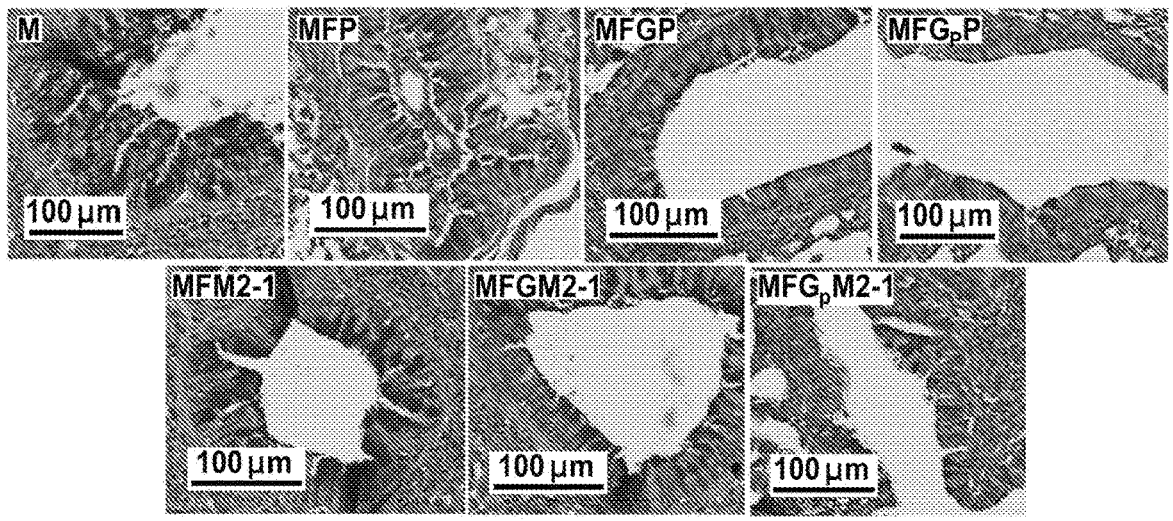
FIGS. 5A and 5B shows that immunized animals had significant less lung mucin. Female BALB/c mice (4-6 weeks) were divided in 7 groups (n=4), immunized, and challenged as summarized in table 2. Lungs were collected, fixed, and stained with Periodic-acid Schiff (PAS) staining as described in materials and methods. The slides were analyzed by Aperio ImageScope software and scored blindly on a 0-4 scale and subsequently converted to a 0-100% histopathology scale.
Figure 5B:
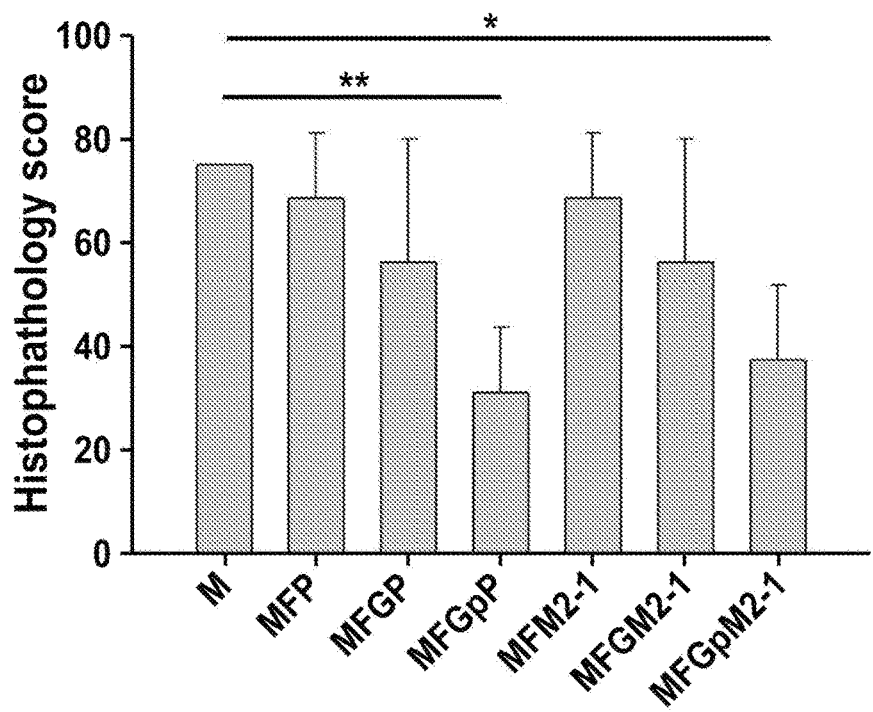
Figure 7:
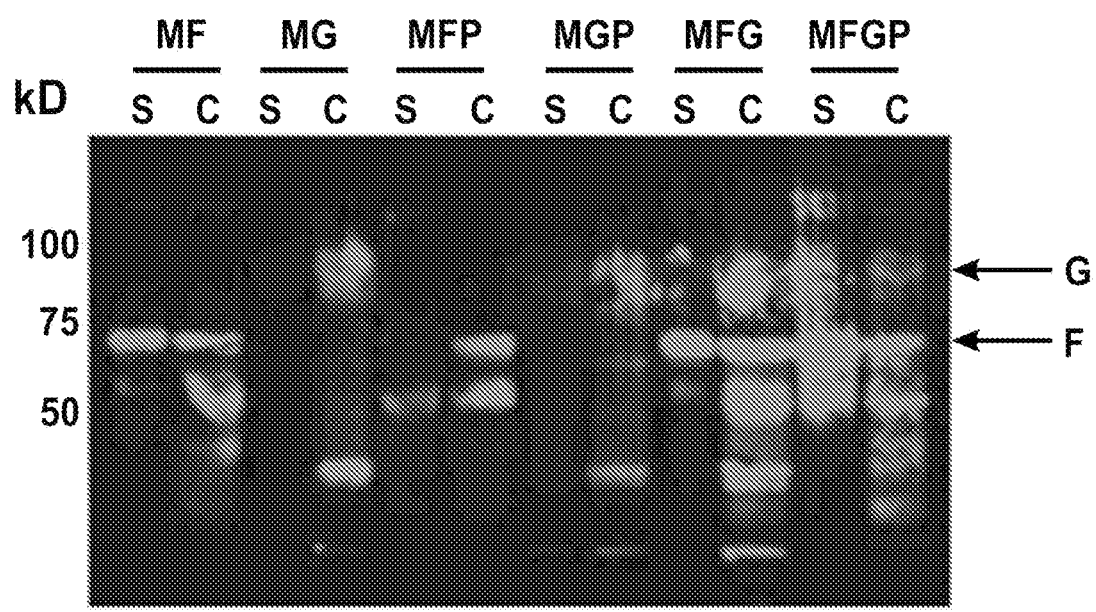
FIG. 7 shows G and/or F expression of RSV VLPs. 293F cells expressing VLPs were induced for 72 h. Cell supernatants were collected, centrifuged, purified through 0.45p m filter and 20% sucrose at 10,000×g for 2 h, 4° C. Pellets resuspended in PBS as well as solubilized cells were analyzed by immunoblotting with anti-G (3D3) and anti-F (motavizumab) antibodies. S: supernatant; C, cells.
Figure 8:
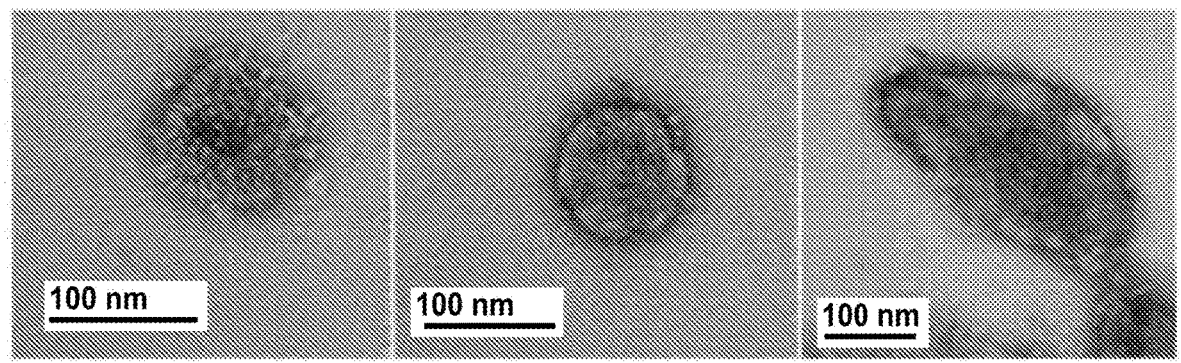
FIG. 8 shows that glycoproteins are visualized as spikes on VLPs by negative stain electron microscopy. A 3 µl aliquot containing the diluted sample was applied for 1 minute onto a formvar/carbon coated, 300 mesh-copper grid that has been glow discharged for 3 seconds, then negatively stained with 0.75% freshly-made uranyl formate on ice for 1 minute. Data were collected using a FEI T20 electron microscope operating at 200 kV (pixel size 1.101 A, total electron dose is 54 electrons/A square).
Figure 9:
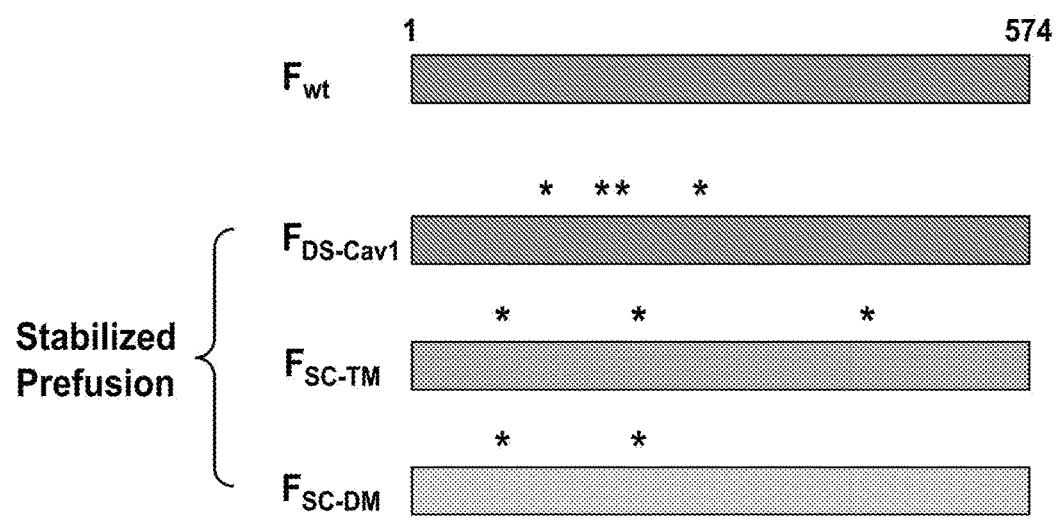
FIG. 9 shows a schematic of examples of RSV F proteins. DS-Cav1: this structure-based design generates a stabilized prefusion F structure that retains antigenic site Ø (recognized by the prefusion specific antibody D25). This is achieved by creating a double-mutation at amino acids S155C and S290C forming a stable F trimer. That combines with S190F and V207L hydrophobic pair mutations that fill a cavity in the structure creating DS-Cav1. SC-DM and SC-TM are both designed to have a short linker between F1 and F2 subunits of the F protein. Further mutations in the F secondary structure to limit transformation from prefusion to postfusion conformation at N67I and S215P creates SC-DM. Additional mutation at E487Q to minimize negative repulsion generates SC-TM.

Since one of the manifestations of RSV infection with r19F virus is overproduction of mucin, pulmonary inflammation was examined in challenged animals by Periodic acid-Schiff staining (PAS). The stained slides were analyzed by Aperio ImageScope software (Leica, Germany) and scored blindly using 0-4 severity scale then converted to 0-100 histopathology scale. Positive PAS staining was found, indicating the presence of mucin, in the lungs of all immunized animals but less so than the control animals immunized with M only VLPs (FIGS. 5A and 5B). Only MFG$_P$P- and MFG$_P$M2-1-immunized animals had a significant reduction of PAS staining compared to control animals though (FIGS. 5A and 5B). These data show that F plus Gp VLPs were most effective at reducing both lung virus replication and mucin production.

Example 6. Discussion

An RSV based VLP platform is developed herein to express F+G, F+G peptide, or G plus a truncated F. The G plus truncated F VLP makes it possible to study G without most of the extracellular F protein, and approximates the structure, function, and immunogenicity of G in an RSV VLP platform without F. The carboxy terminal intracellular plus transmembrane plus a part of the initial extracellular domain of F was needed to efficiently incorporate G into the VLPs. These data show that the RSV VLP platform has advantages over the platforms previously used in Newcastle disease or influenza virus or bacterial phage P22 platforms with the RSV F and/or G proteins.

The RSV platform VLPs better represent native structures of F and G, and facilitate studies of their structure and function relationships. It also provides an all RSV antigen platform to develop F and G VLP vaccines. A truncated F ($F_t$) that consists of the carbonyl terminus+transmembrane+ 26 amino acids of the amino terminus was generated and was co-expressed with a full-length G in M+P RSV VLP platform. This led to efficient G+Ft VLPs which can be used to study G with minimal interference by extracellular F. The data also determined that peptides of extracellular G can be incorporated as a mean to focus responses to certain regions of G. Studies show a critical role of the central conserved domain of G (CCD-G) in RSV disease pathogenesis and generating anti-CCD-G antibodies decreases disease through both an anti-viral and anti-inflammatory effect. CCD-G contains the CX3C motif through which G binds to CX3CR1 and antibodies that block binding to CX3CR1 decreases infection since CX3CR1 is an important receptor for infection of human airway epithelial cells. Studies in animals and in human cells in vitro show that blocking binding to CX3CR1 effects the inflammatory response to RSV. The present disclosure shows the successful generation of VLPs with a truncated G composed of amino acids 1-86+155-206 of G ($G_P$) with F in both M+P and M+M2-1 platforms.

P plays a crucial role in RSV polymerase activity interacting with both N and L protein in the process and also interacts with M2-1, but these roles do not suggest how it might help VLP formation when co-expressed with M. The M2-1 protein has transcription anti-termination activity and directly interacts with the M matrix protein providing a link to the RNA containing nucleocapsid.

Electron microscope negative stain studies revealed that both MFGP and MFGM2-1 VLPs expressed glycoproteins F and G as "spikes". Immunoelectron microscopic studies confirmed the presence of F and G on VLP surfaces. No significant electron microscopic differences were observed between the two platforms of VLPs. The mouse studies show that the VLPs were immunogenic and induced serum antibodies against both F and G proteins at similar levels with either platform. Notably, the VLPs with Gp induced higher antibody titers and were more effective than VLPs with full length G. The M2-1 protein is effective at inducing short term protective T cell immunity, making it an ideal antigen for vaccine design. Of note, the G protein sequences used in this study are from a group A strain, A2 and these G sequences efficiently induced antibodies against a group A but not a group B G protein. Note that though CCD-G region, with the exception of a 13 amino acid sequence, is distinct between group A and group B strains, most of CCD-G is conserved within a group. Also, serum neutralizing antibody titers were tested, showing that immunized animals developed low levels of neutralizing antibodies. VLPs with a pre-fusion stabilized F protein can be more effective at inducing neutralizing antibodies. Furthermore, animals immunized with $G_P$ and F expressed in either M plus P or M plus M2-1 VLPs had reduced lung viral titer and lung inflammation compared to those immunized with the control VLPs, demonstrating that both VLP platforms were effective.

The current VLPs described herein can express F and/or G with two RSV platforms (M+P proteins or M+M2-1 proteins). With both platforms F and/or G can be modified to focus specific structural and antigenic features of the proteins. Given the failures in RSV vaccine development, combining the highly effective anti-viral activity of F-induced antibodies plus anti-inflammatory and immune-enhancing features of G provides an effective RSV vaccine.

Example 7. Materials and Methods

Cells, Media and Plasmids: 293F cells stably transfected with plasmid pcDNA6/TR were provide by Dr. Xuemin Chen (Emory University) and cultured in freestyle 293 media (Gibco) on a shaker at 37° C., 8% $CO_2$. pcDNA3.1 DNA plasmids containing codon-optimized RSV genes M, M2-1, P, G from A2 strain, and F from A2 strain were provided by Dr. Marty Moore (now at Meissa Vaccines) were digested by KpnI and XhOI enzymes and cloned into KpnI and XhOI double digested pcDNA4/TO or pcDNA5/TO vector. Human codon optimized truncated Gof amino acids 1-86+155-206 and synthesized by Genescript (Piscataway, NJ). The gene provided in pUC57 plasmid was double digested by BamHI and XhOI enzymes and cloned into BamHI and XhOI double digested pcDNA5/TO vector. All genes were sequenced to confirm authenticity prior to transfection. To generate VLPs, 293F cells were sequentially and stably transfected with the RSV genes noted below.

Virus-like particles expression and purification: 20-30× $10^6$ 293F cells were induced with 2 µg/ml of doxycycline for 72 h. Cells were centrifuged at 300×g for 10 min and the VLP-containing media was filtered through 0.45 µm filter followed by centrifugation through 20% sucrose cushion at 12,200×g for 2 h at 4° C. (SW Ti 32 rotor, Optima L-90K Ultracentrifuge, Beckman Coulter). The top layer of cell media and sucrose was thoroughly removed and the pellet was soaked in sterile PBS for 1 h on ice and resuspended. For sucrose gradient experiments, preparation of a linear sucrose gradient was described previously [Stone A B et al., 2009], 1 ml of the gradient was removed before the resuspended VLPs was layered onto the gradient and centrifuged with a Beckman Coulter SW 41 rotor at 11,000×g for 12 h at 4° C. A total of 10 1-ml fractions were removed from top, diluted 3× with sterile PBS, and centrifuged at 12,000×g for 1 h at 4° C. on a bench-top refrigerator. Supernatants were completely removed and pellets were soaked in sterile PBS for 1 h on ice before being resuspended.

Antibodies and Immunoblotting: the anti-G protein monoclonal antibody (mAb) 3D3 was provide by Trellis Bioscience (Redwood City, CA); the anti-F protein mAb motavizumab was provided by MedImmune (Gaithersburg, MD); rabbit serum anti-M antibody was provided by Dr. Oomens (Oklahoma State University); and goat anti RSV antibody was obtained from Millipore (Burlington, MA). All anti-species fluorescent-conjugated secondary antibodies used in immunoblotting were obtained from LI-COR biosciences (Lincoln, NE). All HRP-conjugated secondary antibodies used in enzyme-linked immunosorbent assays (EIAs) were obtained from Jackson ImmunoResearch (West Grove, PA). For immunoblotting experiments, VLP samples were mixed with 2× Laemmli sample buffer (Bio-Rad) and boiled at 95° C. for 5 min. Samples were run on SDS-PAGE, transferred to a nitrocellulose membrane, blocked for 30 min in blocking buffer (5% dry milk in TTBS). After blotting with primary antibody (incubation period), membrane was washed 3× in TTBS following secondary antibody incubation (time) and 3× washes in TTBS. Signals were visualized by Odyssey CLX imaging system (LI-COR).

F, Ga, and Gb antibody EIAs: the secreted form of F, Ga or Gb protein antigens was produced from stably transfected 293F cells in serum-free media and coated onto 96-well microtiter plate in buffer. The plates were incubated in 2% nonfat dry milk dissolved in PBS blocking solution for 2 h at 37° C., washed with PBS-T, and serum specimens at 1:200 dilution added to the wells, incubated for 1 h at 37° C., the plates washed with PBS-T, and goat anti mouse IgG-HRP (1:5,000) added and incubated for 1 h at 37° C. Color was developed with OPD substrate and the reaction stopped after r 30 min at RT with 4N H2SO4. Optical density (OD) was measured at 490 nm and geometric mean of the $OD_{490}$ was calculated from the triplicate wells.

RSV neutralizing antibody assay: heat inactivated sera were serially 2-fold diluted starting with a 1:10 dilution in MEM containing 0.5% FBS, incubated with RSV/A2 (100 TCID50) for 1 h at RT, and inoculated in triplicates onto non-confluent HEp-2 monolayers in 96-well plates for 1 h at 37° C. in a 5% $CO_2$ incubator. MEM containing 5% FBS was added to all the wells and cells were incubated for 3 days at 37° C. in a 5% $CO_2$ incubator. Cells were washed with PBS and fixed with 4% paraformaldehyde and RSV antigens detected by EIA with goat anti RSV antibody (1:5,000) followed with donkey anti goat IgG-HRP secondary antibody (1:5,000). Color was developed with OPD substrate and neutralization defined as a ≥50% reduction in OD value. The titer was estimated using the Reed and Much method. The geometric means±SEM for all animals in a group at any given time were calculated.

Virus: A recombinant virus of RSV A2 backbone expressing the F protein from L19 virus (r19F) [Moore M L et al., 2009] was chosen as the challenge virus since it induces airway disease that parallel RSV infection in humans but not seen with RSV A2. Stock virus was prepared by inoculating onto subconfluent HEp-2 at a multiplicity of infection (MOI) 0.01 for 2 h at 37° C. in 5% $CO_2$ incubator using 0.5% fetal bovine serum (FBS)-containing minimal essential medium (MEM). 5% FBS MEM was added and cells were incubated in 37° C., 5% $CO_2$ incubator for 3 days. Cells were frozen and thawed twice at −80 C and 4° C., respectively, and centrifuged at 2,000 rpm for 15 min at 4° C. to remove cellular debris. The supernatant was layered onto 20% sucrose layer and centrifuged at 12,200×g for 2 h at 4° C. Pellet was resuspended in serum free MEM, divided into aliquots, and snap frozen in liquid nitrogen. The aliquots were stored at −80° C. until use. The infectivity titer of the inoculum was determined by serial 10-fold dilutions in subconfluent HEp-2 cell monolayer for 3 days and virus replication detected by EIA for RSV antigens with goat-anti RSV antibody. Titer was estimated from wells with absorbance >3 standard deviations above the mean absorbance for wells without virus by Reed and Muench method.

Animal study: 4-6 weeks old female BALB/c mice were purchased from Charles River Lab (Wilmington, MA) and housed at Emory's Pediatric animal facility under food ad libitum in microisolator cages with auto sterilized water. All animal handlings and procedures were carried out according to protocol approved by Emory University (Atlanta, GA) Institutional Animals Care and Use Committee. For challenge study, mice were intranasally infected with $10^6$ CTID50 RSV r19F A2 in 40 µl.

Real-time PCR: total RNA was extracted and purified from lung homogenates using Qiagen RNeasy kit (QIAGEN). RNA was reverse transcribed into cDNA using iScript™ cDNA synthesis kit (Bio-Rad) following the manufacturer's instruction. Quantitative PCR was carried out on a 7500 Fast Real-time PCR system (Applied Biosystems) using Power SYBR Green PCR master mix (Applied Biosystems). CT values were normalized using control j-actin CT values from the same samples. RSV matrix M gene primers and amplification cycles were described previously [Boyoglu-Barnum S et al., 2017]. Other primer pairs used were: β-actin, forward 5'-CAC CAA CTG GGA CGA CAT-3', reverse 5'-ACA GCC TGG ATA GCA ACG-3'. mRNA levels were expressed as the geometric mean±SEM for all animals in a group.

Pulmonary histopathology: lungs were isolated and fixed in 10% neutral buffered formalin for 24 h. The lungs were then embedded in paraffin, sectioned, and stained with Periodic acid-Schiff (PAS). Slides were analyzed by Aperio ImageScope software (Leica) and scored blinded to treatment on a 0-4 scale and subsequently converted to a 0-100% histopathology scale.

Statistical Analysis: unless otherwise indicated, different groups were compared by Wilcoxon rank sum test or Wilcoxon matched pairs test. A p value of <0.05 was considered statistically significant. Data are shown as means and standard errors of the mean (SEM).

REFERENCES

1. Hall C B, Simoes E A, Anderson L J. Clinical and epidemiologic features of respiratory syncytial virus. *Curr Top Microbiol Immunol.* 2013; 372:39-57.
2. Shi T, McAllister D A, O'Brien K L, et al. Global, regional, and national disease burden estimates of acute lower respiratory infections due to respiratory syncytial virus in young children in 2015: a systematic review and modelling study. *Lancet.* 2017; 390(10098):946-958.
3. Jartti T, Gern J E. Role of viral infections in the development and exacerbation of asthma in children. *J Allergy Clin Immunol.* 2017; 140(4):895-906.
4. Wu P, Hartert T V. Evidence for a causal relationship between respiratory syncytial virus infection and asthma. *Expert Rev Anti Infect Ther.* 2011; 9(9):731-745.
5. Stockman L J, Curns A T, Anderson L J, Fischer-Langley G. Respiratory Syncytial Virus-associated Hospitalizations Among Infants and Young Children in the United States, 1997-2006. *Pediatr Infect Dis J.* 2012; 31(1):5-9.
6. Hall C B, Weinberg G A, Iwane M K, et al. The burden of respiratory syncytial virus infection in young children. *N Engl J Med.* 2009; 360(6):588-598.
7. Mazur N I, Higgins D, Nunes M C, et al. The respiratory syncytial virus vaccine landscape: lessons from the graveyard and promising candidates. *Lancet Infect Dis.* 2018; 18(10):e295-e311.
8. Collins P L, Fearns R, Graham B S. Respiratory Syncytial Virus: Virology, Reverse Genetics, and Pathogenesis of Disease. In: Anderson L J, Graham B S, eds. Challenges and Opportunities for Respiratory Syncytial Virus Vaccines. *Current Topics in Microbiology and Immunology,* vol 372. Vol 372. Berlin, Heidelberg Springer; 2013:3-38.
9. Anderson L J. Respiratory syncytial virus vaccine development. *Seminars in immunology.* 2013; 25(2):160-171.
10. Schepens B, Sedeyn K, Vande Ginste L, et al. Protection and mechanism of action of a novel human respiratory syncytial virus vaccine candidate based on the extracellular domain of small hydrophobic protein. *EMBO Mol Med.* 2014; 6(11):1436-1454.
11. Ngwuta J O, Chen M, Modjarrad K, et al. Prefusion F-specific antibodies determine the magnitude of RSV neutralizing activity in human sera. *Science translational medicine.* 2015; 7(309):309ra162.
12. Graham B S. Immunological goals for respiratory syncytial virus vaccine development. *Curr Opin Immunol.* 2019; 59:57-64.
13. Tripp R A, Power U F, Openshaw P J M, Kauvar L M. Respiratory Syncytial Virus: Targeting the G Protein Provides a New Approach for an Old Problem. *J Virol.* 2018; 92(3).
14. Tripp R A. CX3C chemokine mimicry by respiratory syncytial virus G glycoprotein. In: Mahalingam S, ed. *Chemokines in Viral Infection.* Landes Bioscience; 2003.
15. Boyoglu-Barnum S, Gaston K A, Todd S O, et al. A respiratory syncytial virus (RSV) anti-G protein F(ab')2 monoclonal antibody suppresses mucous production and breathing effort in RSV rA2-line19F-infected BALB/c mice. *J Virol.* 2013; 87(20):10955-10967.
16. Boyoglu-Barnum S, Todd S O, Chirkova T, et al. An anti-G protein monoclonal antibody treats RSV disease more effectively than an anti-F monoclonal antibody in BALB/c mice. *Virology.* 2015; 483:117-125.
17. Radu G U, Caidi H, Miao C, Tripp R A, Anderson L J, Haynes L M. Prophylactic treatment with a G glycoprotein monoclonal antibody reduces pulmonary inflammation in respiratory syncytial virus (RSV)-challenged naive and formalin-inactivated RSV-immunized BALB/c mice. *J Virol.* 2010; 84(18):9632-9636.
18. Rey G U, Miao C, Caidi H, et al. Decrease in formalin-inactivated respiratory syncytial virus (FI-RSV) enhanced disease with RSV G glycoprotein peptide immunization in BALB/c mice. *PLoS One.* 2013; 8(12):e83075.
19. Jorquera P A, Choi Y, Oakley K E, et al. Nanoparticle vaccines encompassing the respiratory syncytial virus (RSV) G protein CX3C chemokine motif induce robust immunity protecting from challenge and disease. *PLoS One.* 2013; 8(9):e74905.
20. Zhang W, Choi Y, Haynes L M, et al. Vaccination to induce antibodies blocking the CX3C-CX3CR1 interaction of respiratory syncytial virus G protein reduces pulmonary inflammation and virus replication in mice. *J Virol.* 2010; 84(2):1148-1157.
21. Murawski M R, McGinnes L W, Finberg R W, et al. Newcastle disease virus-like particles containing respiratory syncytial virus G protein induced protection in 21. BALB/c mice, with no evidence of immunopathology. *J Virol.* 2010; 84(2):1110-1123.
22. Quan F S, Kim Y, Lee S, et al. Viruslike particle vaccine induces protection against respiratory syncytial virus infection in mice. *J Infect Dis.* 2011; 204(7):987-995.
23. Schwarz B, Morabito K M, Ruckwardt T J, et al. Viruslike Particles Encapsidating Respiratory Syncytial Virus M and M2 Proteins Induce Robust T Cell Responses. *ACS Biomater Sci Eng.* 2016; 2(12):2324-2332.
24. Meshram C D, Baviskar P S, Ognibene C M, Oomens A G P. The Respiratory Syncytial Virus Phosphoprotein, Matrix Protein, and Fusion Protein Carboxy-Terminal Domain Drive Efficient Filamentous Virus-Like Particle Formation. *J Virol.* 2016; 90(23):10612-10628.
25. Shaikh F Y, Cox R G, Lifland A W, et al. A critical phenylalanine residue in the respiratory syncytial virus fusion protein cytoplasmic tail mediates assembly of internal viral proteins into viral filaments and particles. *mBio.* 2012; 3(1).
26. Walpita P, Johns L M, Tandon R, Moore M L. Mammalian Cell-Derived Respiratory Syncytial Virus-Like Particles Protect the Lower as well as the Upper Respiratory Tract. *PLoS One.* 2015; 10(7):e0130755.
27. Stone A B. A simplified method for preparing sucrose gradients. *Biochem J.* 1974; 137(1):117-118.
28. Moore M L, Chi M H, Luongo C, et al. A chimeric A2 strain of respiratory syncytial virus (RSV) with the fusion protein of RSV strain line 19 exhibits enhanced viral load, mucus, and airway dysfunction. *J Virol.* 2009; 83(9):4185-4194.
29. Boyoglu-Barnum S, Todd S O, Meng J, et al. Mutating the CX3C Motif in the G Protein Should Make a Live Respiratory Syncytial Virus Vaccine Safer and More Effective. *J Virol.* 2017; 91(10).
30. Liu J, Haddad E K, Marceau J, et al. A Numerically Subdominant CD8 T Cell Response to Matrix Protein of Respiratory Syncytial Virus Controls Infection with Limited Immunopathology. *PLoS Pathog.* 2016; 12(3):e1005486.
31. Kiss G, Holl J M, Williams G M, et al. Structural analysis of respiratory syncytial virus reveals the position of M2-1 between the matrix protein and the ribonucleoprotein complex. *J Virol.* 2014; 88(13):7602-7617.
32. Li D, Jans D A, Bardin P G, Meanger J, Mills J, Ghildyal R. Association of respiratory syncytial virus M protein with viral nucleocapsids is mediated by the M2-1 protein. *J Virol.* 2008; 82(17):8863-8870.
33. Chirkova T, Lin S, Oomens A G, et al. CX3CR1 is an important surface molecule for respiratory syncytial virus infection in human airway epithelial cells. *J Gen Virol.* 2015; 96(9):2543-2556.
34. Jeong K I, Piepenhagen P A, Kishko M, et al. CX3CR1 Is Expressed in Differentiated Human Ciliated Airway Cells and Co-Localizes with Respiratory Syncytial Virus on Cilia in a G Protein-Dependent Manner. *PLoS One.* 2015; 10(6):e0130517.
35. Johnson S M, McNally B A, Ioannidis I, et al. Respiratory Syncytial Virus Uses CX3CR1 as a Receptor on Primary Human Airway Epithelial Cultures. *PLoS Pathog.* 2015; 11(12):e1005318.
36. Chirkova T, Boyoglu-Barnum S, Gaston K A, et al. Respiratory syncytial virus G protein CX3C motif impairs human airway epithelial and immune cell responses. *J Virol.* 2013; 87(24):13466-13479.
37. Meshram C D, Baviskar P S, Ognibene C M, Oomens A G. The Respiratory Syncytial Virus Phosphoprotein, Matrix Protein, and Fusion Protein Carboxy-Terminal Domain Drive Efficient Filamentous Virus-Like Particle Formation. *J Virol.* 2016; 90(23):10612-10628.
38. Cowton V M, McGivern D R, Fearns R. Unravelling the complexities of respiratory syncytial virus RNA synthesis. *J Gen Virol.* 2006; 87(Pt 7):1805-1821.
39. Bakker S E, Duquerroy S, Galloux M, et al. The respiratory syncytial virus nucleoprotein-RNA complex forms a left-handed helical nucleocapsid. *J Gen Virol.* 2013; 94(Pt 8):1734-1738.
40. Tawar R G, Duquerroy S, Vonrhein C, et al. Crystal structure of a nucleocapsid-like nucleoprotein-RNA complex of respiratory syncytial virus. *Science.* 2009; 326(5957):1279-1283.
41. Esperante S A, Paris G, de Prat-Gay G. Modular unfolding and dissociation of the human respiratory syncytial virus phosphoprotein p and its interaction with the m(2-1) antiterminator: a singular tetramer-tetramer interface arrangement. *Biochemistry.* 2012; 51(41):8100-8110.
42. Fearns R, Collins P L. Role of the M2-1 transcription antitermination protein of respiratory syncytial virus in sequential transcription. *J Virol.* 1999; 73(7):5852-5864.
43. Tanner S J, Ariza A, Richard C A, et al. Crystal structure of the essential transcription antiterminator M2-1 protein of human respiratory syncytial virus and implications of its phosphorylation. *Proc Natl Acad Sci USA.* 2014; 111(4):1580-1585.
44. Ke Z, Dillard R S, Chirkova T, et al. The Morphology and Assembly of Respiratory Syncytial Virus Revealed by Cryo-Electron Tomography. *Viruses.* 2018; 10(8).
45. Collins P L C J. Respiratory syncytial virus and metapneumovirus. In: *Fields virology, 5th ed.* Philadelphia, PA: Lippincott Williams & Wilkins; 2007:1601-1646.
46. Connors M, Collins P L, Firestone C-Y, Murphy B R. Respiratory syncytial virus (RSV) F, G, M2 (22K), and N proteins each induce resistance to RSV Challenge, but resistance induced by M2 and N proteins is relatively short-lived. *J Virol.* 1991; 65:1634-1637.
47. Green C A, Scarselli E, Sande C J, et al. Chimpanzee adenovirus- and MVA-vectored respiratory syncytial virus vaccine is safe and immunogenic in adults. *Science translational medicine.* 2015; 7(300):300ra126.
48. McLellan J S, Ray W C, Peeples M E. Structure and function of respiratory syncytial virus surface glycoproteins. *Curr Top Microbiol Immunol.* 2013; 372:83-104.
49. McLellan J S, Chen M, Joyce M G, et al. Structure-based design of a fusion glycoprotein vaccine for respiratory syncytial virus. *Science.* 2013; 342(6158):592-598.
50. Krarup A, Truan D, Furmanova-Hollenstein P, et al. A highly stable prefusion RSV F vaccine derived from structural analysis of the fusion mechanism. *Nat Commun.* 2015; 6:8143.
51. McLellan J S, Chen M, Joyce M G, et al. Structure-based design of a fusion glycoprotein vaccine for respiratory syncytial virus. *Science.* 2013; 342(6158):592-598.
51. Krarup A, Truan D, Furmanova-Hollenstein P, et al. A highly stable prefusion RSV F vaccine derived from structural analysis of the fusion mechanism. *Nat Commun.* 2015; 6:8143.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A virus like particle (VLP) comprising a respiratory syncytial virus (RSV) M protein, an RSV P protein, an RSV F protein, and an RSV G protein, wherein
the RSV F protein comprises SEQ ID NO: 23 or
the RSV G protein comprises SEQ ID NO: 1.

2. The VLP of claim 1, wherein the RSV F protein comprises SEQ ID NO: 23.

3. The VLP of claim 1, wherein the RSV G protein comprises SEQ ID NO: 1.

4. The VLP of claim 1, wherein the RSV G protein is a recombinant RSV G protein.

5. A vaccine comprising the VLP of claim 1.

6. The vaccine of claim 5, further comprising an adjuvant.

7. A method of inducing immunity to RSV infection or at least one symptom thereof in a subject, comprising administering one or more effective doses of the vaccine of claim 5.

8. The method of claim 7, wherein the one or more effective doses of the vaccine are administered to the subject via a route that is selected from the group consisting of an intramuscular route, a subcutaneous route, an intradermal route, an oral administration, a nasal administration, and inhalation.

* * * * *